US008419653B2

(12) United States Patent
Bleich et al.

(10) Patent No.: US 8,419,653 B2
(45) Date of Patent: Apr. 16, 2013

(54) SPINAL ACCESS AND NEURAL LOCALIZATION

(75) Inventors: Jeffery L. Bleich, Palo Alto, CA (US);
Ron Leguidleguid, Fremont, CA (US);
Jefferey Bleam, Boulder Creek, CA (US)

(73) Assignee: Baxano, Inc., San Jose, CA (US)

( * ) Notice: Subject to any disclaimer, the term of this patent is extended or adjusted under 35 U.S.C. 154(b) by 387 days.

(21) Appl. No.: 12/504,545

(22) Filed: Jul. 16, 2009

(65) Prior Publication Data

US 2010/0010334 A1  Jan. 14, 2010

Related U.S. Application Data

(60) Division of application No. 11/457,416, filed on Jul. 13, 2006, now Pat. No. 7,578,819, which is a continuation-in-part of application No. 11/251,205, filed on Oct. 15, 2005, now Pat. No. 7,918,849, and a continuation-in-part of application No. 11/375,265, filed on Mar. 13, 2006, now Pat. No. 7,887, 538.

(60) Provisional application No. 60/681,864, filed on May 16, 2005.

(51) Int. Cl.
*A61B 5/05* (2006.01)
*A61B 5/04* (2006.01)
*A61N 1/00* (2006.01)

(52) U.S. Cl.
USPC ........... 600/554; 600/393; 607/115; 607/117; 607/145

(58) Field of Classification Search ................. 600/393, 600/554; 607/115–119, 122, 133, 134, 138, 607/145, 146
See application file for complete search history.

(56) References Cited

U.S. PATENT DOCUMENTS

| 184,804 | A | 11/1876 | Stohlmann |
| 289,104 | A | 11/1883 | How |

(Continued)

FOREIGN PATENT DOCUMENTS

| DE | 3209403 A1 | 9/1983 |
| DE | 4036804 A1 | 5/1992 |

(Continued)

OTHER PUBLICATIONS

Schmitz et al., U.S. Appl. No. 12/496,094 entitled "Access and tissue modification systems and methods," filed Jul. 1, 2009.*

(Continued)

*Primary Examiner* — Max Hindenburg
*Assistant Examiner* — John Pani
(74) *Attorney, Agent, or Firm* — Shay Glenn LLP

(57) ABSTRACT

A method for locating neural tissue in a patient body may involve: advancing a probe along a natural tissue interface between the neural tissue and another tissue in the body, the probe having a first surface oriented toward the neural tissue and a second surface oriented away from the neural tissue; delivering a first electrical current to a first electrode along the first surface of the probe; delivering a second electrical current to a second electrode along the second surface of the probe; and verifying that the first surface of the advanced probe remains oriented toward the neural tissue and the second surface remains oriented away from the neural tissue by monitoring neural response to the first and second electrical currents.

13 Claims, 66 Drawing Sheets

U.S. PATENT DOCUMENTS

| | | |
|---|---|---|
| 863,389 A | 8/1907 | Harkin |
| 1,039,487 A | 9/1912 | Casebolt |
| 1,201,467 A | 10/1916 | Hoglund |
| 1,374,638 A | 4/1921 | De Cew et al. |
| 1,543,195 A | 6/1925 | Thygesen |
| 1,690,812 A | 11/1928 | Bertels |
| 1,938,200 A | 12/1933 | Wells |
| 2,243,757 A | 5/1941 | Kohls et al. |
| 2,269,749 A | 1/1942 | Wilkie |
| 2,372,553 A | 3/1945 | Coddington |
| 2,437,697 A | 3/1948 | Kalom |
| 2,516,882 A | 8/1950 | Kalom |
| 2,704,064 A | 5/1955 | Fizzell |
| 2,820,281 A | 1/1958 | Amsen |
| 2,843,128 A | 7/1958 | Storz |
| 2,982,005 A | 5/1961 | Booth |
| RE25,582 E | 5/1964 | Davies |
| 3,150,470 A | 9/1964 | Barron |
| 3,200,814 A | 8/1965 | Taylor et al. |
| 3,389,447 A | 6/1968 | Theobald et al. |
| 3,491,776 A | 1/1970 | Fleming |
| 3,495,590 A | 2/1970 | Zeiller |
| 3,528,152 A | 9/1970 | Funakubo et al. |
| 3,624,484 A | 11/1971 | Colyer |
| 3,640,280 A | 2/1972 | Slanker et al. |
| 3,651,844 A | 3/1972 | Barnes |
| 3,664,329 A | 5/1972 | Naylor |
| 3,682,162 A | 8/1972 | Colyer |
| 3,699,729 A | 10/1972 | Garvey et al. |
| 3,752,166 A | 8/1973 | Lyon et al. |
| 3,774,355 A | 11/1973 | Dawson et al. |
| 3,830,226 A | 8/1974 | Staub et al. |
| 3,835,859 A | 9/1974 | Roberts et al. |
| 3,956,858 A | 5/1976 | Catlin et al. |
| 3,957,036 A | 5/1976 | Normann |
| 3,978,862 A | 9/1976 | Morrison |
| 3,999,294 A | 12/1976 | Shoben |
| 4,015,931 A | 4/1977 | Thakur |
| 4,099,519 A | 7/1978 | Warren |
| 4,108,182 A | 8/1978 | Hartman et al. |
| 4,160,320 A | 7/1979 | Wikoff |
| 4,172,440 A | 10/1979 | Schneider et al. |
| 4,203,444 A | 5/1980 | Bonnell et al. |
| 4,207,897 A | 6/1980 | Lloyd et al. |
| 4,259,276 A | 3/1981 | Rawlings |
| 4,405,061 A | 9/1983 | Bergandy |
| D273,806 S | 5/1984 | Bolesky et al. |
| 4,464,836 A | 8/1984 | Hissa |
| 4,502,184 A | 3/1985 | Karubian |
| 4,515,168 A | 5/1985 | Chester et al. |
| 4,518,022 A | 5/1985 | Valdes et al. |
| 4,545,374 A | 10/1985 | Jacobson |
| 4,573,448 A | 3/1986 | Kambin |
| 4,580,545 A | 4/1986 | Dorsten |
| 4,590,949 A | 5/1986 | Pohndorf |
| 4,616,660 A | 10/1986 | Johns |
| 4,621,636 A | 11/1986 | Fogarty |
| 4,625,725 A | 12/1986 | Davison et al. |
| 4,660,571 A | 4/1987 | Hess et al. |
| 4,678,459 A | 7/1987 | Onik et al. |
| 4,690,642 A | 9/1987 | Kyotani |
| 4,700,702 A | 10/1987 | Nilsson |
| 4,709,699 A | 12/1987 | Michael et al. |
| 4,741,343 A | 5/1988 | Bowman |
| 4,750,249 A | 6/1988 | Richardson |
| 4,794,931 A | 1/1989 | Yock |
| 4,808,157 A | 2/1989 | Coombs |
| 4,817,628 A | 4/1989 | Zealear et al. |
| 4,856,193 A | 8/1989 | Grachan |
| 4,867,155 A | 9/1989 | Isaacson |
| 4,872,452 A | 10/1989 | Alexson |
| 4,873,978 A | 10/1989 | Ginsburg |
| 4,883,460 A | 11/1989 | Zanetti |
| 4,894,063 A | 1/1990 | Nashe |
| 4,912,799 A | 4/1990 | Coleman, Jr. |
| RE33,258 E | 7/1990 | Onik et al. |
| 4,943,295 A | 7/1990 | Hartlaub et al. |
| 4,946,462 A | 8/1990 | Watanabe |
| 4,957,117 A | 9/1990 | Wysham |
| 4,962,766 A | 10/1990 | Herzon |
| 4,973,329 A | 11/1990 | Park et al. |
| 4,990,148 A | 2/1991 | Worrick, III et al. |
| 4,994,036 A | 2/1991 | Biscoping et al. |
| 4,994,072 A | 2/1991 | Bhate et al. |
| 4,995,200 A | 2/1991 | Eberhart |
| 5,019,082 A | 5/1991 | Frey et al. |
| 5,025,787 A | 6/1991 | Sutherland et al. |
| 5,026,379 A | 6/1991 | Yoon |
| 5,026,386 A | 6/1991 | Michelson |
| 5,078,137 A | 1/1992 | Edell et al. |
| 5,089,003 A | 2/1992 | Fallin et al. |
| 5,100,424 A | 3/1992 | Jang et al. |
| 5,108,403 A | 4/1992 | Stern |
| 5,125,928 A | 6/1992 | Parins et al. |
| 5,147,364 A | 9/1992 | Comparetto |
| 5,152,749 A | 10/1992 | Giesy et al. |
| 5,161,534 A | 11/1992 | Berthiaume |
| 5,163,939 A | 11/1992 | Winston |
| 5,176,649 A | 1/1993 | Wakabayashi |
| 5,178,145 A | 1/1993 | Rea |
| 5,178,161 A | 1/1993 | Kovacs |
| 5,191,888 A | 3/1993 | Palmer et al. |
| 5,195,507 A | 3/1993 | Bilweis |
| 5,201,704 A | 4/1993 | Ray |
| 5,215,105 A | 6/1993 | Kizelshteyn et al. |
| 5,219,358 A | 6/1993 | Bendel et al. |
| 5,234,435 A | 8/1993 | Seagrave, Jr. |
| 5,242,418 A | 9/1993 | Weinstein |
| 5,250,035 A | 10/1993 | Smith et al. |
| 5,255,691 A | 10/1993 | Otten |
| 5,271,415 A | 12/1993 | Foerster et al. |
| 5,281,218 A | 1/1994 | Imran |
| 5,284,153 A | 2/1994 | Raymond et al. |
| 5,284,154 A | 2/1994 | Raymond et al. |
| 5,300,077 A | 4/1994 | Howell |
| 5,325,868 A | 7/1994 | Kimmelstiel |
| 5,341,807 A | 8/1994 | Nardella |
| 5,351,679 A | 10/1994 | Mayzels et al. |
| 5,353,784 A | 10/1994 | Nady-Mohamed |
| 5,353,789 A | 10/1994 | Schlobohm |
| 5,353,802 A | 10/1994 | Ollmar |
| 5,360,441 A | 11/1994 | Otten |
| 5,365,928 A | 11/1994 | Rhinehart et al. |
| 5,374,261 A | 12/1994 | Yoon |
| 5,383,879 A | 1/1995 | Phillips |
| 5,385,146 A | 1/1995 | Goldreyer |
| 5,387,218 A | 2/1995 | Meswania |
| 5,396,880 A | 3/1995 | Kagan et al. |
| 5,421,348 A | 6/1995 | Larnard |
| 5,423,331 A | 6/1995 | Wysham |
| 5,437,661 A | 8/1995 | Rieser |
| 5,439,464 A | 8/1995 | Shapiro |
| 5,441,044 A | 8/1995 | Tovey et al. |
| 5,441,510 A | 8/1995 | Simpson et al. |
| 5,454,815 A | 10/1995 | Geisser et al. |
| 5,456,254 A | 10/1995 | Pietroski et al. |
| 5,496,325 A | 3/1996 | McLees |
| 5,512,037 A | 4/1996 | Russell et al. |
| 5,515,848 A | 5/1996 | Corbett, III et al. |
| 5,531,749 A | 7/1996 | Michelson |
| 5,534,009 A | 7/1996 | Lander |
| 5,546,958 A | 8/1996 | Thorud et al. |
| 5,554,110 A | 9/1996 | Edwards et al. |
| 5,555,892 A | 9/1996 | Tipton |
| 5,560,372 A | 10/1996 | Cory |
| 5,562,695 A | 10/1996 | Obenchain |
| 5,571,181 A | 11/1996 | Li |
| 5,582,618 A | 12/1996 | Chin et al. |
| 5,598,848 A | 2/1997 | Swanson et al. |
| 5,620,447 A | 4/1997 | Smith et al. |
| 5,630,426 A | 5/1997 | Eggers et al. |
| 5,634,475 A | 6/1997 | Wolvek |
| 5,643,304 A | 7/1997 | Schechter et al. |
| 5,651,373 A | 7/1997 | Mah |
| 5,656,012 A | 8/1997 | Sienkiewicz |
| 5,680,860 A | 10/1997 | Imran |
| 5,681,324 A | 10/1997 | Kammerer et al. |

| | | | | | | |
|---|---|---|---|---|---|---|
| 5,697,889 A | 12/1997 | Slotman et al. | 6,251,115 B1 | 6/2001 | Williams et al. | |
| 5,709,697 A | 1/1998 | Ratcliff et al. | 6,256,540 B1 | 7/2001 | Panescu et al. | |
| 5,725,530 A | 3/1998 | Popken | 6,259,945 B1 | 7/2001 | Epstein et al. | |
| 5,735,792 A | 4/1998 | Vanden Hoek et al. | 6,261,582 B1 | 7/2001 | Needham et al. | |
| 5,755,732 A | 5/1998 | Green et al. | 6,266,551 B1 | 7/2001 | Osadchy et al. | |
| 5,759,159 A | 6/1998 | Masreliez | 6,266,558 B1 | 7/2001 | Gozani et al. | |
| 5,762,629 A | 6/1998 | Kambin | 6,267,760 B1 | 7/2001 | Swanson | |
| 5,766,168 A | 6/1998 | Mantell | 6,272,367 B1 | 8/2001 | Chance | |
| 5,769,865 A | 6/1998 | Kermode et al. | 6,277,094 B1 | 8/2001 | Schendel | |
| 5,775,331 A | 7/1998 | Raymond et al. | 6,280,447 B1 | 8/2001 | Marino et al. | |
| 5,779,642 A | 7/1998 | Nightengale | 6,292,702 B1 | 9/2001 | King et al. | |
| 5,788,653 A | 8/1998 | Lorenzo | 6,298,256 B1 | 10/2001 | Meyer | |
| 5,792,044 A | 8/1998 | Foley et al. | 6,312,392 B1 | 11/2001 | Herzon | |
| 5,795,308 A | 8/1998 | Russin | 6,324,418 B1 | 11/2001 | Crowley et al. | |
| 5,800,350 A | 9/1998 | Coppleson et al. | 6,324,432 B1 | 11/2001 | Rigaux et al. | |
| 5,803,902 A | 9/1998 | Sienkiewicz et al. | 6,325,764 B1 | 12/2001 | Griffith et al. | |
| 5,803,904 A | 9/1998 | Mehdizadeh | 6,334,068 B1 | 12/2001 | Hacker | |
| 5,807,263 A | 9/1998 | Chance | 6,343,226 B1 | 1/2002 | Sunde et al. | |
| 5,810,744 A | 9/1998 | Chu et al. | 6,358,254 B1 | 3/2002 | Anderson | |
| 5,813,405 A | 9/1998 | Montano, Jr. et al. | 6,360,750 B1 | 3/2002 | Gerber et al. | |
| 5,824,040 A | 10/1998 | Cox et al. | 6,364,886 B1 | 4/2002 | Sklar | |
| 5,830,151 A | 11/1998 | Hadzic et al. | 6,368,324 B1 | 4/2002 | Dinger et al. | |
| 5,830,157 A | 11/1998 | Foote | 6,370,411 B1 | 4/2002 | Osadchy et al. | |
| 5,830,188 A | 11/1998 | Abouleish | 6,370,435 B2 | 4/2002 | Panescu et al. | |
| 5,833,692 A | 11/1998 | Cesarini et al. | 6,383,509 B1 | 5/2002 | Donovan et al. | |
| 5,836,810 A | 11/1998 | Åsum | 6,390,906 B1 | 5/2002 | Subramanian | |
| 5,836,948 A | 11/1998 | Zucherman et al. | 6,391,028 B1 | 5/2002 | Fanton et al. | |
| 5,843,110 A | 12/1998 | Dross et al. | 6,416,505 B1 | 7/2002 | Fleischman et al. | |
| 5,846,196 A | 12/1998 | Siekmeyer et al. | 6,423,071 B1 | 7/2002 | Lawson | |
| 5,846,244 A | 12/1998 | Cripe | 6,423,080 B1 | 7/2002 | Gellman et al. | |
| 5,851,191 A | 12/1998 | Gozani | 6,425,859 B1 | 7/2002 | Foley et al. | |
| 5,851,209 A | 12/1998 | Kummer et al. | 6,425,887 B1 | 7/2002 | McGuckin et al. | |
| 5,851,214 A | 12/1998 | Larsen et al. | 6,436,101 B1 | 8/2002 | Hamada | |
| 5,853,373 A | 12/1998 | Griffith et al. | 6,442,848 B1 | 9/2002 | Dean | |
| 5,865,844 A | 2/1999 | Plaia et al. | 6,446,621 B1 | 9/2002 | Svensson | |
| 5,868,767 A | 2/1999 | Farley et al. | 6,451,335 B1 | 9/2002 | Goldenheim et al. | |
| 5,879,353 A | 3/1999 | Terry | 6,454,767 B2 | 9/2002 | Alleyne | |
| 5,885,219 A | 3/1999 | Nightengale | 6,464,682 B1 | 10/2002 | Snoke | |
| 5,895,417 A | 4/1999 | Pomeranz et al. | 6,466,817 B1 | 10/2002 | Kaula et al. | |
| 5,897,583 A | 4/1999 | Meyer et al. | 6,468,289 B1 | 10/2002 | Bonutti | |
| 5,899,909 A | 5/1999 | Claren et al. | 6,470,209 B2 | 10/2002 | Snoke | |
| 5,904,657 A | 5/1999 | Unsworth et al. | 6,478,805 B1 | 11/2002 | Marino et al. | |
| 5,916,173 A | 6/1999 | Kirsner | 6,487,439 B1 | 11/2002 | Skladnev et al. | |
| 5,918,604 A | 7/1999 | Whelan | 6,488,636 B2 | 12/2002 | Bryan et al. | |
| 5,919,190 A | 7/1999 | VanDusseldorp | 6,491,646 B1 | 12/2002 | Blackledge | |
| 5,928,158 A | 7/1999 | Aristides | 6,500,128 B2 | 12/2002 | Marino | |
| 5,941,822 A | 8/1999 | Skladnev et al. | 6,500,189 B1 | 12/2002 | Lang et al. | |
| 5,961,522 A | 10/1999 | Mehdizadeh | 6,512,958 B1 * | 1/2003 | Swoyer et al. | 607/117 |
| 5,972,013 A | 10/1999 | Schmidt | 6,516,223 B2 | 2/2003 | Hofmann | |
| 5,976,110 A | 11/1999 | Greengrass et al. | 6,520,907 B1 | 2/2003 | Foley et al. | |
| 5,976,146 A | 11/1999 | Ogawa et al. | 6,527,786 B1 | 3/2003 | Davis et al. | |
| 6,002,964 A | 12/1999 | Feler et al. | 6,533,749 B1 | 3/2003 | Mitusina et al. | |
| 6,004,326 A | 12/1999 | Castro et al. | 6,535,759 B1 | 3/2003 | Epstein et al. | |
| 6,004,330 A | 12/1999 | Middleman et al. | 6,540,742 B1 | 4/2003 | Thomas et al. | |
| 6,010,493 A | 1/2000 | Snoke | 6,540,761 B2 | 4/2003 | Houser | |
| 6,015,406 A | 1/2000 | Goble et al. | 6,546,270 B1 | 4/2003 | Goldin et al. | |
| 6,022,362 A | 2/2000 | Lee et al. | 6,558,353 B2 | 5/2003 | Zohmann | |
| 6,030,383 A | 2/2000 | Benderev | 6,562,033 B2 | 5/2003 | Shah et al. | |
| 6,030,401 A | 2/2000 | Marino | 6,564,078 B1 * | 5/2003 | Marino et al. | 600/373 |
| 6,038,480 A | 3/2000 | Hrdlicka et al. | 6,564,079 B1 | 5/2003 | Cory et al. | |
| 6,048,345 A | 4/2000 | Berke et al. | 6,564,088 B1 | 5/2003 | Soller et al. | |
| 6,068,642 A | 5/2000 | Johnson et al. | 6,569,160 B1 | 5/2003 | Goldin et al. | |
| 6,073,051 A | 6/2000 | Sharkey et al. | 6,575,979 B1 | 6/2003 | Cragg | |
| 6,099,514 A | 8/2000 | Sharkey et al. | 6,579,291 B1 | 6/2003 | Keith et al. | |
| 6,102,930 A | 8/2000 | Simmons, Jr. | 6,584,345 B2 | 6/2003 | Govari | |
| 6,106,558 A | 8/2000 | Picha | 6,592,559 B1 | 7/2003 | Pakter et al. | |
| 6,113,534 A | 9/2000 | Koros et al. | 6,595,932 B2 | 7/2003 | Ferrera | |
| D432,384 S | 10/2000 | Simons | 6,597,955 B2 | 7/2003 | Panescu et al. | |
| 6,132,387 A | 10/2000 | Gozani et al. | 6,606,523 B1 | 8/2003 | Jenkins | |
| 6,136,014 A | 10/2000 | Sirimanne et al. | 6,607,530 B1 * | 8/2003 | Carl et al. | 606/914 |
| 6,142,993 A | 11/2000 | Whayne et al. | 6,609,018 B2 | 8/2003 | Cory et al. | |
| 6,142,994 A | 11/2000 | Swanson et al. | 6,610,066 B2 | 8/2003 | Dinger et al. | |
| 6,146,380 A | 11/2000 | Racz et al. | 6,620,129 B2 | 9/2003 | Stecker et al. | |
| 6,152,894 A | 11/2000 | Kubler | 6,622,731 B2 | 9/2003 | Daniel et al. | |
| 6,169,916 B1 | 1/2001 | West | 6,624,510 B1 | 9/2003 | Chan et al. | |
| 6,205,360 B1 | 3/2001 | Carter et al. | 6,626,916 B1 | 9/2003 | Yeung et al. | |
| 6,214,001 B1 | 4/2001 | Casscells et al. | 6,632,184 B1 | 10/2003 | Truwit | |
| 6,214,016 B1 | 4/2001 | Williams et al. | 6,638,233 B2 | 10/2003 | Corvi et al. | |
| 6,236,892 B1 | 5/2001 | Feler | RE38,335 E | 11/2003 | Aust et al. | |

| | | |
|---|---|---|
| 6,648,883 B2 | 11/2003 | Francischelli et al. |
| 6,666,874 B2 | 12/2003 | Heitzmann et al. |
| 6,673,063 B2 | 1/2004 | Brett |
| 6,673,068 B1 | 1/2004 | Berube |
| 6,678,552 B2 | 1/2004 | Pearlman |
| 6,682,535 B2 | 1/2004 | Hoogland |
| 6,682,536 B2 | 1/2004 | Vardi et al. |
| 6,699,246 B2 | 3/2004 | Zucherman et al. |
| 6,723,049 B2 | 4/2004 | Skladnev et al. |
| 6,726,531 B1 | 4/2004 | Harrel |
| 6,726,685 B2 | 4/2004 | To et al. |
| 6,733,496 B2 | 5/2004 | Sharkey et al. |
| 6,736,835 B2 | 5/2004 | Pellegrino et al. |
| 6,746,451 B2 | 6/2004 | Middleton et al. |
| 6,752,814 B2 | 6/2004 | Gellman et al. |
| 6,760,616 B2 | 7/2004 | Hoey et al. |
| 6,772,012 B2 | 8/2004 | Ricart et al. |
| 6,776,765 B2 | 8/2004 | Soukup et al. |
| 6,788,966 B2 | 9/2004 | Kenan et al. |
| 6,790,210 B1 | 9/2004 | Cragg et al. |
| 6,805,695 B2 | 10/2004 | Keith et al. |
| 6,805,697 B1 | 10/2004 | Helm et al. |
| 6,807,444 B2 | 10/2004 | Tu et al. |
| 6,830,561 B2 | 12/2004 | Jansen et al. |
| 6,830,570 B1 | 12/2004 | Frey et al. |
| 6,832,111 B2 | 12/2004 | Tu et al. |
| 6,845,264 B1 | 1/2005 | Skladnev et al. |
| 6,847,849 B2 | 1/2005 | Mamo et al. |
| 6,851,430 B2 | 2/2005 | Tsou |
| 6,865,409 B2 | 3/2005 | Getsla et al. |
| 6,872,204 B2 | 3/2005 | Houser |
| 6,875,221 B2 | 4/2005 | Cull |
| 6,882,879 B2 | 4/2005 | Rock |
| 6,884,220 B2 | 4/2005 | Aviv et al. |
| 6,890,353 B2 | 5/2005 | Cohn et al. |
| 6,899,716 B2 | 5/2005 | Cragg |
| 6,907,884 B2 | 6/2005 | Pellegrino et al. |
| 6,911,003 B2 | 6/2005 | Anderson et al. |
| 6,911,016 B2 | 6/2005 | Balzum et al. |
| 6,916,328 B2 | 7/2005 | Brett |
| 6,923,813 B2 | 8/2005 | Phillips et al. |
| 6,929,647 B2 | 8/2005 | Cohen |
| 6,949,104 B2 | 9/2005 | Griffis et al. |
| 6,962,587 B2 | 11/2005 | Johnson et al. |
| 6,971,986 B2 | 12/2005 | Staskin et al. |
| 6,972,199 B2 | 12/2005 | Lebouitz et al. |
| 6,973,342 B1 | 12/2005 | Swanson |
| 6,976,986 B2 | 12/2005 | Berube |
| 6,991,643 B2 | 1/2006 | Saadat |
| 6,994,693 B2 | 2/2006 | Tal |
| 6,997,934 B2 | 2/2006 | Snow et al. |
| 6,999,820 B2 | 2/2006 | Jordan |
| 7,001,333 B2 | 2/2006 | Hamel et al. |
| 7,008,431 B2 | 3/2006 | Simonson |
| 7,010,352 B2 | 3/2006 | Hogan |
| 7,011,635 B1 | 3/2006 | Delay |
| 7,011,663 B2 | 3/2006 | Michelson |
| 7,014,616 B2 | 3/2006 | Ferrera |
| 7,033,373 B2 | 4/2006 | de la Torre et al. |
| 7,041,099 B2 | 5/2006 | Thomas et al. |
| 7,047,084 B2 | 5/2006 | Erickson et al. |
| 7,048,682 B2 | 5/2006 | Neisz et al. |
| 7,050,848 B2 | 5/2006 | Hoey et al. |
| 7,063,682 B1 | 6/2006 | Whayne et al. |
| 7,070,556 B2 | 7/2006 | Anderson et al. |
| 7,070,596 B1 | 7/2006 | Woloszko et al. |
| 7,079,883 B2 | 7/2006 | Marino et al. |
| 7,081,122 B1 | 7/2006 | Reiley et al. |
| 7,087,053 B2 | 8/2006 | Vanney |
| 7,087,058 B2 | 8/2006 | Cragg |
| 7,107,104 B2 | 9/2006 | Keravel et al. |
| 7,118,576 B2 | 10/2006 | Gitis et al. |
| 7,141,019 B2 | 11/2006 | Pearlman |
| 7,166,073 B2 | 1/2007 | Ritland |
| 7,166,081 B2 | 1/2007 | McKinley |
| 7,166,107 B2 | 1/2007 | Anderson |
| 7,169,107 B2 | 1/2007 | Jersey-Willuhn et al. |
| 7,189,240 B1 | 3/2007 | Dekel |
| 7,198,598 B2 | 4/2007 | Smith et al. |
| 7,198,626 B2 | 4/2007 | Lee et al. |
| 7,207,949 B2 | 4/2007 | Miles et al. |
| 7,211,082 B2 | 5/2007 | Hall et al. |
| 7,214,186 B2 | 5/2007 | Ritland |
| 7,214,197 B2 | 5/2007 | Prass |
| 7,216,001 B2 | 5/2007 | Hacker et al. |
| 7,223,278 B2 | 5/2007 | Davison et al. |
| 7,236,832 B2 | 6/2007 | Hemmerling et al. |
| 7,239,911 B2 | 7/2007 | Scholz |
| 7,270,658 B2 | 9/2007 | Woloszko et al. |
| 7,282,061 B2 | 10/2007 | Sharkey et al. |
| 7,337,005 B2 | 2/2008 | Kim et al. |
| 7,337,006 B2 | 2/2008 | Kim et al. |
| 7,470,236 B1 | 12/2008 | Kelleher et al. |
| 7,494,473 B2 | 2/2009 | Eggers et al. |
| 7,503,920 B2 | 3/2009 | Siegal |
| 7,507,218 B2 | 3/2009 | Aliski et al. |
| 7,553,307 B2 * | 6/2009 | Bleich et al. ............... 606/1 |
| 7,555,343 B2 * | 6/2009 | Bleich ............... 607/43 |
| 7,578,819 B2 * | 8/2009 | Bleich et al. ............... 606/53 |
| 7,641,658 B2 | 1/2010 | Shaolian et al. |
| 7,655,026 B2 | 2/2010 | Justis et al. |
| 7,666,186 B2 | 2/2010 | Harp |
| 7,666,209 B2 | 2/2010 | Zucherman et al. |
| 7,857,813 B2 | 12/2010 | Schmitz et al. |
| 7,887,538 B2 | 2/2011 | Bleich et al. |
| 7,918,849 B2 | 4/2011 | Bleich et al. |
| 7,938,830 B2 | 5/2011 | Saadat et al. |
| 7,959,577 B2 * | 6/2011 | Schmitz et al. ............... 600/554 |
| 8,192,435 B2 | 6/2012 | Bleich |
| 8,192,436 B2 | 6/2012 | Schmitz |
| 2001/0014806 A1 | 8/2001 | Ellman et al. |
| 2001/0025192 A1 | 9/2001 | Gerber et al. |
| 2001/0039419 A1 | 11/2001 | Francischelli et al. |
| 2001/0049527 A1 | 12/2001 | Cragg |
| 2001/0053885 A1 | 12/2001 | Gielen et al. |
| 2002/0016555 A1 | 2/2002 | Ritchart et al. |
| 2002/0019637 A1 | 2/2002 | Frey et al. |
| 2002/0022788 A1 | 2/2002 | Corvi et al. |
| 2002/0022873 A1 | 2/2002 | Erickson et al. |
| 2002/0029060 A1 | 3/2002 | Hogendijk |
| 2002/0106681 A1 | 8/2002 | Wexler et al. |
| 2002/0138091 A1 | 9/2002 | Pflueger |
| 2002/0165590 A1 | 11/2002 | Crowe et al. |
| 2002/0183647 A1 | 12/2002 | Gozani et al. |
| 2003/0023190 A1 | 1/2003 | Cox |
| 2003/0045808 A1 | 3/2003 | Kaula et al. |
| 2003/0045937 A1 | 3/2003 | Ginn |
| 2003/0074037 A1 | 4/2003 | Moore et al. |
| 2003/0105503 A1 | 6/2003 | Marino |
| 2003/0109871 A1 | 6/2003 | Johnson et al. |
| 2003/0113906 A1 | 6/2003 | Sangha et al. |
| 2003/0130655 A1 | 7/2003 | Woloszko |
| 2003/0130738 A1 | 7/2003 | Hovda et al. |
| 2003/0167021 A1 | 9/2003 | Shimm |
| 2003/0187368 A1 | 10/2003 | Sata et al. |
| 2003/0188749 A1 | 10/2003 | Nichols et al. |
| 2003/0208206 A1 | 11/2003 | Gitis et al. |
| 2003/0212400 A1 | 11/2003 | Bloemer et al. |
| 2003/0225412 A1 | 12/2003 | Shiraishi |
| 2003/0225415 A1 | 12/2003 | Richard |
| 2004/0006379 A1 | 1/2004 | Brett |
| 2004/0006391 A1 | 1/2004 | Reiley |
| 2004/0019359 A1 | 1/2004 | Worley et al. |
| 2004/0024399 A1 | 2/2004 | Sharps et al. |
| 2004/0030330 A1 | 2/2004 | Brassell et al. |
| 2004/0049179 A1 | 3/2004 | Francischelli et al. |
| 2004/0049208 A1 | 3/2004 | Hill et al. |
| 2004/0054368 A1 | 3/2004 | Truckai et al. |
| 2004/0059247 A1 | 3/2004 | Urmey |
| 2004/0064058 A1 | 4/2004 | McKay |
| 2004/0067000 A1 | 4/2004 | Bates et al. |
| 2004/0097927 A1 | 5/2004 | Yeung et al. |
| 2004/0098074 A1 * | 5/2004 | Erickson et al. ............... 607/117 |
| 2004/0102721 A1 | 5/2004 | McKinley |
| 2004/0106940 A1 | 6/2004 | Shaolian et al. |
| 2004/0111084 A1 | 6/2004 | Brett |
| 2004/0116977 A1 | 6/2004 | Finch et al. |
| 2004/0122433 A1 | 6/2004 | Loubens et al. |

| Publication No. | Date | Inventor(s) |
|---|---|---|
| 2004/0122459 A1 | 6/2004 | Harp |
| 2004/0122482 A1 | 6/2004 | Tung et al. |
| 2004/0127893 A1 | 7/2004 | Hovda |
| 2004/0127963 A1 | 7/2004 | Uchida et al. |
| 2004/0133208 A1 | 7/2004 | Weikel et al. |
| 2004/0143165 A1 | 7/2004 | Alleyne |
| 2004/0143280 A1 | 7/2004 | Suddaby |
| 2004/0162609 A1 | 8/2004 | Hossainy et al. |
| 2004/0167444 A1 | 8/2004 | Laroya et al. |
| 2004/0167553 A1 | 8/2004 | Simpson et al. |
| 2004/0181150 A1 | 9/2004 | Evans et al. |
| 2004/0199084 A1 | 10/2004 | Kelleher et al. |
| 2004/0199159 A1 | 10/2004 | Lee et al. |
| 2004/0199166 A1 | 10/2004 | Schmieding et al. |
| 2004/0225233 A1 | 11/2004 | Frankowski |
| 2004/0260358 A1 | 12/2004 | Vaughan et al. |
| 2005/0027199 A1 | 2/2005 | Clarke |
| 2005/0033393 A1 | 2/2005 | Daglow |
| 2005/0049592 A1 | 3/2005 | Keith et al. |
| 2005/0060006 A1 | 3/2005 | Pflueger et al. |
| 2005/0075578 A1 | 4/2005 | Gharib et al. |
| 2005/0149034 A1 | 7/2005 | Assell et al. |
| 2005/0149035 A1 | 7/2005 | Pimenta et al. |
| 2005/0149154 A1 | 7/2005 | Cohen et al. |
| 2005/0171587 A1 | 8/2005 | Daglow et al. |
| 2005/0182454 A1 | 8/2005 | Gharib et al. |
| 2005/0187537 A1 | 8/2005 | Loeb et al. |
| 2005/0197661 A1 | 9/2005 | Carrison et al. |
| 2005/0203599 A1 | 9/2005 | Garabedian et al. |
| 2005/0209610 A1 | 9/2005 | Carrison |
| 2005/0209617 A1 | 9/2005 | Koven et al. |
| 2005/0209622 A1 | 9/2005 | Carrison |
| 2005/0216023 A1 | 9/2005 | Aram et al. |
| 2005/0222598 A1 | 10/2005 | Ho et al. |
| 2005/0222647 A1* | 10/2005 | Wahlstrand et al. ............ 607/72 |
| 2005/0234425 A1 | 10/2005 | Miller et al. |
| 2005/0256423 A1 | 11/2005 | Kirsner |
| 2005/0261692 A1 | 11/2005 | Carrison et al. |
| 2005/0277942 A1 | 12/2005 | Kullas et al. |
| 2005/0283148 A1 | 12/2005 | Janssen et al. |
| 2005/0283204 A1 | 12/2005 | Buhlmann et al. |
| 2006/0004369 A1 | 1/2006 | Patel et al. |
| 2006/0015035 A1 | 1/2006 | Rock |
| 2006/0025702 A1 | 2/2006 | Sterrantino et al. |
| 2006/0025703 A1 | 2/2006 | Miles et al. |
| 2006/0025797 A1 | 2/2006 | Lock et al. |
| 2006/0030854 A1 | 2/2006 | Haines |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0058732 A1 | 3/2006 | Harp |
| 2006/0064101 A1 | 3/2006 | Arramon |
| 2006/0079919 A1 | 4/2006 | Harp |
| 2006/0085048 A1 | 4/2006 | Cory et al. |
| 2006/0085049 A1 | 4/2006 | Cory et al. |
| 2006/0089609 A1 | 4/2006 | Bleich et al. |
| 2006/0089633 A1* | 4/2006 | Bleich et al. .................. 606/32 |
| 2006/0089640 A1* | 4/2006 | Bleich et al. .................. 606/45 |
| 2006/0089650 A1 | 4/2006 | Nolde |
| 2006/0089688 A1 | 4/2006 | Panescu |
| 2006/0094976 A1* | 5/2006 | Bleich ........................... 600/547 |
| 2006/0095026 A1 | 5/2006 | Ricart et al. |
| 2006/0095028 A1* | 5/2006 | Bleich ........................... 606/39 |
| 2006/0095059 A1* | 5/2006 | Bleich et al. .................. 606/170 |
| 2006/0100651 A1* | 5/2006 | Bleich ........................... 606/167 |
| 2006/0122458 A1* | 6/2006 | Bleich ........................... 600/101 |
| 2006/0122620 A1 | 6/2006 | Kim |
| 2006/0122653 A1 | 6/2006 | Bradley et al. |
| 2006/0122654 A1 | 6/2006 | Bradley et al. |
| 2006/0135882 A1 | 6/2006 | Bleich |
| 2006/0142753 A1 | 6/2006 | Francischelli et al. |
| 2006/0149278 A1 | 7/2006 | Abdou |
| 2006/0161189 A1 | 7/2006 | Harp |
| 2006/0173374 A1 | 8/2006 | Neubardt et al. |
| 2006/0184175 A1 | 8/2006 | Schomer et al. |
| 2006/0195107 A1 | 8/2006 | Jones et al. |
| 2006/0200153 A1 | 9/2006 | Harp |
| 2006/0200154 A1 | 9/2006 | Harp |
| 2006/0200155 A1 | 9/2006 | Harp |
| 2006/0200219 A1 | 9/2006 | Thrope et al. |
| 2006/0206115 A1 | 9/2006 | Schomer et al. |
| 2006/0206117 A1 | 9/2006 | Harp |
| 2006/0206118 A1 | 9/2006 | Kim et al. |
| 2006/0206178 A1 | 9/2006 | Kim |
| 2006/0224060 A1 | 10/2006 | Garell et al. |
| 2006/0224078 A1 | 10/2006 | Hoey et al. |
| 2006/0235451 A1 | 10/2006 | Schomer et al. |
| 2006/0235452 A1 | 10/2006 | Schomer et al. |
| 2006/0241648 A1* | 10/2006 | Bleich et al. .................. 606/103 |
| 2006/0258951 A1 | 11/2006 | Bleich et al. |
| 2006/0264952 A1 | 11/2006 | Nelson et al. |
| 2006/0264994 A1 | 11/2006 | Schomer et al. |
| 2006/0276720 A1 | 12/2006 | McGinnis et al. |
| 2006/0276802 A1 | 12/2006 | Vresilovic et al. |
| 2006/0276836 A1 | 12/2006 | Bergin et al. |
| 2007/0010717 A1 | 1/2007 | Cragg |
| 2007/0016097 A1 | 1/2007 | Farquhar et al. |
| 2007/0016185 A1 | 1/2007 | Tullis et al. |
| 2007/0027464 A1 | 2/2007 | Way et al. |
| 2007/0027514 A1 | 2/2007 | Gerber |
| 2007/0049962 A1 | 3/2007 | Marino et al. |
| 2007/0055215 A1 | 3/2007 | Tran et al. |
| 2007/0055262 A1 | 3/2007 | Tomita et al. |
| 2007/0055263 A1 | 3/2007 | Way et al. |
| 2007/0073356 A1 | 3/2007 | Rooney et al. |
| 2007/0106219 A1 | 5/2007 | Grabinsky |
| 2007/0123888 A1* | 5/2007 | Bleich et al. .................. 606/79 |
| 2007/0123890 A1 | 5/2007 | Way et al. |
| 2007/0162044 A1 | 7/2007 | Marino |
| 2007/0162061 A1 | 7/2007 | Way et al. |
| 2007/0162062 A1 | 7/2007 | Norton et al. |
| 2007/0166345 A1 | 7/2007 | Pavcnik et al. |
| 2007/0198019 A1 | 8/2007 | Schomer et al. |
| 2007/0213583 A1 | 9/2007 | Kim et al. |
| 2007/0213584 A1 | 9/2007 | Kim et al. |
| 2007/0213733 A1* | 9/2007 | Bleich et al. .................. 606/79 |
| 2007/0213734 A1* | 9/2007 | Bleich et al. .................. 606/79 |
| 2007/0213735 A1* | 9/2007 | Saadat et al. .................. 606/79 |
| 2007/0213795 A1* | 9/2007 | Bradley et al. ................. 607/116 |
| 2007/0225703 A1* | 9/2007 | Schmitz et al. ................. 606/53 |
| 2007/0255162 A1 | 11/2007 | Abboud et al. |
| 2007/0255369 A1 | 11/2007 | Bonde et al. |
| 2007/0260252 A1* | 11/2007 | Schmitz et al. ................. 606/79 |
| 2007/0270795 A1 | 11/2007 | Francischelli et al. |
| 2007/0270865 A1 | 11/2007 | Arnin et al. |
| 2007/0276286 A1 | 11/2007 | Miller |
| 2007/0276390 A1 | 11/2007 | Solsberg et al. |
| 2007/0282217 A1 | 12/2007 | McGinnis et al. |
| 2007/0299403 A1 | 12/2007 | Crowe et al. |
| 2007/0299459 A1 | 12/2007 | Way et al. |
| 2008/0033465 A1* | 2/2008 | Schmitz et al. ................. 606/170 |
| 2008/0051812 A1* | 2/2008 | Schmitz et al. ................. 606/167 |
| 2008/0058874 A1 | 3/2008 | Westlund et al. |
| 2008/0086034 A1* | 4/2008 | Schmitz et al. ................. 600/210 |
| 2008/0086114 A1* | 4/2008 | Schmitz et al. ................. 606/1 |
| 2008/0091227 A1* | 4/2008 | Schmitz et al. ................. 606/190 |
| 2008/0103504 A1* | 5/2008 | Schmitz et al. ................. 606/79 |
| 2008/0125621 A1 | 5/2008 | Gellman et al. |
| 2008/0125709 A1 | 5/2008 | Chang et al. |
| 2008/0146867 A1 | 6/2008 | Gellman et al. |
| 2008/0147084 A1* | 6/2008 | Bleich et al. .................. 606/114 |
| 2008/0161809 A1* | 7/2008 | Schmitz et al. ................. 606/79 |
| 2008/0161810 A1 | 7/2008 | Melkent |
| 2008/0197024 A1 | 8/2008 | Simpson et al. |
| 2008/0275458 A1* | 11/2008 | Bleich et al. .................. 606/103 |
| 2008/0288005 A1 | 11/2008 | Jackson |
| 2008/0312660 A1* | 12/2008 | Bleich et al. .................. 606/102 |
| 2008/0319459 A1 | 12/2008 | Al-najjar |
| 2009/0018507 A1* | 1/2009 | Schmitz et al. .......... 604/164.03 |
| 2009/0018610 A1 | 1/2009 | Gharib et al. |
| 2009/0069709 A1 | 3/2009 | Schmitz et al. ................. 600/547 |
| 2009/0105604 A1 | 4/2009 | Bertagnoli et al. |
| 2009/0125036 A1* | 5/2009 | Bleich ........................... 606/110 |
| 2009/0138056 A1 | 5/2009 | Anderson et al. |
| 2009/0143829 A1 | 6/2009 | Shluzas |
| 2009/0149865 A1* | 6/2009 | Schmitz et al. ................. 606/114 |
| 2009/0171381 A1* | 7/2009 | Schmitz et al. ................. 606/167 |
| 2009/0177112 A1 | 7/2009 | Gharib et al. |

| | | | |
|---|---|---|---|
| 2009/0177241 A1* | 7/2009 | Bleich et al. | 606/86 R |
| 2009/0182382 A1 | 7/2009 | Justis et al. | |
| 2009/0204119 A1* | 8/2009 | Bleich et al. | 606/79 |
| 2009/0209879 A1 | 8/2009 | Kaula et al. | |
| 2010/0057087 A1 | 3/2010 | Cha | |
| 2010/0274250 A1 | 10/2010 | Wallace et al. | |
| 2010/0331883 A1 | 12/2010 | Schmitz et al. | |
| 2010/0331900 A1 | 12/2010 | Garabedian et al. | |
| 2011/0004207 A1 | 1/2011 | Wallace et al. | |
| 2011/0046613 A1 | 2/2011 | Schmitz et al. | |
| 2011/0060314 A1 | 3/2011 | Wallace et al. | |
| 2011/0112539 A1 | 5/2011 | Wallace et al. | |
| 2011/0160731 A1 | 6/2011 | Bleich et al. | |
| 2011/0190772 A1 | 8/2011 | Saadat | |
| 2011/0196257 A1 | 8/2011 | Schmitz et al. | |
| 2011/0224709 A1 | 9/2011 | Bleich | |
| 2011/0224710 A1 | 9/2011 | Bleich | |
| 2012/0022538 A1 | 1/2012 | Schmitz et al. | |
| 2012/0078255 A1 | 3/2012 | Bleich et al. | |
| 2012/0095468 A1 | 4/2012 | Wallace et al. | |
| 2012/0123294 A1 | 5/2012 | Sun et al. | |
| 2012/0143206 A1 | 6/2012 | Wallace et al. | |

FOREIGN PATENT DOCUMENTS

| | | |
|---|---|---|
| EP | 359883 A1 | 3/1990 |
| EP | 1304080 A2 | 4/2003 |
| EP | 1340467 A2 | 9/2003 |
| EP | 1207794 B1 | 5/2004 |
| EP | 1315463 B1 | 5/2005 |
| EP | 1611851 A1 | 1/2006 |
| EP | 1006885 B1 | 9/2006 |
| FR | 2706309 | 12/1994 |
| JP | 2960140 B2 | 10/1999 |
| JP | 23116868 | 4/2003 |
| JP | 24065380 A2 | 3/2004 |
| RU | 2107459 | 3/1998 |
| WO | WO92/22259 A2 | 12/1992 |
| WO | WO-96/22057 | 7/1996 |
| WO | WO97/14362 A1 | 4/1997 |
| WO | WO97/34536 A2 | 9/1997 |
| WO | WO99/18866 A1 | 4/1999 |
| WO | WO99/21500 A1 | 5/1999 |
| WO | WO00/67651 A1 | 11/2000 |
| WO | WO01/08571 A1 | 2/2001 |
| WO | WO01/62168 A2 | 8/2001 |
| WO | WO02/07901 A1 | 1/2002 |
| WO | WO02/34120 A2 | 5/2002 |
| WO | WO02/076311 A2 | 10/2002 |
| WO | WO03/026482 A2 | 4/2003 |
| WO | WO03/066147 A1 | 8/2003 |
| WO | WO2004/002331 A1 | 1/2004 |
| WO | WO2004/028351 A2 | 4/2004 |
| WO | WO2004/043272 A1 | 5/2004 |
| WO | WO2004/056267 A1 | 7/2004 |
| WO | WO2004/078066 A2 | 9/2004 |
| WO | WO2004/080316 A1 | 9/2004 |
| WO | WO2004/096080 A2 | 11/2004 |
| WO | WO2005/009300 A1 | 2/2005 |
| WO | WO2005/057467 A2 | 6/2005 |
| WO | WO2005/077282 A1 | 8/2005 |
| WO | WO2005/089433 A2 | 9/2005 |
| WO | WO2006/009705 A2 | 1/2006 |
| WO | WO2006/015302 A1 | 2/2006 |
| WO | WO2006/017507 A2 | 2/2006 |
| WO | WO2006/039279 A2 | 4/2006 |
| WO | WO2006/042206 A2 | 4/2006 |
| WO | WO2006/044727 A2 | 4/2006 |
| WO | WO2006/047598 A1 | 5/2006 |
| WO | WO2006/058079 A3 | 6/2006 |
| WO | WO2006/058195 A2 | 6/2006 |
| WO | WO2006/062555 A2 | 6/2006 |
| WO | WO2006/086241 A2 | 8/2006 |
| WO | WO2006/099285 A2 | 9/2006 |
| WO | WO2006/102085 A2 | 9/2006 |
| WO | WO2007/008709 A2 | 1/2007 |
| WO | WO2007/021588 A1 | 2/2007 |
| WO | WO2007/022194 A2 | 2/2007 |
| WO | WO2007/059343 A2 | 2/2007 |
| WO | WO2007/067632 A2 | 6/2007 |
| WO | WO2008/008898 A2 | 1/2008 |

OTHER PUBLICATIONS

Arcenio et al.; U.S. Appl. No. 12/980,165 entitled "Systems and Methods for Performing Spinal Fusion", filed Dec. 28, 2010.

Bleich et al.; U.S. Appl. No. 12/984,162 entitled "Devices and Methods for Tissue Access", filed Jan. 4, 2011.

Schmitz et al.; U.S. Appl. No. 12/917,253; entitled "Tissue Access Guidewire System and Method"; filed Nov. 1, 2010.

Wallace et al.; U.S. Appl. No. 12/911,537 entitled "Devices and Methods for Treating Tissue", filed Oct. 25, 2010.

Wallace et al.; U.S. Appl. No. 13/007,381 entitled "Tissue Modification Devices", filed Jan. 14, 2011.

Bleich et al.; U.S. Appl. No. 12/637,447 entitled "Devices and methods for tissue modification," filed Dec. 14, 2009.

Barer Malvin, "Instrument to Enhance Passage of the Gigli Saw," Journal of Pediatric Orthopedics, Raven Press, New York, 1984, 4:762-763.

Baumgart et al., "Indikation and Technik der Knochendurchtrennung," Der Chirurg, 1998, vol. 69:1188-1196. (in German with Eng Summary).

Bohinski et al., "Novel use of a threadwire saw for high sacral amputation," Journal of neurosurgery: Spine, 2005, vol. 3, 71R78.

Brunori et al., "Celebrating the centennial (1894-1994): Leonardo Gigli and his wire saw," J. Neurosurg, 1995, 82:1086-1090.

Burrows, Harold, "Surgical instruments and appliances used in operations," Faber and Faber, London, 1937, total pp. 4.

Codman Laminectomy Shaver (a Johnson & Johnson company www.codman.com) catalogue, pp. 416-431, [online] Retrieved from the internet: <URL: http:llwww.codman.com/PDFs/Catalog_04_R.pdf>.

Dammann, Gordon, Pictorial Encyclopedia of Civil War Medical Instruments and Equipment, Pictorial Histories Publishing Company, Missoula, Montana, 1983, Total pp. 2.

Edwards et al; "T-Saw Laminoplasty for the Management of Cervical Spondylotic Myelopathy," Spine, Lippincott Williams & Wilkins, Inc., 2000, vol. 25 (14): 1788R1794.

Ellman Int. Disc-FX System Accessories K052241 [online] Retrieved from the Internet: <URL: http://www.ellman.com/medical/>.

Eralp et al., "A comparison of two osteotomy techniques for tibial lengthening," Archives of orthopaedic and trauma surgery, 2004, vol. 124:298R300.

Fessler Richard G, "Minimally Invasive Microendoscopic Decompressive Laminotomy for Lumbar Stenosis," American Association of Neurological Surgeons, 2006, Online CME course, [Retrieved on Jun. 29, 2006 from the internet http://www.aans.emedtrain.com/lumbar_stenosis/lumbarStenosis.swf.

Fujita et al., "Chordoma in the Cervical Spine Managed with En Bloc Excision," Spine, Lippincott Williams & Wilkins, Inc., 1999, 24 (17), 1848-1851.

Goel, Atul, "Neurosurgical forum, Supraorbital Craniotomy," Journal of Neurosurgery, 1994, vol. 81, 642-643.

Gore Smoother User Manual, W. L. Gore & Associates, Inc. Flagstaff, AZ, Dec. 1999,Total pp. 3.

Hara et al., "En Bloc Laminoplasty Performed with Threadwire Saw: Technical Note," Neurosurgery, Jan. 2001, vol. 48, No. 1, pp. 235-239.

Hata et al; "A less invasive surgery for rotator cuff tear: Mini-open repair," Journal of Shoulder and Elbow Surgery, 2001, vol. 10 No. 1, 11-16.

Honl et al; "The Use of Water-Jetting Technology in Prostheses Revision Surgery R First Results of Parameter Studies on Bone and Bone Cement," J. Biomed Mater Res (Applied Biomaterials), John Wiley & Sons, Inc, 2000, 53, 6: 781-790.

Integra Ruggles TM Kerrison Rongeurs [online] Retrieved from the internet: <URL: http://www.integra-ls.com/products!?product=22>.

Jun, Byung-Yoon, "Posterior Lumbar Interbody Fusion With Restoration of Lamina and Facet Fusion," Spine, Lippincott Williams & Wilkins, Inc., 2000, vol. 25 No. 8, 917R922.
Kawahara et al., "Recapping T-Saw Laminoplasty for Spinal Cord Tumors," Spine, 1999, vol. 24 No. 13, pp. 1363-1370.
Martin-Benlloch et al., "Expansive Laminoplasty as a Method for Managing Cervical Multilevel Spondylotic Myelopathy," Spine, Lippincott Williams & Wilkins, Inc., 2003, vol. 28 No. 7, 680R684.
Miyamoto et al., "Kyphectomy Using a Surgical Threadwire (T-saw) for Kyphotic Deformity in a Child With Myelomeningocele," Spine, Lippincott Williams & Wilkins, Inc., 2003, vol. 28 No. 10, E187RE190.
Abdel-Wanis et al., "Tumor growth potential after tumoral and instrumental contamination: an in-vivo comparative study of T-saw, Gigli saw, and scalpel," Journal of orthopaedic science, 2001, vol. 6, 424R429.
Mopec Bone-Cutting tool, Product brochure, Total pp. 4.
Nakagiri et al., "Thoracoscopic Rib Resection Using a Gigli Saw," The Annals of Thoracic Surgery, 2005, vol. 80, 755R756.
Osaka et al., "Clinical significance of a wide excision policy for sacrococcygeal chordoma," J Cancer Res Clin Oncol, 2005, Total pp. 6.
Paley et al., "Percutaneous Osteotomies," Orthopedic Clinics of North America, 1991, vol. 22 No. 4, 613-624.
Pancoast, Joseph, "A Treatise on Operative Surgery," Carey and Hart, Philadelphia,1844, Total pp. 11.
Park et al; "Cases of the Excision of Carious Joints," John Scrymgeour, Glasgow, 1806, Total pp. 6.
Peavy et al., "Comparison of Cortical Bone Ablations by Using Infrared Laser Wavelengths 2.9 to 9.2 µm, Lasers in Surgery and Medicine," 1999, vol. 26, 421R434.
Peltier, Leonard Orthopedics: A History and Iconography, Norman Publishing, San Francisco, 1993, Total pp. 3.
Reckling Frederick, "Modified Stethoscope Earpiece Makes Excellent Gigli Saw Guide," J Bone and Joint Surgery Am, Dec. 1972, 54-A(8), 1787-1788.
Rutkow, Ira, "Surgery An Illustrated History," Mosby'Year Book, Inc., St. Louis, 1993, Total pp. 4.
Schwieger et al., "Abrasive Water Jet Cutting as a New Procedure for Cutting Cancellous Bone'ln Vitro Testing in Comparison with the Oscillating Saw," Wiley Interscience, www.interscience,wiley.com, Sep. 20, 2004, 223-228.
Sen, Cengiz, Tibia proksimalinde Gigli testeresi ile yapilanperkütan osteotominin güvenilirligi: Kadavra calismasi, Acta orthopaedica et traumatologica turcica, 2002, vol. 36, 136-140; (In Russian w/ Eng Summary).
Shiraishi et al., "Results of Skip Laminectomy—Minimum 2-Year Follow-up Study Compared With Open-Door Laminoplasty," Spine, Lippincott Williams & Wilkins, Inc., 2003, vol. 28 No. 24, 2667-2672.
Shiraishi T., "A new technique for exposure of the cervical spine laminae," Journal of neurosurgery. Spine, 2002, vol. 96(1), 122-126.
Shiraishi T., Skip laminectomy—a new treatment for cervical spondylotic myelopathy, preserving bilateral muscular attachments to the spinous processes: a preliminary report, Spine, 2002, vol. 2(2), 108-115.
Skippen et al., "The Chain Saw R A Scottish Invention," Scottish Medical Journal, 2004, vol. 49(2), 72-75.
Stevens et al., "Calvarial Bone Graft Harvest Using the Gigli Saw," Journal of Oral and Maxillofacial Surgery, 1998, vol. 56, 798-799.
Takada et al., "Unusual Metastasis to the Cauda Equina From Renal Cell Carcinoma," Spine, Lippincott Williams & Wilkins, Inc., 2003, vol. 28 No. 6, E114RE117.
Paktiss et al., "Afghan Percutaneous Osteotomy," Journal of Pediatric Orthopaedics, Raven Press Ltd, New York, 1993, vol. 13 No. 4, 531-533.
Tomita et al., "Expansive Midline T-Saw Laminoplasty (Modified Spinour Process-Splitting) for the Management of Cervical Myelopathy," Spine, Lippincott Williams & Wilkins, Inc, 1998, 23(1), 32-37.
Tomita et al., "The Threadwire Saw: a New Device for Cutting Bone," The Journal of Bone and Joint Surgery, 1996, vol. 78, 1915-1917.
Tomita et al., "The Use of the T-Saw for Expansive Midline laminoplasty in the Treatment of Cervical Myelopathy," Orthopedics and Traumatology, No. 3, pp. 169-178, 2002.
Tomita et al., "Total en bloc spondylectomy and circumspinal decompression for solitary spinal metastasis," Paraplegia, 1994, 32:36-46.
Tomita K. et al., "Total en bloc spondylectomy for solitary spinal metastases," International Orthopaedics (SICOT), 1994, 18: 291-298.
Truax, Charles, "The Mechanics of Surgery," Chicago, IL; 1899, Total pp. 3.
US Surgical Kerrison Spinal Rongeur K943116 [online] Retrieved from the Internet: <URL: http://www.ussurg.com/uss/index.html>.
Wilkins, Robert H, "Neurosurgical Classics," Johnson Reprint Corporation, New York, 1965, 377-382.
Zeppelin Laminectomy Rongeur K901372, [online] Retrieved from the internet: <URL: http://www.zeppelin-medical.com/download/instruments.pdf>.
Schmitz et al.; U.S. Appl. No. 12/352,385 entitled "Devices, methods and systems for neural localization," filed Jan. 12, 2009.
Bleich et al.; U.S. Appl. No. 12/352,978 entitled "Multiple pathways for spinal nerve root decompression from a single access point," filed Jan. 13, 2009.
Bleich et al.; U.S. Appl. No. 12/428,369 entitled "Devices and methods for tissue modification," filed Apr. 22, 2009.
Schmitz et al.; U.S. Appl. No. 12/496,094 entitled "Access and tissue modification systems and methods," filed Jul. 1, 2009.
Garabedian et al.; U.S. Appl. No. 12/824,043; entitled "Surgical Tools for Treatment of Spinal Stenosis"; filed Jun. 25, 2010.
Schmitz et al.; U.S. Appl. No. 12/816,729 entitled Access and Tissue Modification Systems and Methods, filed Jun. 16, 2010.
Wallace et al.; U.S. Appl. No. 12/724,315 entitled "Flexible Neural Localization Devices and Methods," filed Mar. 15, 2010.
Wallace et al.; U.S. Appl. No. 12/773,595 entitled "Tissue Modification Devices and Methods," filed May 4, 2010.
Bleich et al.; U.S. Appl. No. 13/112,886 entitled "Methods, Systems and Devices for Carpal Tunnel Release", filed May 20, 2011.
Bleich et al.; U.S. Appl. No. 13/112,918 entitled "Methods, Systems and Devices for Carpal Tunnel Release", filed May 20, 2011.
US Surgical Kerrison Spinal Rongeur K943116 [online] Retrieved from the internet: <URL: http://www.ussurg.com/uss/index/html>, Jul. 27, 1994.
Zeppelin Laminectomy Rongeur K901372, [online] Retrieved from the internet: <URL: http://www.zeppelin-medical.com/download/instruments.pdf>. Oct. 24, 2006.
Ellman Int. Disc-FX System Accessories K052241 [online] Retrieved from the Internet: <URL: http://www.ellman.com/ medical/ >. Feb. 27, 2006.
Bartol et al., "Arthroscopic Microscopic Discectomy in Awake Patients: The Effectiveness of Local/Neuroletp Anaesthetic," Canadian Spine Society Meeting, Vernon BC, Canada, Mar. 2002.
Bartol et al., "Use of Neve Stimulator to Localize the Spinal Nerce Root During Arthroscopic Discectomy Procedures," Canadian Spine Society Meeting, Vernon BC, Canada, Mar. 2002.
Ohta et al., "Superimposed Mechanomygraphic Response at Different Contraction Intensity in Medial Gastrocnemius and Soleus Muscles," International Journal of Sport and Health Science: vol. 5, 63-70, 2007.
Schwieger et al., "Abrasive Water Jet Cutting as a New Procedure for Cutting Cancellous Bone—In Vitro Testing in Comparison with the Oscillating Saw," Wiley Interscience, www.interscience.wiley.com, Sep. 20, 2004, 223-228.
Mopec Bone-Cutting tool, Product brocure, Total pp. 4. First accessed Dec. 15, 2005.
Codman Laboratory Shaver (a Johnson & Johnson company www.codman.com) catalogue, pp. 416-431, [online] Retrieved from the internet: <URL: http:llwww.codman.com/PDFs/Catalog_04_R.pdf >. First accessed Oct. 24, 2006.
Integra Ruggles TM Kerrison Rongeurs [online] Retrieved from the internet: <URL: http://www.integra-ls.com/products!? product=22>. First accessed Oct. 24, 2006.
Herkowitz, , "The Cervical Spine Surgery Atlas", Herkowitz, *"The Cervical Spine Surgery Atlas"*, 2004, 2nd Edition Jan. 1, 2004 , 203-206, 208.

Bleich et al.; U.S. Appl. No. 13/484,744 entitled "Devices and Methods for Tissue Modification," filed May 31, 2012.
Bleich et al.; U.S. Appl. No. 13/430,500 entitled "Devices and Methods for Tissue Modification," filed Mar. 26, 2012.

Garabedian et al.; U.S. Appl. No. 13/437,214 entitled "Flexible Tissue Rasp," filed Apr. 2, 2012.

* cited by examiner

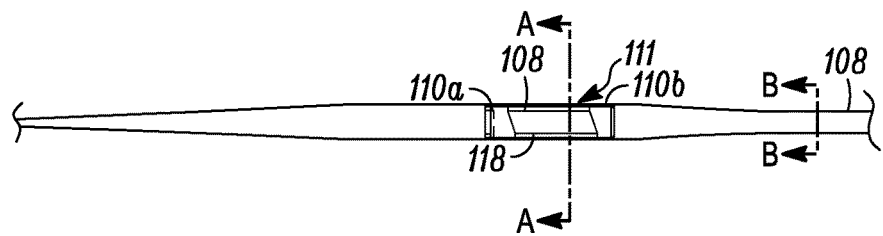
FIG. 3C
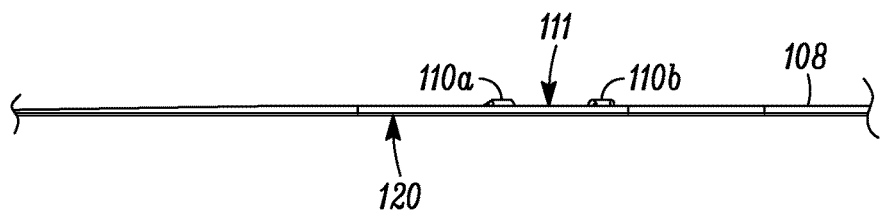
FIG. 3D
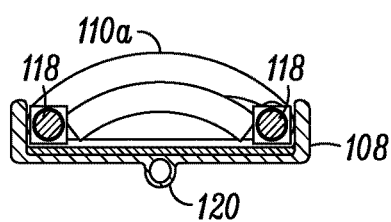 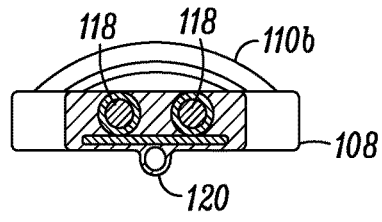
FIG. 3E  FIG. 3F

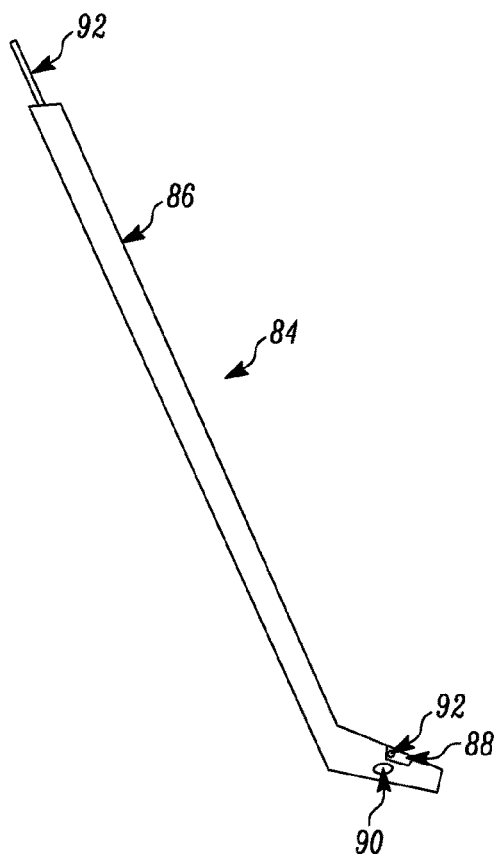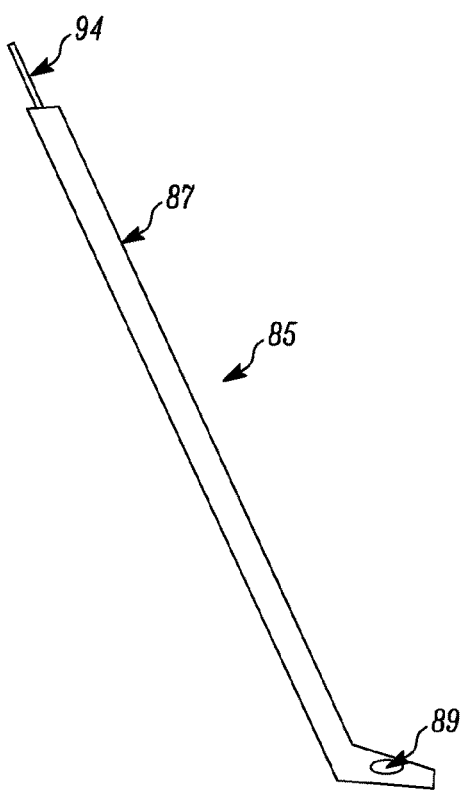
*FIG. 10A*  *FIG. 10B*

SECTION A-A

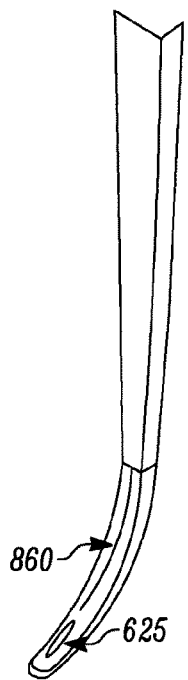
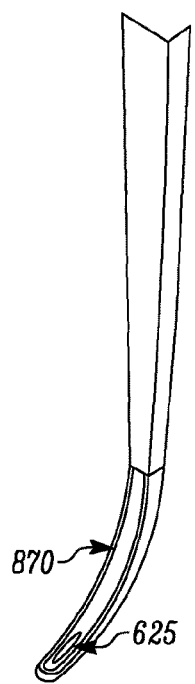
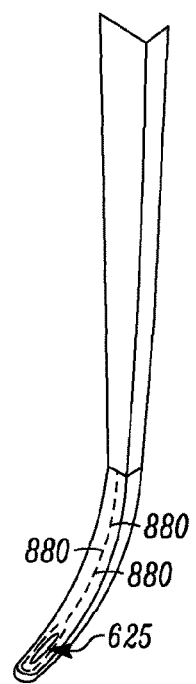
FIG. 17A  FIG. 17B  FIG. 17C
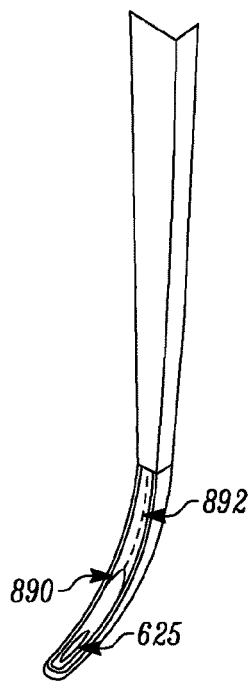
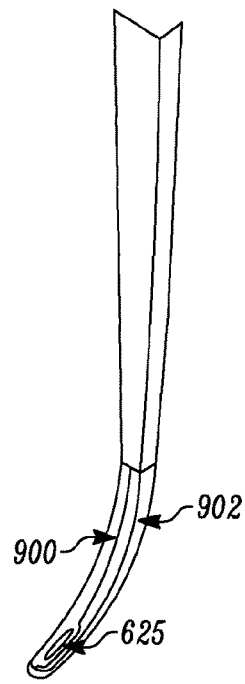
FIG. 17D  FIG. 17E

SECTION C-C

SECTION A-A

SECTION B-B

SPINAL ACCESS AND NEURAL LOCALIZATION

CROSS REFERENCE TO RELATED APPLICATIONS

This application is a divisional of U.S. patent application Ser. No. 11/457,416, filed on Jul. 13, 2006 entitled "SPINAL ACCESS AND NEURAL LOCALIZATION", which is a continuation-in-part of U.S. patent application Ser. No. 11/251,205, filed on Oct. 15, 2005 entitled "DEVICES AND METHODS FOR TISSUE ACCESS", which claims the benefit of U.S. Provisional Patent Application No. 60/681,864, filed on May 16, 2005, entitled "METHOD AND APPARATUS FOR SELECTIVE SURGICAL REMOVAL OF TISSUE" and is also a continuation-in-part of U.S. patent application Ser. No. 11/375,265, filed on Mar. 13, 2006, entitled "METHODS AND APPARATUS FOR TISSUE MODIFICATION". The entire disclosures of all of the above applications are hereby incorporated by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

The present invention relates to methods and apparatus for modifying tissue in a patient.

Many pathological conditions in the human body may be caused by enlargement, movement, displacement and/or a variety of other changes of bodily tissue, causing the tissue to press against (or "impinge on") one or more otherwise normal tissues or organs. For example, a cancerous tumor may press against an adjacent organ and adversely affect the functioning and/or the health of that organ. In other cases, bony growths (or "bone spurs"), arthritic changes in bone and/or soft tissue, redundant soft tissue, or other hypertrophic bone or soft tissue conditions may impinge on nearby nerve and/or vascular tissues and compromise functioning of one or more nerves, reduce blood flow through a blood vessel, or both. Other examples of tissues which may grow or move to press against adjacent tissues include ligaments, tendons, cysts, cartilage, scar tissue, blood vessels, adipose tissue, tumor, hematoma, and inflammatory tissue.

One specific example of a condition caused by tissue impingement is spinal stenosis. Spinal stenosis occurs when neural tissue and/or vascular tissue in the spine become impinged by one or more structures pressing against them ("neural and/or neurovascular impingement"), causing one or more symptoms. This impingement of tissue may occur in one or more of several different areas in the spine, such as in the central spinal canal (the vertical passage through which the spinal cord and cauda equina extends), the lateral recesses of the spinal canal, or one or more intervertebral foramina (the openings through which nerve roots branching from the spinal cord pass).

For explanatory purposes, FIG. 1 is offered to show an approximate top view of a vertebra (one of the bones of the spinal column) with the cauda equina (the horsetail-shaped bundle of nerves that extends from the base of the spinal cord through the central spinal canal) shown in cross section and two nerve roots exiting the central spinal canal and extending through intervertebral foramina on either side of the vertebra. (FIG. 1 is not drawn to exact scale and is intended for exemplary purposes only. It should be emphasized here that the drawing figures appended to this application are not intended to be precisely anatomically correct and are provided for exemplary purposes to facilitate description.) The spinal cord and cauda equina run vertically along the spine through the central spinal canal, while nerve roots branch off of the spinal cord and cauda equina between adjacent vertebrae and extend through the intervertebral foramina.

One common cause of spinal stenosis is buckling and thickening of the ligamentum flavum (one of the ligaments attached to and connecting the vertebrae), as shown in FIG. 1. Buckling or thickening of the ligamentum flavum may impinge on one or more neurovascular structures, dorsal root ganglia, nerve roots and/or the spinal cord itself. Another common cause of neural and neurovascular compression within the spine is disease of one or more of the intervertebral discs (the malleable discs between adjacent vertebrae), which may lead to collapse, bulging or herniation of the disc. In FIG. 1, an intervertebral disc is shown with three solid-tipped arrows demonstrating how the disc might bulge or herniate into the central spinal canal to impinge upon the spinal cord, cauda equina and/or individual nerve roots. Other causes of neural and neurovascular impingement in the spine include: hypertrophy of one or more facet joints (also known as zygopophaseal joints, facet joints provide articulation between adjacent vertebrae—two vertebral facet superior articular processes are shown in FIG. 1); formation of osteophytes (bony growths or "bone spurs") on vertebrae; spondylolisthesis (sliding of one vertebra relative to an adjacent vertebra); and (facet joint) synovial cysts. Disc, bone, ligament or other tissue may impinge on the spinal cord, the cauda equina, branching spinal nerves and/or blood vessels in the spine to cause loss of function, ischemia (shortage of blood supply) and even permanent damage of neural or neurovascular tissue. In a patient, this may manifest as pain, impaired sensation and/or loss of strength or mobility.

In the United States, spinal stenosis occurs with an incidence of between 4% and 6% of adults aged 50 and older and is the most frequent reason cited for back surgery in patients aged 60 and older. Conservative approaches to the treatment of symptoms of spinal stensosis include systemic medications and physical therapy. Epidural steroid injections may also be utilized, but they do not provide long lasting benefits. When these approaches are inadequate, current treatment for spinal stenosis is generally limited to invasive surgical procedures to remove vertebral ligament, cartilage, bone spurs, synovial cysts, cartilage, and bone to provide increased room for neural and neurovascular tissue. The standard surgical procedure for spinal stenosis treatment includes laminectomy (complete removal of the lamina (see FIG. 1) of one or more vertebrae) or laminotomy (partial removal of the lamina), followed by removal (or "resection") of the ligamentum flavum. In addition, the surgery often includes partial or occasionally complete facetectomy (removal of all or part of one or more facet joints between vertebrae). In cases where a bulging intervertebral disc contributes to neural impingement, disc material may be removed surgically in a discectomy procedure.

Removal of vertebral bone, as occurs in laminectomy and facetectomy, often leaves the effected area of the spine very unstable, leading to a need for an additional highly invasive fusion procedure that puts extra demands on the patient's vertebrae and limits the patient's ability to move. In a spinal fusion procedure, the vertebrae are attached together with some kind of support mechanism to prevent them from moving relative to one another and to allow adjacent vertebral bones to fuse together. Unfortunately, a surgical spine fusion results in a loss of ability to move the fused section of the back, diminishing the patient's range of motion and causing stress on the discs and facet joints of adjacent vertebral segments. Such stress on adjacent vertebrae often leads to further dysfunction of the spine, back pain, lower leg weakness or pain, and/or other symptoms. Thus, while laminectomy, facetectomy, discectomy, and spinal fusion frequently improve symptoms of neural and neurovascular impingement in the short term, these procedures are highly invasive, diminish spinal function, drastically disrupt normal anatomy, and increase long-term morbidity above levels seen in untreated patients.

Therefore, it would be desirable to have less invasive methods and devices for addressing neural and neurovascular impingement in a spine. Ideally, methods and devices for addressing impingement in spine would treat one or more target tissues while preventing unwanted effects on adjacent or nearby non-target tissues. Also ideally, such methods and devices would be minimally invasive and reduce impingement without removing significant amounts of vertebral bone, joint, or other spinal support structures, thereby avoiding the need for spinal fusion and, ideally, reducing the long-term morbidity levels resulting from currently available surgical treatments. It may also be advantageous to have less invasive methods and devices for modifying target tissues in parts of the body other than the spine while preventing modification of non-target tissues.

One challenge in developing less invasive or less damaging devices and techniques for treating neural and neurovascular impingement is reducing the risk of any unwanted damage to nerve or vascular tissue. This challenge may prove daunting, because the tissue impinging on neural or neurovascular tissue in the spine is typically located in small, confined areas, such as intervertebral foramina, the central spinal canal and the lateral recesses of the central spinal canal, which typically have very little open space and are difficult to see without removing spinal bone. Thus, it would be highly desirable to have methods and devices to facilitate placement of a tissue modification device in a desired location in the spine for performing a tissue modification procedure while preventing unwanted damage to surrounding tissues. Ideally, such methods and devices would allow a physician performing a tissue modification procedure to know where neural tissue and non-neural tissue was located relative to a tissue modification device, to help assure safety of the procedure. At least some of these objectives will be met by the present invention.

2. Description of Background Art

Flexible wire saws and chain saws, such as threadwire saws (T-saws) and Gigli saws, have been used since the late 1800s to saw through or file/abrade bone and other tissue in the human body. See, for example, Brunori A et al., "Celebrating the Centenial (1894-1994): Leonardo Gigli and His Wire Saw," J Neurosurg 82:1086-1090, 1995. An example of one such saw is described in U.S. Pat. No. 8250, issued to P. A. Stohlmann on Nov. 28, 1876. A description of using a T-saw to cut vertebral bone is provided in Kawahara N et al., "Recapping T-Saw Laminoplasty for Spinal Cord Tumors," SPINE Volume 24, Number 13, pp. 1363-1370.

A method and apparatus for treating spinal stenosis is described in PCT Patent Application Pub. No. WO 01/08571. A surgical instrument for removing cartilage from a knee cavity is described in U.S. Pat. No. 3,835,859. Various devices for stimulating or locating nerve tissue are described in U.S. Pat. Nos. 4,962,766, 5,284,154, 6,146,380, 6,466,817, 6,500,128, 6,564,078 and 6,760,616 and U.S. Patent Application Pub. Nos. 2004/0199084 and 2005/0182454.

SUMMARY OF THE INVENTION

In various embodiments, the present invention provides methods, apparatus and systems for modifying tissue in a patient. Generally, the methods, apparatus and systems may involve using an elongate, at least partially flexible tissue modification device having one or more tissue modification members to modify one or more target tissues. The tissue modification device may be configured such that when the tissue modification member (or members) is in a position for modifying target tissue, one or more sides, surfaces or portions of the tissue modification device configured to avoid or prevent damage to non-target tissue will face non-target tissue. In various embodiments, during a tissue modification procedure, anchoring or tensioning forces may be applied at or near either or both of a distal portion and a proximal portion of the tissue modification device, either inside or outside the patient, to urge the tissue modifying member(s) against target tissue. When anchoring force is applied to one end of a device, for example, pulling or tensioning force may be applied to the unanchored end of the device. In some embodiments, tensioning force may be applied at or near both ends of a device.

When the tissue modifying members of a tissue modification device are in contact with target tissue, they may then be activated to modify target tissue while avoiding damage to surrounding, non-target tissues. In various embodiments, various alternative means may be employed for avoiding such unwanted damage. For example, in some embodiments, the tissue modifying members may be generally disposed along a length of the tissue modification device that approximates a length of target tissue to be modified. In some embodiments, tissue is modified without moving the tissue modification members significantly beyond the target tissue. Applying tensioning or anchoring forces at or near the proximal and distal portions of an at least partially flexible tissue modification device may enhance the ability of the device's tissue modification members to work effectively within a limited treatment space and may also allow the device to have a relatively small profile, thus facilitating its use in less invasive procedures and in other procedures in which alternative approaches to target tissue may be advantageous.

As used above and throughout the present application, the phrase "applying an anchoring force" means applying a force to maintain a portion of a device, or a device as a whole, substantially stable or motion-free. Applying an anchoring force, therefore, is not limited to preventing all movement of a device, and in fact, a device to which an anchoring force is applied may actually move in one or more directions in some embodiments. In other embodiments, an anchoring force is applied to maintain a portion of a device substantially stable, while another portion of the device is allowed to move more freely. As will be described in further detail below, applying an anchoring force in one embodiment involves a user of a device grasping the device at or near one of its ends, typically though not necessarily by use of a handle. In other embodiments, devices may use one or more anchoring members to apply an anchoring force. In a number of embodiments, an anchoring force may be applied with or against one or more tissues of a patient's body, and the tissue(s) may often move even as they apply (or help apply) the force. Thus, again, applying an anchoring force to a device does not necessarily mean that all motion of the device is eliminated. Of course, in some embodiments, it may be possible and desirable to eliminate all movement or substantially all movement of a device (or portion of a device), and in some embodiments anchoring force may be used to do so.

In some embodiments, the described methods, apparatus and systems may be used to modify tissue in a spine, such as for treating neural impingement, neurovascular impingement and/or spinal stenosis. In alternative embodiments, target tissues in other parts of the body may be modified.

In one aspect of the present invention, a method for locating neural tissue in a patient body may involve: advancing a probe along a natural tissue interface between the neural tissue and another tissue in the body, the probe having a first surface oriented toward the neural tissue and a second surface oriented away from the neural tissue; delivering a first electrical current to a first electrode along the first surface of the probe; delivering a second electrical current to a second electrode along the second surface of the probe; and verifying that the first surface of the advanced probe remains oriented toward the neural tissue and the second surface remains oriented away from the neural tissue by monitoring neural response to the first and second electrical currents. In some embodiments, the probe may include an elongate flattened body having an axis and a distal end, the first and second surfaces comprising opposed major surfaces of the elongate body, the electrodes extending along an electrode length proximally of the distal end sufficiently to verify that injury to the neural tissue will be inhibited when treatment of the other tissue is directed along the electrode length from a path of the probe. Optionally, the tissue interface may include two adjacent tissue planes, and advancing the probe may cause the distal end of the probe to dissect the neural tissue from the other tissue along the tissue interface, the other tissue comprising an impinging tissue and being harder than the neural tissue. The method may optionally also involve treating the other tissue by directing treatment from the probe path along the electrode length in the verified orientation of the second electrode so as to reduce impingement of the neural tissue by the other tissue.

In some embodiments, advancing the probe involves advancing a distal portion of the probe along an interface between a bone or ligament surface and a soft tissue surface so that at least a part of the distal portion of the advanced probe extends into an intervertebral foramen of a spine. Optionally, the method may further include advancing a curved, shape-memory guide member having at least one lumen out of a distal opening on the probe device.

In some embodiments, the method may involve: determining a first threshold amount of electrical current required to stimulate measurable action potentials in the neural tissue via the first electrode; determining a second threshold amount of electrical current required to stimulate measurable action potentials in the neural tissue via the second electrode; and comparing the first and second threshold amounts of current, to determine which of the first and second surfaces is closest to the neural tissue. For example, in some embodiments, the threshold amount of current applied to the electrode closest to the neural tissue may be less than about 1 milliamp, and the amount of threshold current applied to the electrode farthest from the neural tissue may be greater than about 2 milliamps. In some embodiments, comparing the first and second threshold amounts of current may involve calculating a ratio of the threshold amount of current applied to the electrode farthest from the neural tissue compared to the threshold amount of current applied to the electrode closest to the neural tissue. For example, in some cases such a ratio may be greater than or equal to 2.

In some embodiments, monitoring the neural response to the first and second currents comprises monitoring somatosensory evoked potentials (SSEP), motor evoked potentials (MEP), electromyography (EMG), visible muscle twitch and/or tactile muscle twitch.

In another aspect of the present invention, a method for positioning a guidewire between neural tissue and adjacent tissue in a patient body involves: positioning a distal portion of a probe device between neural tissue and tissue adjacent the neural tissue in the body; delivering electrical current to a first electrode coupled with a first surface of the distal portion of the probe; determining a first threshold amount of electrical current required to provoke a response in the neural tissue via the first electrode; determining a location of the neural tissue relative to the first surface of the distal portion, based on the first threshold amount of current; and advancing a guidewire through an opening in the distal portion of the probe. Some embodiments may further involve, before advancing the guidewire through the opening, delivering electrical current to a second electrode coupled with a second surface of the distal portion; determining a second threshold amount of electrical current required to provoke a response in the neural tissue via the second electrode; and comparing the first and second threshold amounts of current, to determine which of the first and second surfaces is closest to the neural tissue.

In some embodiments, positioning the distal portion may involve positioning at least part of the distal portion in an intervertebral foramen of a spine. In some embodiments, positioning the distal portion may involve advancing a shaped portion of the probe along a complementary shaped portion of a decompression implant located between two vertebrae of the spine. In some embodiments, positioning the distal portion may involve advancing a shaped portion of the probe through a complementary shaped portion of a tubular spinal access conduit. In some embodiments, positioning the distal portion may involve advancing a curved, shape-memory guide member having at least one lumen out of a distal opening on the probe device. For example, advancing the guide member may involve pushing a slide member coupled with the guide member and disposed on a shaft of the probe. Advancing the guidewire may also involve advancing through the lumen of the guide member. In some embodiments, advancing the guidewire at least partially straightens the curved guide member.

In some embodiments, positioning the distal portion involves articulating at least part of the distal portion. Advancing the guidewire may involve advancing a sharp-tipped guidewire through the distal opening and then through tissue in the body. The method may optionally further include removing the probe device from the body while leaving the guidewire in place between the neural tissue and adjacent tissue. Such embodiments may optionally further include advancing at least one tissue modification device over the guidewire to position a portion of the device between the neural tissue and adjacent tissue and performing a tissue modifying procedure with the tissue modification device. An alternative embodiment may involve coupling a distal portion of a tissue modification device at or near one end of the guidewire, pulling the guidewire to pull a portion of the tissue modification device to a desired position between the neural tissue and adjacent tissue, and performing a tissue modifying procedure with the tissue modification device. Either of these last method embodiments may also optionally include delivering electrical current to at least one electrode coupled with the tissue modification device to confirm a location of the neural tissue relative to the device.

In another aspect of the present invention, a device for advancing a guidewire in a human body may include: an elongate probe having a proximal portion, a distal portion and at least one lumen having a proximal opening and a distal opening; a curved guide member slidably disposed within the lumen of the probe, wherein at least a portion of the guide member is configured to be advanced out of the distal opening of the lumen to assume a curved shape, and wherein the guide member includes at least one guidewire lumen; and a slide member coupled with the probe and the guide member to advance the guide member out of the distal opening of the probe. In some embodiments, the device may further include at least one signal transmitter coupled with at least one of the probe and the guide member and connectible with at least one energy source. For example, in one embodiment, the at least one signal transmitter may include a first electrode coupled with a first surface of the probe at or near the distal portion and connectible with the at least one energy source and at least a second electrode coupled with a second surface of the probe at or near the distal portion and connectible with the energy source. Various alternative embodiments may additionally include a third electrode, fourth electrode or more on various surfaces. In another alternative embodiment, the at least one signal transmitter may include at least one tissue distinguishing member selected from the group consisting of ultrasound transducers, piezoelectric transducers, visualization devices and optical coherence tomography devices.

In some embodiments, the elongate probe may include a curve or bend at or near the distal portion. For example, such a curve or bend and the distal portion may be configured to facilitate passage of at least part of the distal portion into an intervertebral foramen of a spine. In alternative embodiments, the probe may be predominantly rigid, at least part of the probe may flexible, and/or at least part of the distal portion of the probe may be articulated to form more than one curved shape. In one articulating embodiment, the device may include at least one wire coupled with the distal portion for pushing or pulling to articulate the distal portion.

In one embodiment, the probe may include at least two lumens, wherein one lumen is configured to accept the guide member and the other lumen(s) comprise at least one of a visualization lumen, a suction lumen and a fluid introduction lumen. Such an embodiment may optionally further include a visualization device disposed in the visualization lumen, such as but not limited to an endoscope, fiber optic, charge-coupled device (CCD) or complementary metal-oxide semiconductor (CMOS) device.

In some embodiments, the proximal opening of the probe lumen may be sized to allow passage of a guidewire, so that the guidewire may be passed into the proximal opening, into the guidewire lumen of guide member, and out a distal opening of the guide member. Also in some embodiments, at least a portion of the probe may be shaped to slide along a complementary shaped portion of a spinal decompression implant located between two vertebrae or to slide through a complementary shaped portion of a tubular spinal access conduit.

In various embodiments, the guide member may have a cross-sectional shape such as but not limited to round, oval, rectangular, triangular, elliptical and figure-8. In some embodiments, the guide member may include a shape memory material. In some embodiments, the guide member may be sufficiently flexible that when a guidewire is passed through its lumen, the guide member at least partially straightens.

In another aspect of the present invention, a system for localizing neural tissue in a patient body, the neural tissue being separated from an impinging tissue by a natural tissue interface, may include: a probe having a proximal end and a distal end with an axis therebetween, the distal end suitable for advancing distally along the natural tissue interface, the probe having first and second laterally oriented surfaces; a first signal transmitter disposed along the first surface of the probe; a second signal transmitter disposed along the second surface of the probe, the first and second signal transmitters defining an axial verification length; and a signal source for generating a neural localization signal, the source selectively coupleable with the first and second signal transmitters of the probe such that, by monitoring a response to the neural localization signal when the probe has been advanced along the natural interface with the first surface oriented toward the neural tissue and the second surface oriented away from the neural tissue, orientation of the neural tissue relative to the probe axis throughout the axial verification length can be safely verified.

In one embodiment, the first and second signal transmitters may comprise first and second electrodes, the signal source comprising an electrical source for generating electrical neural stimulation signals. Optionally, such a system may further include: a neural response sensor; and a processor coupled to the electrical source and the sensor, the processor configured to verify, in response to the neural response to the stimulation applied by the first electrode and the second electrode, that the first surface is oriented toward the neural tissue and the second electrode is oriented away from the neural tissue. In an alternative embodiment, the first and second signal transmitters may comprise first and second ultrasound transducers, the signal source comprising an ultrasound generator.

In some embodiments, the distal portion of the shaft is configured to facilitate its passage into an intervertebral foramen of a spine. Optionally, in such embodiments, at least a portion of the shaft of the probe may be shaped to slide along a complementary shaped portion of a spinal decompression implant located between two vertebrae. Such a system may further include at least one spinal decompression implant for placing between two vertebrae. In another embodiment, at least a portion of the shaft of the probe may be shaped to slide through a complementary shaped portion of a tubular spinal access conduit. Such a system may optionally further include at least one tubular spinal access conduit for gaining access to the spine through the body.

Various additional features may be included in alternative embodiments of the system. For example, in one embodiment, the system may further include at least one of an ultrasound transducer, a piezoelectric crystal, a visualization device, and an optical coherence tomography device coupled with the probe. In some embodiments, the probe may further comprise at least one lumen disposed longitudinally through at least a portion of its length, the system further comprising a curved, hollow guide member slidably disposed within, and configured to be advanced out of a distal opening of, the probe lumen, wherein the guide member comprises at least one guidewire lumen. Such an embodiment may optionally further include a slide member coupled with the probe and the guide member to advance the guide member out the distal opening of the probe. In one embodiment, the system may further include a guidewire and at least one tissue removal device for advancing along or being pulled into position by the guidewire to remove tissue from the body. As another optional feature, in one embodiment the system may further include at least one sizing probe configured to perform at least one of the functions of assessing an amount of space between tissues before advancing the probe, increasing the amount of space between tissue before advancing the probe, and assessing the amount of space between tissues after performing a tissue modification procedure.

These and other aspects and embodiments are described more fully below in the Detailed Description, with reference to the attached Drawings.

BRIEF DESCRIPTION OF THE DRAWINGS

FIG. 3C is a top view of the portion shown in FIG. 3B;

FIG. 3D is a side view of the portion shown in FIGS. 3B and 3C;

FIGS. 3E and 3F are cross-sectional views of a portion of the tissue modification device taken through lines A-A and B-B, respectively, shown in FIG. 3C;

FIGS. 10A and 10B are side views of two access probe devices according to alternative embodiments of the present invention;

FIGS. 17A-17E are perspective views of distal portions of various embodiments of a probe device, demonstrating different numbers and configurations of electrodes according to various embodiments of the present invention;

DETAILED DESCRIPTION OF THE INVENTION

Methods, apparatus and systems for modifying tissue in a patient are provided. Methods, apparatus and systems for spinal access and neural localization are also provided. Although the following description and accompanying drawing figures generally focus on tissue modification in spine, in various alternative embodiments any of a number of tissues in any of a number of anatomical locations in a patient may be modified.

Figure 1:
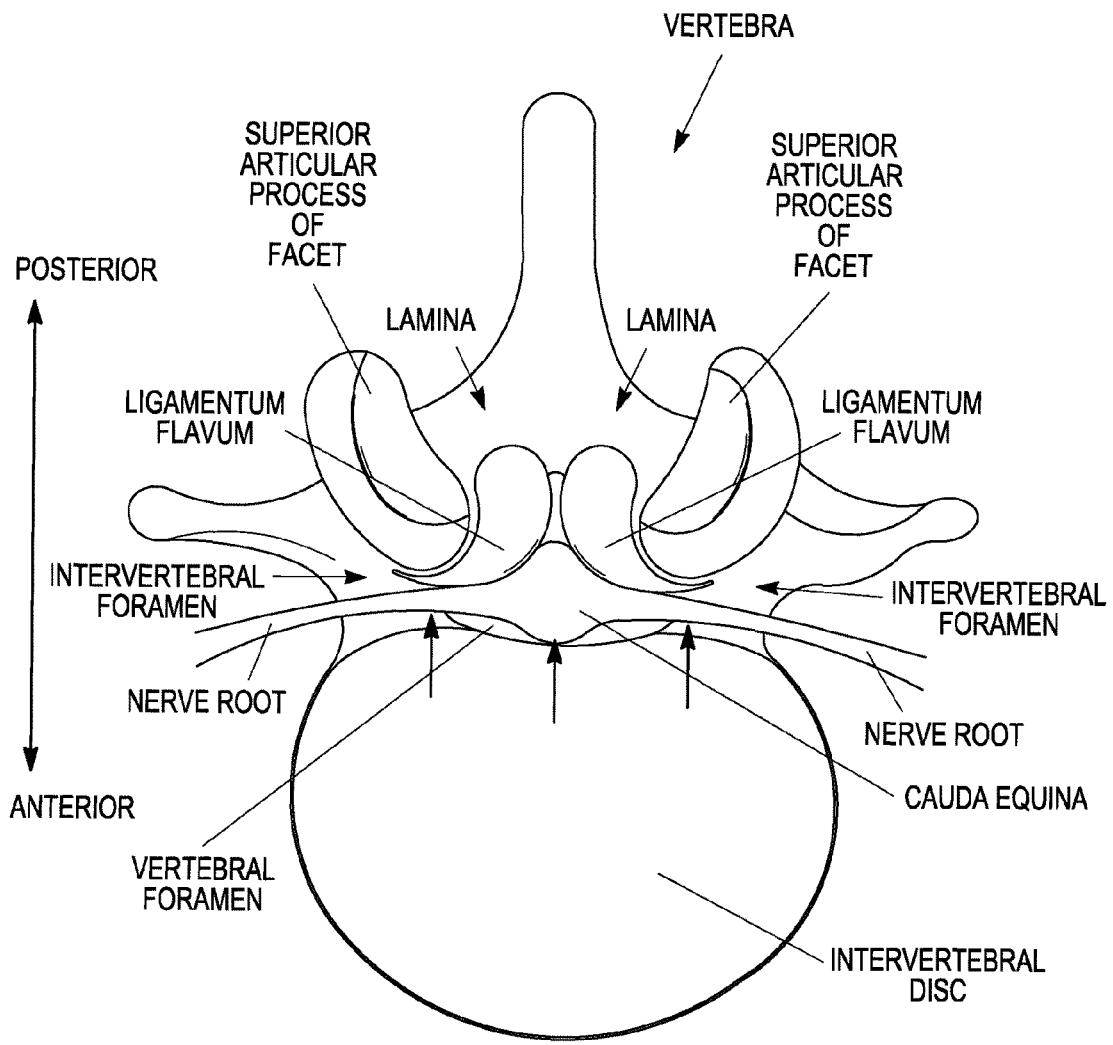
FIG. 1 is cross-sectional view of a spine, showing a top view of a lumbar vertebra, a cross-sectional view of the cauda equina, and two exiting nerve roots.
Figure 2:
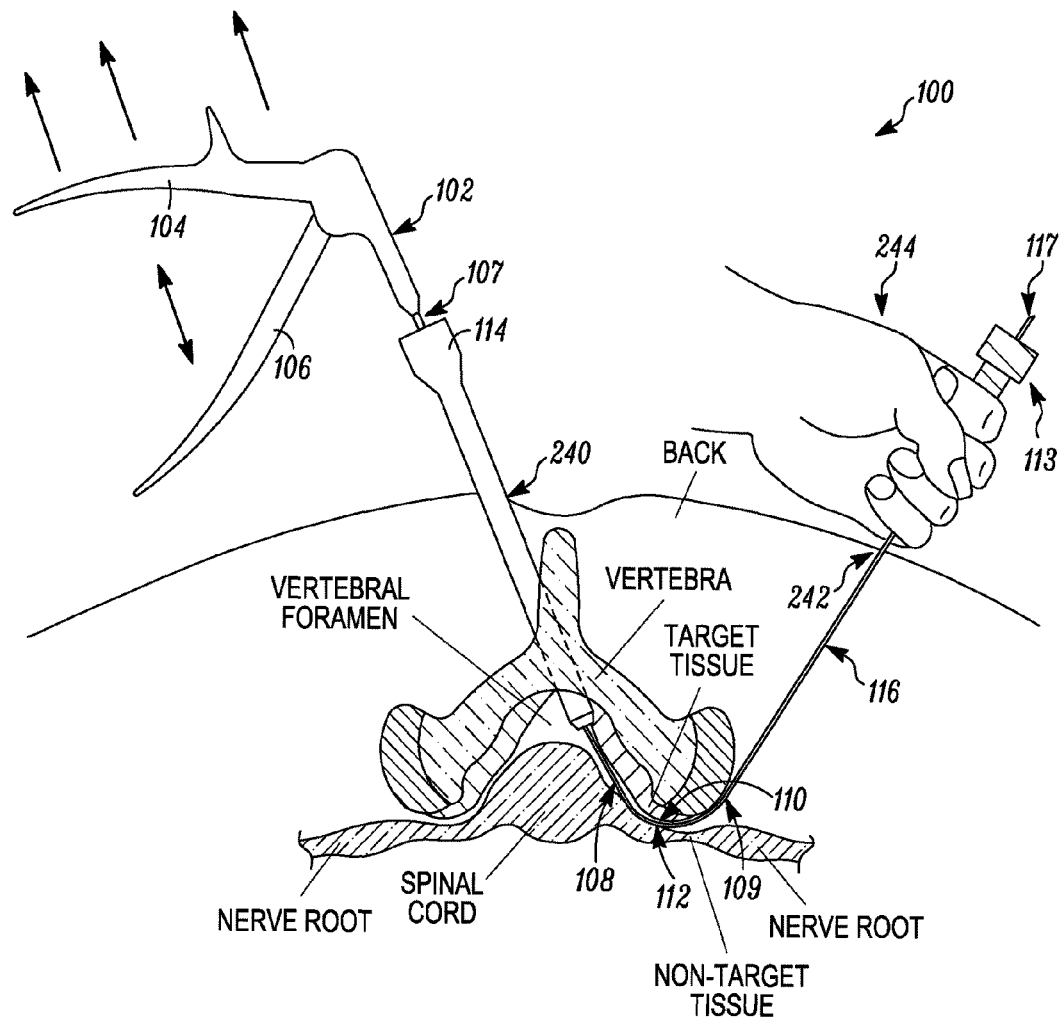
FIG. 2 is a cross-sectional view of a portion of a patient's back and spine, showing part of a vertebra and apparatus in place for modifying tissue according to one embodiment of the present invention.

Referring to FIG. 2, one embodiment of a tissue modification device 102 may include an elongate body 108 having a proximal portion 107 and a distal portion 109, a proximal handle 104 with an actuator 106 coupled with proximal portion 107, one or more tissue modifying surfaces or members 110, one or more tissue protective surfaces 112, a guidewire 116 coupled with the distal portion 109, and a distal handle 113 removably couplable with guidewire 116. (FIG. 2, as well as many of the subsequent Figures in this application, is not drawn to scale.) In various embodiments, some of which are described further below, modification device 102 may be introduced into an area for performing a treatment, such as a spine, using any of a number of different introduction methods, devices and systems. In FIG. 2, for example, modification device 102 extends through an introducer device 114 placed through a first incision 240 on the patient's back and into the central spinal canal. Modification device 102 may be advanced through introducer 114, in one embodiment, by coupling distal portion 109 with guidewire 116 and pulling distal portion 109 through introducer 114 by pulling guidewire 116. Distal portion 109 may be further pulled into or through an intervertebral foramen between two adjacent vertebrae (only part of one vertebra is shown in FIG. 2), and out a second (or "distal") incision or non-incision exit point 242 on the back. When guidewire 116 is advanced through distal exit point 242, it may be coupled with distal handle 113 to facilitate application of anchoring or tensioning force to guidewire 116. In some embodiments, as shown, guidewire 116 may include a beveled distal tip 117 for facilitating advancement of guidewire 116 through tissue. In an alternative embodiment, a modification device may be advanced along a guidewire extending through an introducer, rather than pulling the modification device through the introducer. In another alternative embodiment, a tissue modification device may be advanced into the spine through an open surgical approach. These and other methods for introducing a tissue modification device are described in further detail below.

Generally, tissue modification device 102 may be advanced to a position in the spine such that tissue modifying surface or member 110 faces target tissue to be modified, such as buckled, thickened or otherwise impinging ligamentum flavum tissue as shown in FIG. 2. Modification device 102 is configured such that when tissue modifying member 110 faces target tissue, protective surface(s) 112 face non-target tissue. Protective surface 112 may be simply a length of elongate body 108 or may have one or more protective features, such as a widened diameter, protective or lubricious coating, extendable or expandable barrier, drug-eluting coating or ports, or the like. In some instances, protective surface(s) 112 may act as "non-tissue-modifying" surfaces, in that they may not substantially modify the non-target tissue. In alternative embodiments, protective surface(s) 112 may affect non-target tissue by protecting it in some active way, such as by administering one or more protective drugs, applying one or more forms of energy, providing a physical barrier, or the like.

In some embodiments, once tissue modification device 102 is positioned such that tissue modifying surface or member 110 faces target tissue and protective surface 112 faces non-target tissue, an anchoring or tensioning force may be applied to distal portion 109 of elongate body 108 by applying anchoring or tensioning force to guidewire 116 via distal handle 113. Anchoring or tensioning force may also be applied at or near proximal portion 107 of elongate body 108, such as by pulling on proximal handle 104 (one-directional arrows), and actuator 106 may be used (two-headed arrow) to activate tissue modifying member(s) 110 to modify target tissue. In the example shown, anchoring force is applied to distal handle 113 by a user's hand 244, and proximal handle 104 is pulled proximally (arrows) to apply tensioning force. In an alternative embodiment, hand 244 may directly grasp guide member 116 at or near its distal portion 117 and thus apply anchoring force to it, thus also applying anchoring force to elongate body 108. Tissue modification via tissue modifying members 110 may include cutting, ablating, dissecting, repairing, reducing blood flow in, shrinking, shaving, burring, biting, remodeling, biopsying, debriding, lysing, debulking, sanding, filing, planing, heating, cooling, vaporizing, delivering a drug to, and/or retracting the target tissue. Once tissue has been modified, tissue modification device 102 and any introducer devices 114, guide members 116 or other devices may be removed from the patient.

In various embodiments of the apparatus, tissue modifying member(s) 110 may be disposed along any suitable length of body 108. In one embodiment, for example, such as an embodiment of the device to be used in a spinal treatment, tissue modifying members 110 may be disposed along a length of the device measuring no longer than 10 cm, and preferably no more than 6 cm, and even more preferably no more than 3 cm. In various embodiments, tissue modifying member(s) 110 may include a rongeur, a curette, a scalpel, one or more cutting blades, a scissors, a forceps, a probe, a rasp, a file, an abrasive element, one or more small planes, an electrosurgical device, a bipolar electrode, a unipolar electrode, a thermal electrode, a rotary powered mechanical shaver, a reciprocating powered mechanical shaver, a powered mechanical burr, a laser, an ultrasound crystal, a cryogenic probe, a pressurized water jet, a drug dispensing element, a needle, a needle electrode, or some combination thereof. In various embodiments, all tissue modifying members 110 may be mobile relative to the elongate body, all may be static, or some may be mobile and some may be static.

These and other aspects and embodiments are described further below.

Figure 3A:
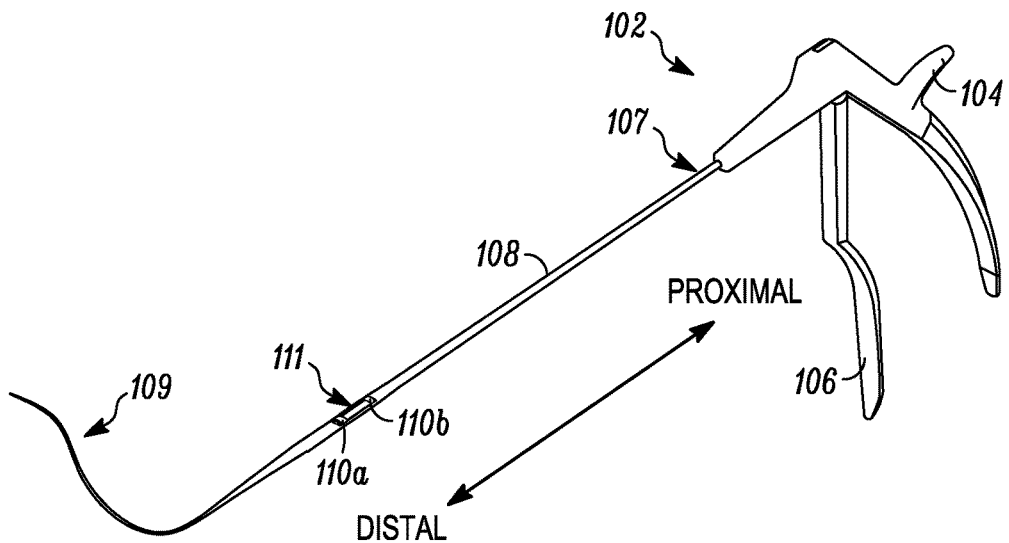
FIG. 3A is a perspective view of a tissue modification device according to one embodiment of the present invention.

Turning now to FIG. 3A-3I, more detailed figures of one embodiment of tissue modification device 102 are shown. Referring to FIG. 3A, tissue modification device 102 may include elongate body 108 having proximal portion 107 and distal portion 109, a window 111 disposed along elongate body 108, two tissue modifying blades 110 exposed through window 111, and proximal handle 104 with actuator 106 coupled with proximal portion 107. In the embodiment shown, the tissue modifying members comprise blades 110, although in alternative embodiments other tissue modifying members may be added or substituted.

In various embodiments, elongate body 108 may have any number of dimensions, shapes, profiles and amounts of flexibility. For example, distal portion 109 is shown having a curved shape to demonstrate that at least a portion of elongate body 108 may be flexible. In some embodiments, as discussed in relation to FIG. 2 above, distal portion 109 may comprise a guidewire, while in other embodiments, distal portion may comprise an extension of elongate body 108. In various embodiments, elongate body 108 may have one or more of a round, ovoid, ellipsoid, flat, cambered flat, rectangular, square, triangular, symmetric or asymmetric cross-sectional shape. As shown in FIGS. 3C and 3D, in the pictured embodiment, elongate body 108 has a relatively flat configuration, which may facilitate placement of body 108 between target and non-target tissues. Distal portion 109 of body 108 may be tapered, to facilitate its passage into or through narrow spaces as well as through small incisions on a patient's skin. Body 108 may also include a slightly widened portion around the area of window 111 and blades. In one embodiment, such as an embodiment used for modifying tissue in a spine, body 108 may have a small profile, such as having a height of not more than 10 mm at any point along its length and a width of not more than 20 mm at any point along its length, or more preferably a height not more than 5 mm at any point along its length and a width of not more than 10 mm at any point along its length, or even more preferably a height not more than 2 mm at any point along its length and a width of not more than 4 mm at any point along its length. Body 108 may be long enough to extend through a first incision on a patient, between target and non-target tissue, and out a second incision on a patient. Alternatively, body 108 may be long enough to extend through a first incision, between the target and non-target tissue, and to an anchoring location within the patient. In another alternative embodiment, body 108 may be long enough to extend through a first incision, between the target and non-target tissue, to a location nearby but distal to the target tissue within the patient, with some portion of tissue modification device 102 anchored to a guidewire. In some embodiments, elongate body 108 includes at least one feature for allowing passage of the body over a guidewire or other guide member or to allow passage of one or more guide members over or through body 108. For example, in various embodiments body 108 may include one or more guidewire lumens, rails, tracks, lengthwise impressions or some combination thereof.

In one embodiment, elongate body 108 is predominantly flexible along its length and comprises any suitable flexible material, such as thin, flexible metals, plastics, fabrics or the like. In some embodiments, it may be advantageous to include one or more rigid sections in elongate body 108, such as to impart pushability to a portion of body 108 or to facilitate application of force to tissue modification members 110 without causing unwanted bending or kinking of elongate body 108. In such embodiments, rigidity may be conferred by using additional materials in body 108 or by making the rigid portions thicker or wider or of a different shape.

Proximal handle 104 may have any suitable configuration according to various embodiments. Similarly, actuator 106 may include any of a number of actuation devices in various embodiments. In the embodiment shown in FIG. 3A, actuator 106 comprises a trigger or moving handle portion, which is grasped by a user and pulled or squeezed toward proximal handle 104 to bring blades 110 together to cut tissue. In an alternative embodiment, actuator 106 instead may include a switch or button for activating a radiofrequency surgical ablation tissue modifying member. In yet another embodiment, actuator 106 may include a combination trigger and switch, one or more pull wires, any suitable form of lever and/or some combination thereof.

Figure 3B:
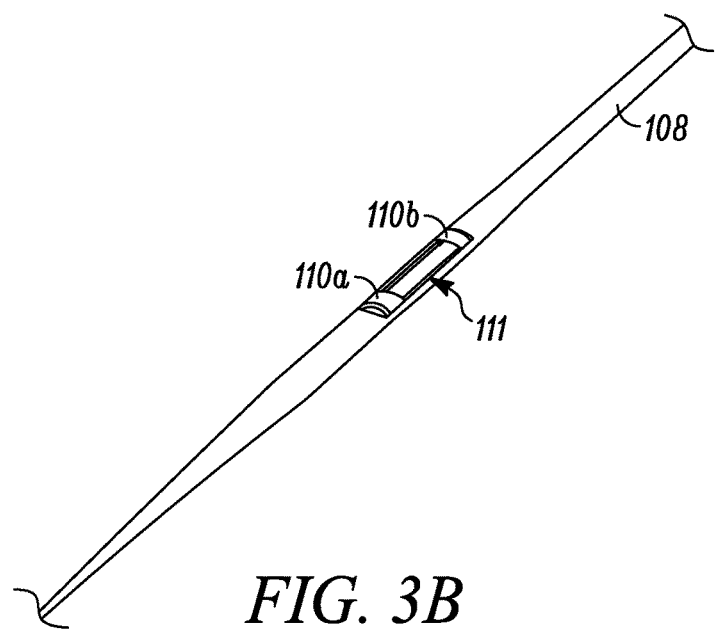
FIG. 3B is a perspective view of a portion of the tissue modification device of FIG. 3A.

FIGS. 3B-3D show in greater detail a portion of tissue modification device 102. In these figures, window 111 and blades 110 are more clearly seen. In one embodiment, at least a portion of elongate body 108 and blades 110 may have a slightly curved configuration. In alternative embodiments, at least a portion of elongate body 108 and blades 110 may be flat. In other alternative embodiments, tissue modification members such as blades 110 may be proud to elongate body 108.

Blades 110 include a distal 110a and a proximal blade 110b that reside at the distal and proximal edges, respectively, of window 111 of elongate body 108. Window 111 of body 108 may accommodate both soft and hard tissue when the device is forcibly applied to the surface of a target tissue site. The top view of the distal portion of elongate body 108, shown in FIG. 3C, depicts the angled edges of distal blade 110a and proximal blade 110b, which facilitate shearing of target tissue. In alternative embodiments, blades 110 may have any of a number of alternative shapes and configurations. The distal portion of body 108 may have a very low profile (height compared to width), as shown in side view FIG. 3D, where only blades 110 protrude from the top surface of the elongate body 108. In one embodiment, also as shown in FIG. 3D, a guidewire tube 120 (or lumen) may extend from (or be coupled with) a lower surface of elongate body 108. The lower surface of elongate body 108 is an example of a protective or non-tissue-modifying surface.

In one embodiment, distal blade 110a is coupled with two pull-wires 118, as seen in FIGS. 3C, 3E and 3F. Pull-wires 118 coupled to and translated by actuator 106 on handle 104 may be used to drive distal blade 110a proximally to contact the cutting edge of proximal blade 110b, thus cutting tissue. Other alternative mechanisms for driving blades 110, such as gears, ribbons or belts, magnets, electrically powered, shape memory alloy, electro magnetic solenoids and/or the like, coupled to suitable actuators, may be used in alternative embodiments. As mentioned, in one embodiment distal blade 110a and/or proximal blade 110b may have an outwardly curvilinear shape along its cutting edge. Alternatively, distal blade 110a may have a different blade shape, including flat, rectilinear, v-shaped, and inwardly curvilinear (concave vs. convex). The cutting edge of either blade 110 may have a sharp edge formed by a simple bevel or chamfer. Alternatively or in addition, a cutting edge may have tooth-like elements that interlock with a cutting edge of an opposing blade, or may have corrugated ridges, serrations, rasp-like features, or the like. In various embodiments, both blades 110 may be of equal sharpness, or alternatively one blade 110 may be sharp and the other substantially flat to provide a surface against which the sharp blade 110 may cut. Alternately or in addition, both cutting edges may be equally hard, or a first cutting edge may be harder than a second, the latter of which deflects under force from the first harder edge to facilitate shearing of the target tissue.

FIGS. 3E and 3F show cross-sectional views through elongate body at lines A-A and B-B, respectively, of FIG. 3C. In some embodiments, all or a portion of elongate body 108, such as the lower surface shown in FIG. 3E, may include a lubricious surface for facilitating manipulation of the tool in the surgical space and at the anatomical site. The lubricious lower surface also provides a barrier between blades 110 and non-target tissue in the surgical space. The lower surface may include a guide member lumen 120 to accommodate a guidewire or other access device or rail. FIG. 3E shows distal blade 110 coupled with pull wires 118. FIG. 3F shows proximal blade 110b, which is not coupled with pull wires 118 but rather fixed to body 108. In various alternative embodiments, proximal blade 110b may be movable distally while distal blade 110a is static, both blades may be moved toward one another, or a different number of blades may be used, such as one blade drawn toward a backstop or more than two blades, one or more of which may be mobile. In various alternative embodiments, guide member lumen 120 may be accommodated on a side surface or more centrally within elongate body 108. In further alternative embodiments, the one or more guide member lumens 120 may comprise one or more various cross sectional shapes, for example substantially round, substantially oval, or substantially rectabular, to accommodate alternative guide members, for example flat or rectangular guidewires, needles or rails. In still other alternative embodiments guide member lumen 120 may be adjustably coupled with the elongate body 108 to enable manipulation of the location of the elongate body 108 and therefore the tissue modifying members 110 relative to the guiding member.

Figure 3G:
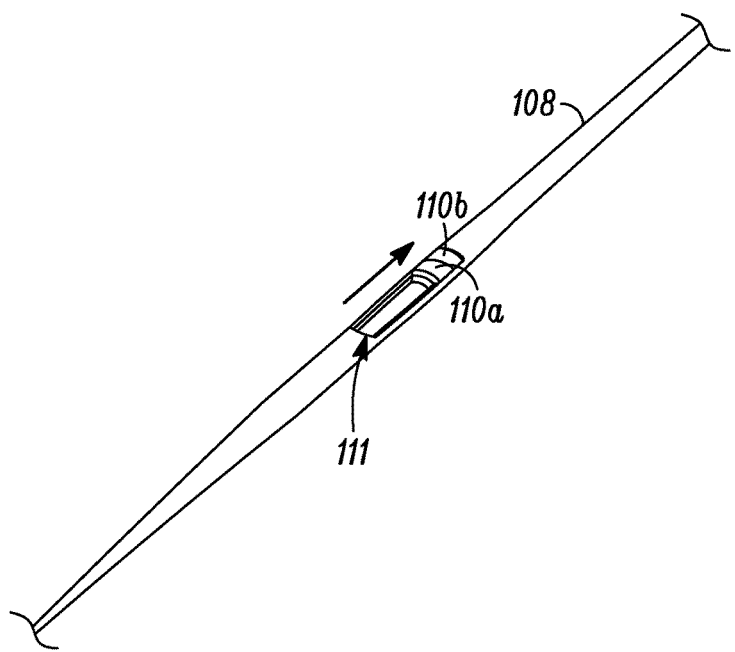
FIG. 3G is a perspective view of a portion of the tissue modification device of FIGS. 3B-3F, shown with a blade of the device in a closed position according to one embodiment of the present invention.
Figure 3H:
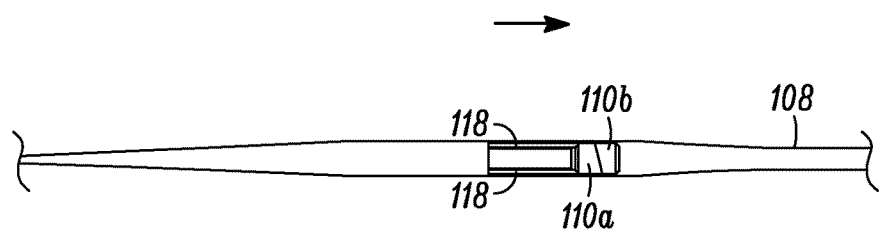
FIG. 3H is a top view of the portion shown in FIG. 3G.
Figure 3I:
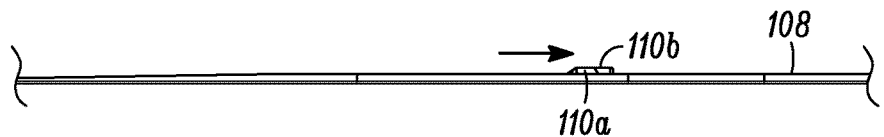
FIG. 3I is a side view of the portion shown in FIGS. 3G and 3H.

Referring now to FIGS. 3G-3I, blades 110 are shown in their closed position. In one embodiment, when distal blade 110a is drawn proximally to cut tissue, at least some of the cut tissue is captured in a hollow interior portion of elongate body 108. Various embodiments may further include a cover, a cut tissue housing portion and/or the like for collecting cut tissue and/or other tissue debris. Such collected tissue and debris may then be removed from the patient during or after a tissue modification procedure. During a given tissue modification procedure, distal blade 110a may be drawn proximally to cut tissue, allowed to retract distally, and drawn proximally again to further cut tissue as many times as desired to achieve a desired amount of tissue cutting.

Blades 110 may be made from any suitable metal, polymer, ceramic, or combination thereof. Suitable metals, for example, may include but are not limited to stainless steel (303, 304, 316, 316L), nickel-titanium alloy, tungsten carbide alloy, or cobalt-chromium alloy, for example, Elgiloy®. (Elgin Specialty Metals, Elgin, Ill., USA), Conichrome® (Carpenter Technology, Reading, Pa., USA), or Phynox® (Imphy SA, Paris, France). In some embodiments, materials for the blades or for portions or coatings of the blades may be chosen for their electrically conductive or thermally resistive properties. Suitable polymers include but are not limited to nylon, polyester, Dacron®, polyethylene, acetal, Delrin® (DuPont, Wilmington, Del.), polycarbonate, nylon, polyetheretherketone (PEEK), and polyetherketoneketone (PEKK). In some embodiments, polymers may be glass-filled to add strength and stiffness. Ceramics may include but are not limited to aluminas, zirconias, and carbides. In various embodiments, blades 110 may be manufactured using metal injection molding (MIM), CNC machining, injection molding, grinding and/or the like. Pull wires 118 be made from metal or polymer and may have circular, oval, rectangular, square or braided cross-sections. In some embodiments, a diameter of a pull wire 118 may range from about 0.001"-0.050", and more preferably from about 0.010"-0.020".

Depending on the tissue to be treated or modified, activating blades 110 (or other tissue modifying members in alternative embodiments) may cause them to modify target tissue along an area having any of a number of suitable lengths. In use, it may also be advantageous to limit the extent of action of blades 110 or other tissue modifying members to a desired length of tissue, thus not allowing blades 110 to affect tissue beyond that length. In so limiting the effect of blades, unwanted modification of, or damage to, surrounding tissues and structures may be limited or even eliminated. In one embodiment, for example, where the tissue modification device is used to modify tissue in a spine, blades 110 may operate along a length of target tissue of no more than 10 cm, and preferably no more than 6 cm, and even more preferably no more than 3 cm. Of course, in other parts of the body and to address other tissues, different tissue modification devices may be used and tissue modifying members may have many different lengths of activity. In one embodiment, to facilitate proper location of tissue modifying members, such as blades 110, relative to target tissue, the tissue modifying members and/or the elongate body and/or one or more additional features intended for just such a purpose may be composed of a material readily identifiable via x-ray, fluoroscopic, magnetic resonance or ultrasound imaging techniques.

In various embodiments, a number of different techniques may be used to prevent blades 110 (or other tissue modifying members) from extending significantly beyond the target tissue. In one embodiment, for example, preventing blades 110 from extending significantly beyond the target tissue involves holding tissue modification device 102 as a whole predominantly stable to prevent device 102 from translating in a direction toward its proximal portion or toward its distal portion while activating blades 110. Holding device 102 stable is achieved by anchoring one end of the device and applying tensioning force at or near the other end, as described further below.

In the embodiment shown in FIGS. 3A-3I, pull wires 118 are retracted proximally by squeezing actuator 106 proximally. In an alternative embodiment, squeezing actuator 106 may cause both blades 110 to translate inward so that they meet approximately in the middle of window 111. In a further embodiment, distal blade 110a may be returned to it's starting position by a pulling force generated from the distal end of device 102, for example by using a distal actuator that is attached to distal wires, or by pulling on the distal guide member which is attached to distal blade 110a. In yet another alternative embodiment, proximal blade 110b may be moved to cut by a pulling force generated from the distal end of device 102, for example by using a distal actuator that is attached to distal wires, or by pulling on the distal guide member which is attached to proximal blade 110b. In yet another embodiment, squeezing actuator 106 may cause proximal blade 110b to move distally while distal blade 110a stays fixed. In other alternative embodiments, one or more blades 110 may move side-to-side, one or more blades 110 may pop, slide or bow up out of window 111 when activated, or one or more blades 110 may expand through window. In another embodiment, one or more blades 110 and/or other tissue modifying members of device 102 may be powered devices configured to cut, shave, grind, abrade and/or resect target tissue. In other embodiments, one or more blades may be coupled with an energy transmission device, such as a radiofrequency (RF) or thermal resistive device, to provide energy to blade(s) 110 for cutting, ablating, shrinking, dissecting, coagulating or heating and thus enhancing tissue modification. In another embodiment, a rasp or file may be used in conjunction with or coupled with one or more blades. In any of these embodiments, use of actuator 106 and one or more moving blades 110 provides for tissue modification with relatively little overall translation or other movement of tissue modification device 102. Thus, target tissue may be modified without extending blades 110 or other tissue modification members significantly beyond an area of target tissue to be treated.

Figure 4A:
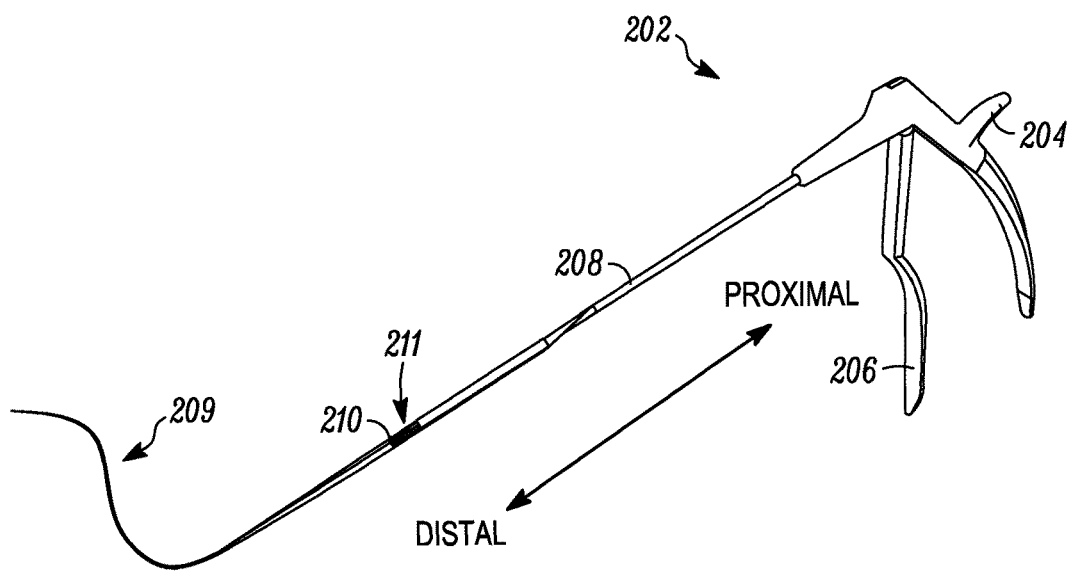
FIG. 4A is a perspective view of a tissue modification device according to one embodiment of the present invention.
Figure 4B:
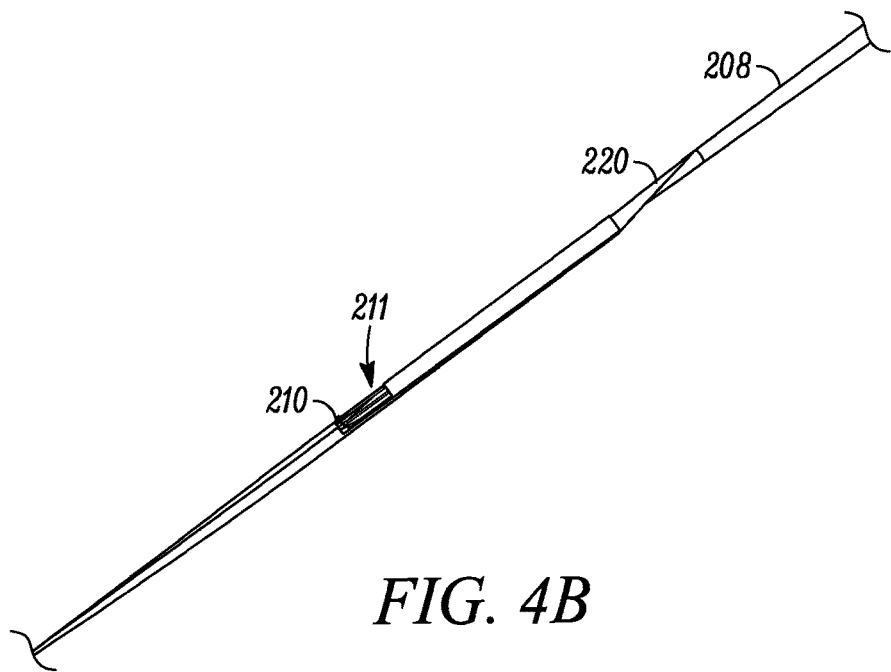
FIG. 4B is a perspective view of a portion of the tissue modification device of FIG. 4A.
Figure 4C:
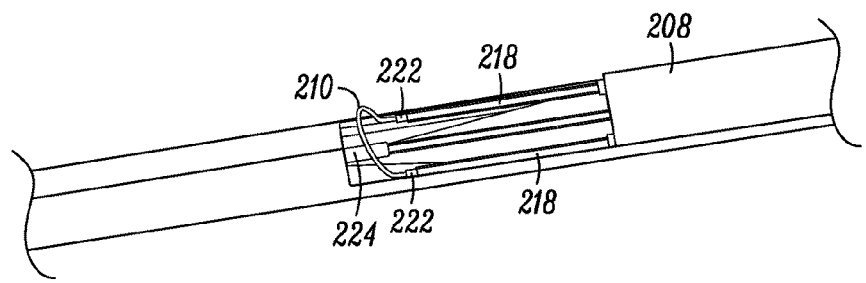
FIG. 4C is a close-up, perspective view of a portion of the tissue modification device of FIGS. 4A and 4B, showing a tissue modifying member according to one embodiment of the present invention.

Referring now to FIGS. 4A-4C, in an alternative embodiment, a tissue modification device 202 may include an elongate body 208 having a proximal portion and a distal portion 209, a handle 204 and actuator 206 coupled with proximal portion, and a window 211 and tissue modifying member 210 disposed near distal portion 209. As seen more clearly in FIGS. 4B and 4C, in the embodiment shown, tissue modifying member 210 comprises an RF electrode wire loop. Wire loop 210 may comprise any suitable RF electrode, such as those commonly used and known in the electrosurgical arts, and may be powered by an internal or external RF generator, such as the RF generators provided by Gyrus Medical, Inc. (Maple Grove, Minn.). Any of a number of different ranges of radio frequency may be used, according to various embodiments. For example, some embodiments may use RF energy in a range of between about 70 hertz and about 5 megahertz. In some embodiments, the power range for RF energy may be between about 0.5 Watts and about 200 Watts. Additionally, in various embodiments, RF current may be delivered directly into conductive tissue or may be delivered to a conductive medium, such as saline or Lactate Ringers solution, which may in some embodiments be heated or vaporized or converted to plasma that in turn modifies target tissue. Distal portion 209 includes a tapered tip, similar to that described above, to facilitate passage of elongate body 208 into narrow anatomical sites. Handle 204 and actuator 206 are similar to those described above, although in the embodiment of FIGS. 4A-4C, actuator 206 may be used to change the diameter of the wire loop 210. Using actuator 206, wire loop 210 may be caused to extend out of window 211, expand, retract, translate and/or the like. Some embodiments may optionally include a second actuator (not shown), such as a foot switch for activating an RF generator to delivery RF current to an electrode.

Elongate body 208 may be fabricated from any suitable material and have any of a number of configurations. In one embodiment, body 208 comprises a metal tube with a full-thickness slit (to unfold the tube into a flat form—not shown) or stiffening element (not shown). The split tube provides for a simple manufacturing process as well as a conductive pathway for bi-polar RF operation.

Referring to FIG. 4C, insulators 222 may be disposed around a portion of wire loop 210 so that only a desired portion of wire loop 210 may transfer RF current into the tissue for tissue modifying capability. Wire loop 210, covered with insulators 222 may extend proximally into support tubes 218. In various alternative embodiments, an electrode tissue modifying member (of which wire loop 210 is but one example) may be bipolar or monopolar. For example, as shown in FIG. 4C, a sleeve 224 housed toward the distal portion of window 211 may act as a return electrode for wire loop 210 in a bipolar device. Wire loop electrodes 210 may be made from various conductive metals such as stainless steel alloys, nickel titanium alloys, titanium alloys, tungsten alloys and the like. Insulators 222 may be made from a thermally and electrically stable polymer, such as polyimide, polyetheretherketone (PEEK), polytetrafluoroethylene (PTFE), polyamide-imide, or the like, and may optionally be fiber reinforced or contain a braid for additional stiffness and strength. In alternative embodiments, insulators 222 may be composed of a ceramic-based material.

In one embodiment, wire loop 210 may be housed within elongate body 208 during delivery of tissue modification device 202 into a patient, and then caused to extend up out of window 211, relative to the rest of body 208, to remove tissue. Wire loop 210 may also be flexible so that it may pop or bow up out of window 211 and may deflect when it encounters hard tissue surfaces. Wire loop 210 may have any of a number of shapes, such as curved, flat, spiral or ridged. Wire loop 210 may have a diameter similar to the width of body 208, while in alternative embodiments it may expand when extended out of window 211 to have a smaller or larger diameter than that of body 208. Pull wires (not shown) may be retracted proximally, in a manner similar to that described above, in order to collapse wire loop 210, decrease the diameter and lower the profile of the wire loop 210, and/or pull wire loop 210 proximally to remove tissue or be housed within body 208. The low profile of the collapsed wire loop 210, facilitates insertion and removal of tissue modification device 202 prior to and after tissue modification. As the wire loop 210 diameter is reduced, support tubes 218 deflect toward the center of elongate body 208.

In an alternative embodiment (not shown), tissue modification device 202 may include multiple RF wire loops 210 or other RF members. In another embodiment, device 202 may include one or more blades as well as RF wire loop 210. In such an embodiment, wire loop 210 may be used to remove or otherwise modify soft tissues, such as ligamentum flavum, or to provide hemostasis, and blades may be used to modify hard tissues, such as bone. In other embodiments, as described further below, two separate tissue modification devices (or more than two devices) may be used in one procedure to modify different types of tissue, enhance modification of one type of tissue or the like.

In other alternative embodiments, tissue modification devices 202 may include tissue modifying members such as a rongeur, a curette, a scalpel, a scissors, a forceps, a probe, a rasp, a file, an abrasive element, one or more small planes, a rotary powered mechanical shaver, a reciprocating powered mechanical shaver, a powered mechanical burr, a laser, an ultrasound crystal a cryogenic probe, a pressurized water jet, a drug dispensing element, a needle, a needle electrode, or some combination thereof. In some embodiments, for example, it may be advantageous to have one or more tissue modifying members that stabilize target tissue, such as by grasping the tissue or using tissue restraints such as barbs, hooks, compressive members or the like. In one embodiment, soft tissue may be stabilized by applying a contained, low-temperature substance (for example, in the cryo-range of temperatures) that hardens the tissue, thus facilitating resection of the tissue by a blade, rasp or other device. In another embodiment, one or more stiffening substances or members may be applied to tissue, such as bioabsorbable rods.

Figure 5A:
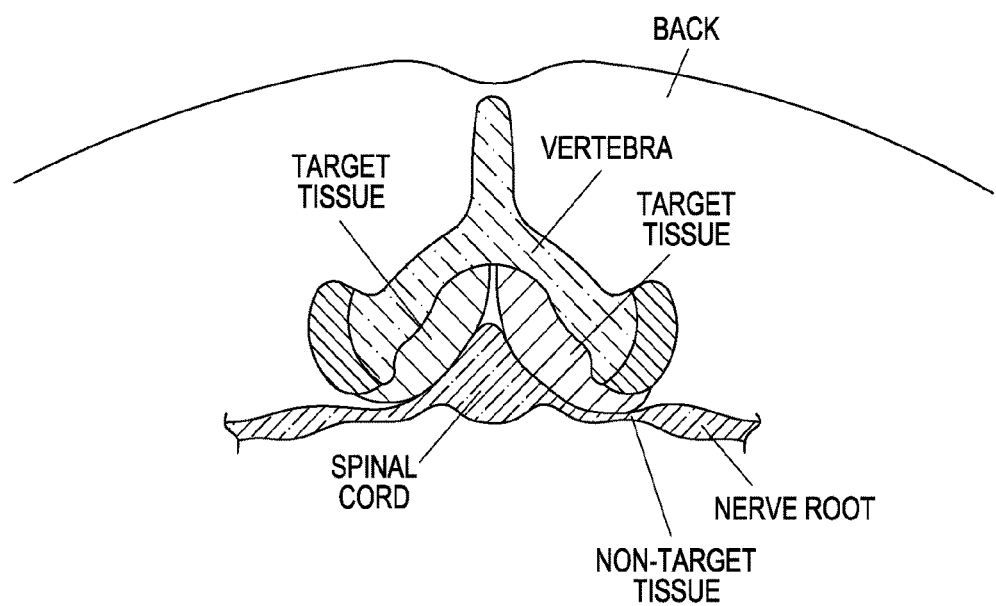
FIGS. 5A-5D are cross-sectional views of a spine and demonstrate a method for using a tissue modification device according to one embodiment of the present invention.

Referring now to FIGS. 5A-5D, one embodiment of a method for modifying tissue in a spine is demonstrated in simplified, diagrammatic, cross-sectional views of a portion of a patient's back and spine. FIG. 5A shows a portion of the patient's back in cross section, with a portion of a vertebra, the spinal cord with branching nerve roots, and target tissue, which in this illustration is the ligamentum flavum and possibly a portion of the facet capsule. The target tissue is typically impinging directly on one or more of the group including nerve roots, neurovascular structures, dorsal root ganglia, cauda equina, or individual nerves.

Figure 5B:
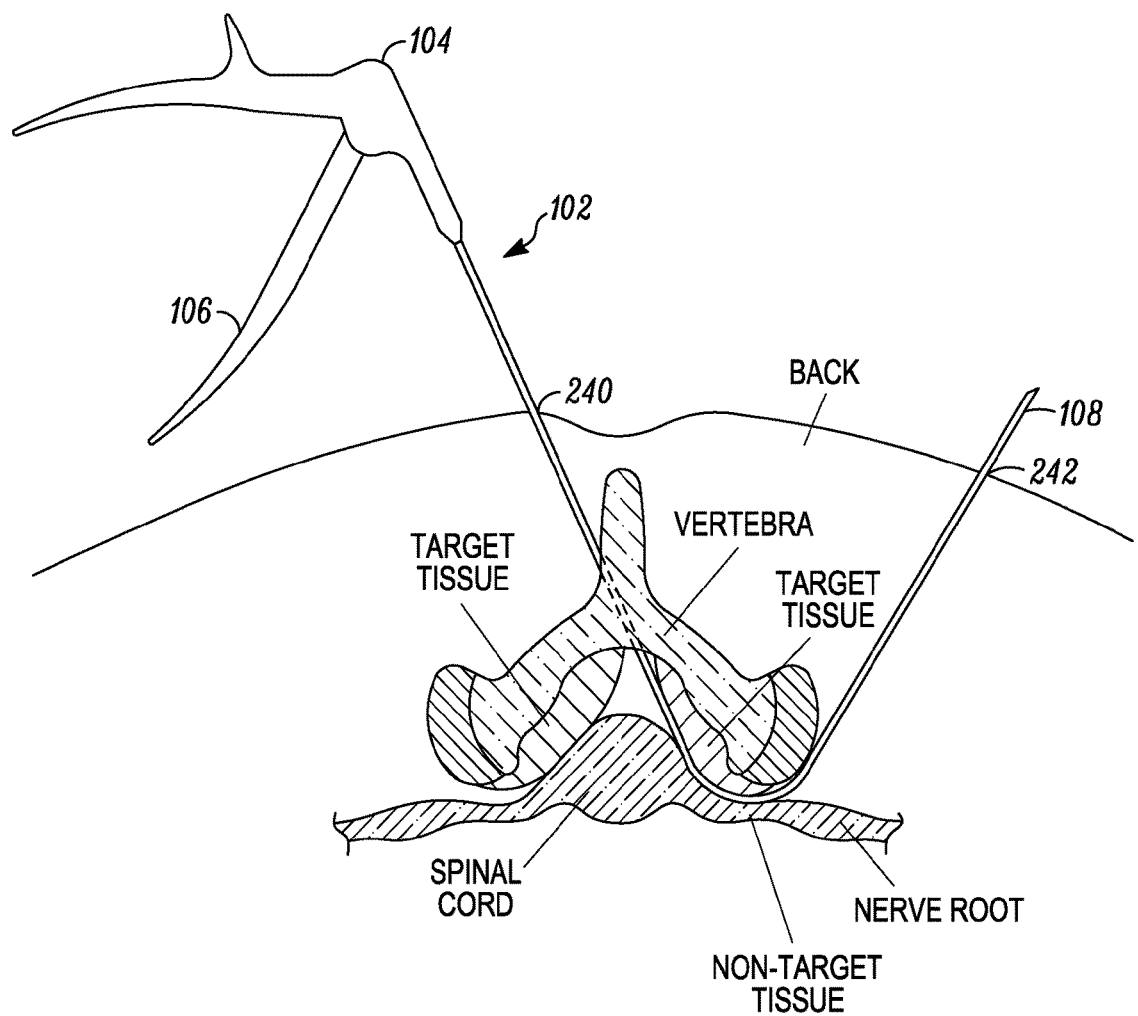

In FIG. 5B, tissue modification device 102 has been positioned in the patient's back to perform a tissue modification procedure. Various methods, devices and systems for introducing device 102 into the patient and advancing it to the position for modifying tissue are described in further detail below. Generally, device 102 may be positioned via a percutaneous or open surgical procedure, according to various embodiments. In one embodiment, device 102 may be inserted into the patient through a first incision 240, advanced into the spine and between target tissue and non-target tissue (such as spinal cord, nerve roots, nerves and/or neurovascular tissue), and further advanced so a distal portion of elongate body 108 exits a second (or distal) incision or non-incision exit point 242 to reside outside the patient. In positioning device 102, one or more tissue modifying members (not shown) are positioned to face the target tissue, while one or more protective portions of elongate body 108 face non-target tissue.

Figure 5C:
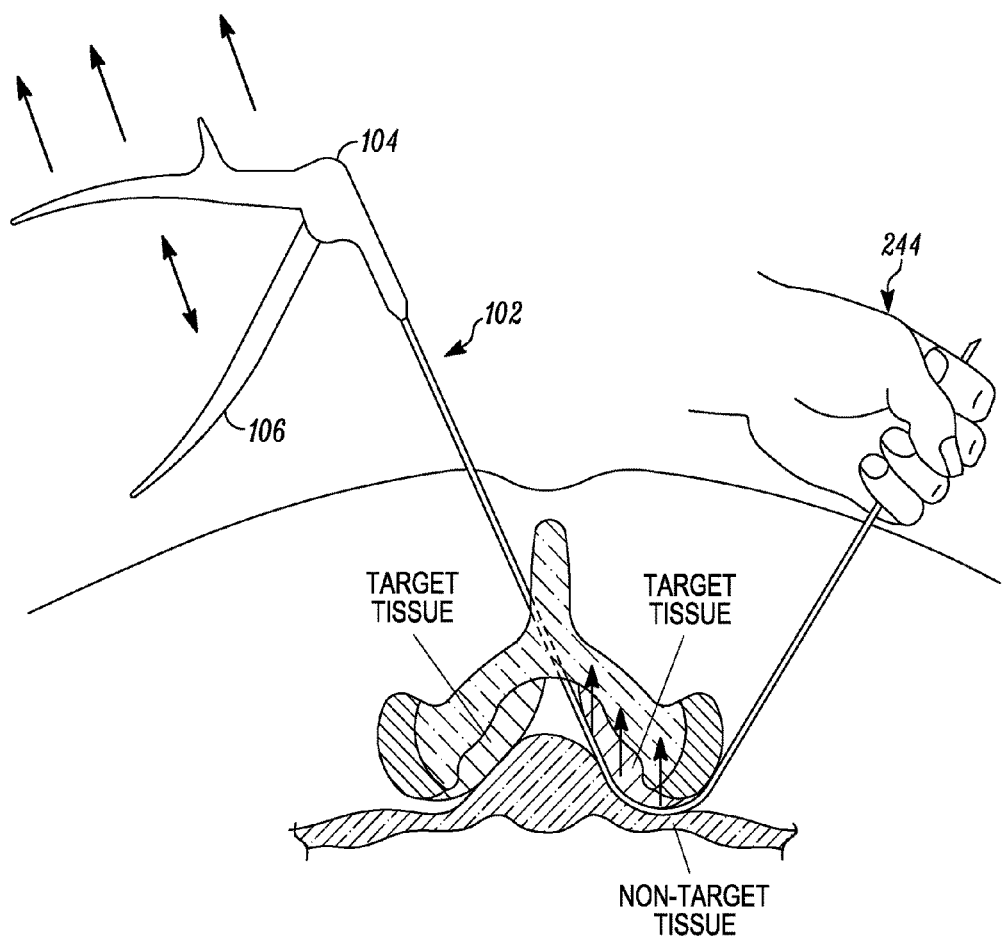

Referring to FIG. 5C, once device 102 is positioned in a desired location, anchoring force may be applied at or near the distal portion of elongate body 108. In one embodiment, applying anchoring force involves a user 244 grasping body 108 at or near its distal portion. In alternative embodiments, as described further below, anchoring force may be applied by deploying one or more anchor members disposed at or near the distal portion of body 108, or by grasping a guidewire or other guide member coupled with or extending through at least part of body 108, in some cases using a distal handle (not shown). Once the anchoring force is applied, proximally-directed tensioning force may be applied to device 102, such as by pulling proximally on proximal handle 104 (one-directional, diagonal arrows). This tensioning force, when applied to the substantially anchored device 102, may help urge the tissue modifying member(s) against the target tissue (one-directional, vertical arrows near target tissue), thus enhancing contact with the target tissue and facilitating its modification. Of course, in this or other embodiments, as mentioned above, any combination of tensioning and/or anchoring forces may be applied to proximal and distal portions of tissue modification device 102, either in different procedures or during the same procedure. With the tissue modifying member(s) contacting the target tissue, actuator 106 may be squeezed or pulled (two-headed arrow) to cause the tissue modifying member(s) to modify tissue. (Alternative actuators may be activated in different ways in alternative embodiments.)

In various alternative embodiments, certain of the above-described steps may be carried out in different order. For example, in one embodiment the distal portion of elongate body 108 may be anchored within or outside the patient before the tissue modifying members are positioned adjacent the target tissue. In another alternative embodiment, the proximal portion of device 102 may be anchored, and the tensioning force may be applied to the distal portion of device 102. In yet another embodiment, tensioning force may be applied to both ends of the device. In yet another embodiment, a second handle and actuator may be coupled with the distal end of body 108 after it exits the patient's back, allowing tensioning forces as well as tissue modifying actuation to occur at both the proximal and distal portions of device 102. By anchoring one end of device 102 and applying tensioning force to the opposite end, contact of the tissue modifying members with the target tissue is enhanced, thus reducing or eliminating the need for translating or otherwise moving device 102 as a whole and reducing the overall profile and the resulting access pathway required to position the device. Reducing movement and profile of device 102 and using tissue modifying members confined to a relatively small area of device 102 helps facilitate target tissue modification while minimizing or eliminating damage to surrounding tissues or structures.

As mentioned above, tissue may be modified using one tissue modification device or multiple devices, according to various embodiments. In one embodiment, for example, an RF electrosurgical tissue modification device may be used in the patient to remove soft tissue such as ligament, and a bladed tissue modification device such as a rongeur may then be used to remove additional soft tissue, calcified soft tissue, or hard tissue such as bone. In some embodiments, such multiple devices may be inserted, used and removed serially, while in alternative embodiments such devices may be inserted into the patient at the same time to be used in combination.

Figure 5D:
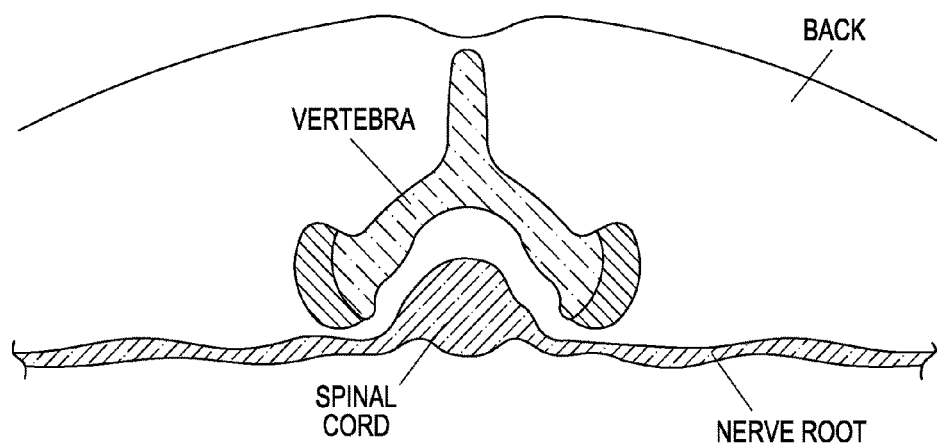

Referring to FIG. 5D, using one or more tissue modification devices 102, a desired amount of target tissue may be removed from more than one area in the spine. FIGS. 5A-5C demonstrate removal of target tissue on one side of the spine, and that method or a similar method may also be used to remove target tissue on an opposite side of the spine, as shown in FIG. 5D, where target tissue has been removed from both sides. That the desired amount of tissue has been removed may be confirmed by tactile feedback from the device or from a separate device, by testing nerve conduction through one or more previously impinged nerves, by testing blood flow through one or more previously impinged blood vessels, by passing (independently or over the guide member) a measurement probe or sound through the treated portion, through one or more radiographic tests, through some combination thereof, or by any other reasonable means.

Figure 6A:
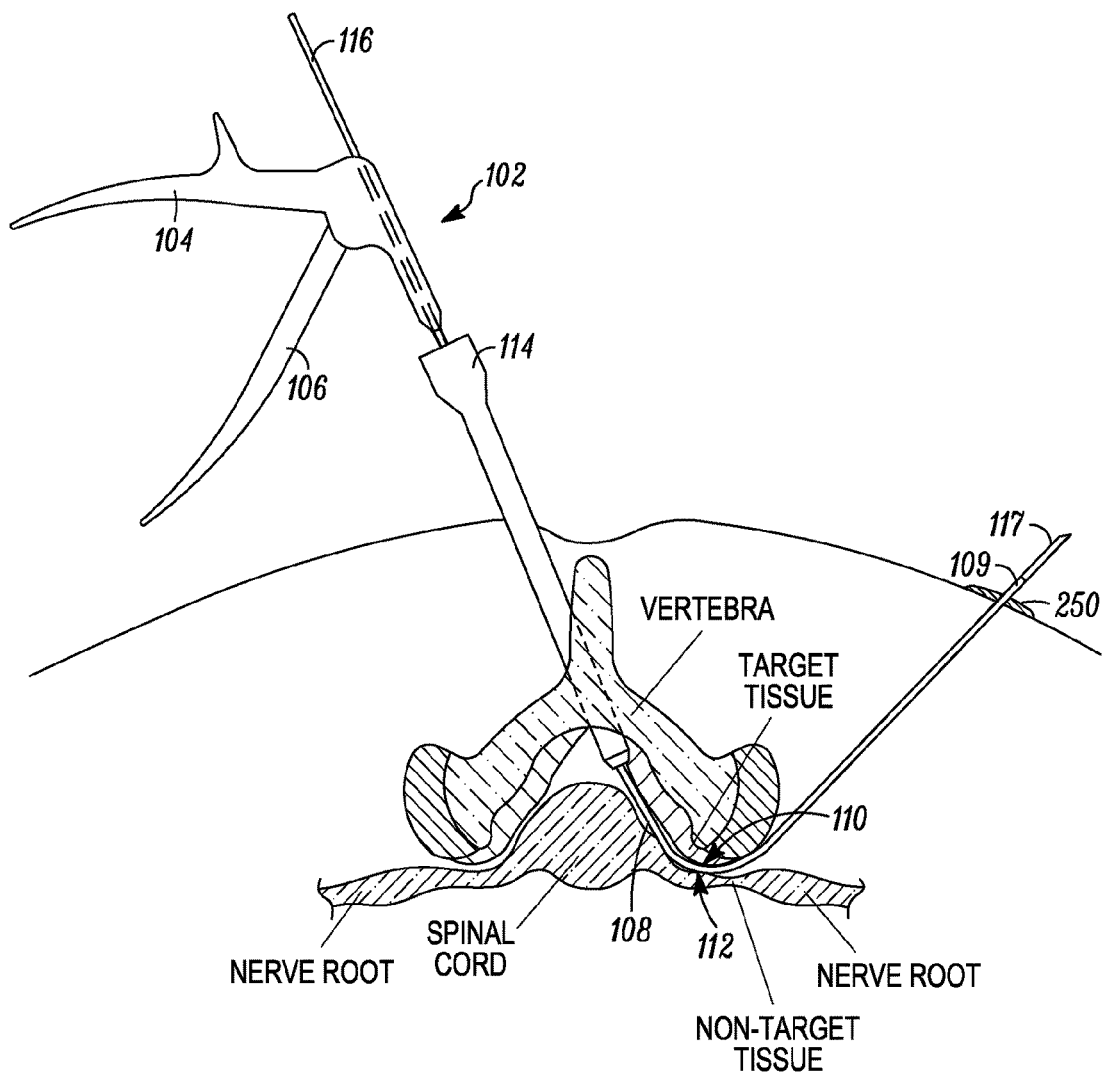
FIG. 6A is a cross-sectional view of a portion of a patient's spine and back, with apparatus for modifying tissue in position for modifying spinal tissue and with a distal portion of the apparatus anchored outside the patient according to one embodiment of the present invention.

Referring now to FIG. 6A, tissue modification device 102 is shown with one embodiment of a distal anchoring member 250 deployed at the patient's skin. In various embodiments, anchoring members may include but are not limited to one or more handles, barbs, hooks, screws, toggle bolts, needles, inflatable balloons, meshes, stents, wires, lassos, backstops or the like. In some embodiments, anchoring members 250 may be disposed at the extreme distal portion 109 of elongate body 108, while in other embodiments anchoring members 250 may be located more proximally. In the embodiment shown, anchoring members 250 are deployed at the patient's skin. In an alternative embodiment, anchoring may be achieved outside the patient by deploying one or more anchoring members 250 above the skin and having a user grasp the anchoring members 250. In an alternative embodiment, anchoring may be achieved outside the patient by deploying one or more anchoring members 250 above the skin and having a user grasp anchoring members 250, after tissue modification device 102 has been anchored to the guide member. In another alternative embodiment, anchoring may be achieved outside the patient by attaching anchoring member 250 to an external device, for example one that is mounted on the patient or on the procedure table. In a further alternative embodiment, anchoring may be achieved outside the patient by attaching the guide member to an external device, for example one that is mounted to on the patient or on the procedure table, after tissue modification device 102 has been anchored to the guide member. Anchoring members 250 generally are deployable from a first, contracted configuration to facilitate delivery of device 102, to a second, expanded configuration to facilitate anchoring. This change in configuration may be achieved, for example, by using shape memory or super-elastic materials, by spring loading anchoring members 250 into body 108 or the like. In most embodiments, anchoring members 250 may also be collapsed down into the first, contracted configuration after a tissue modification procedure has been performed, to facilitate withdrawal of device 102 from the patient. In an alternative embodiment, anchoring members 250 may detach from body 108 and may be easily removable from the patient's skin.

Figure 6B:
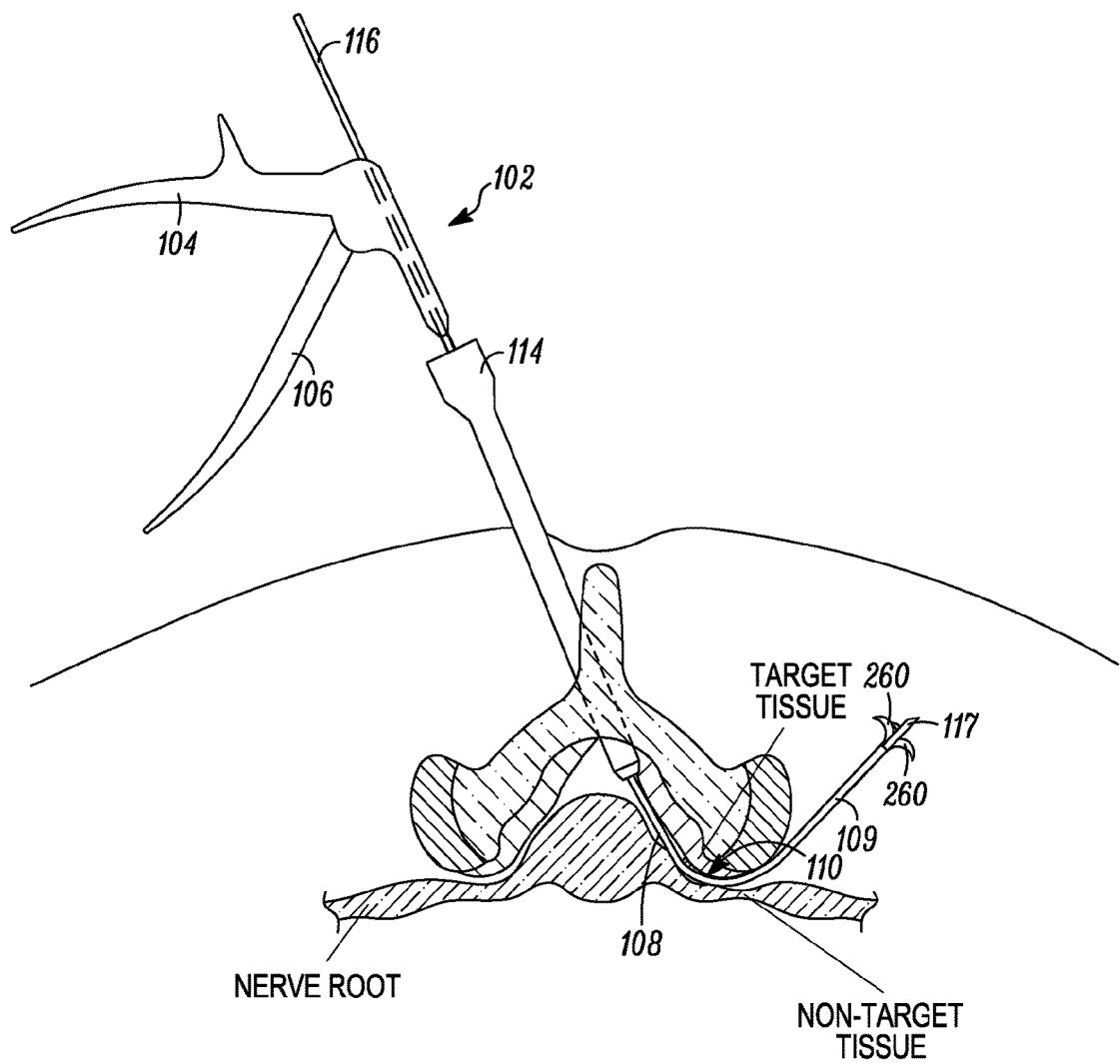
FIG. 6B is a cross-sectional view of a portion of a patient's spine and back, with apparatus for modifying tissue in position for modifying spinal tissue and with a distal portion of the apparatus anchored inside the patient according to one embodiment of the present invention.

FIG. 6B shows tissue modification device 102 with an alternative embodiment of a distal anchoring member 260. Here, distal anchoring member 260 includes multiple hooks or barbs extended out the distal portion 109 of elongate body 108 within the patient's back. In using such an embodiment, it may not be necessary to pass guide member 117 through a second, distal incision on the patient, although in some embodiments guide member 117 may extend significantly beyond distal portion 109. Anchoring member(s) 260, according to various embodiments, may be deployed so as to anchor to bone, ligament, tendon, capsule, cartilage, muscle, or any other suitable tissue of the patient. They may be deployed into vertebral bone or other suitable tissue immediately adjacent an intervertebral foramen or at a location more distant from the intervertebral foramen. When a tissue modification procedure is complete, anchoring members 260 are retracted within elongate body for removal of device 102 from the patient.

Figure 7A:
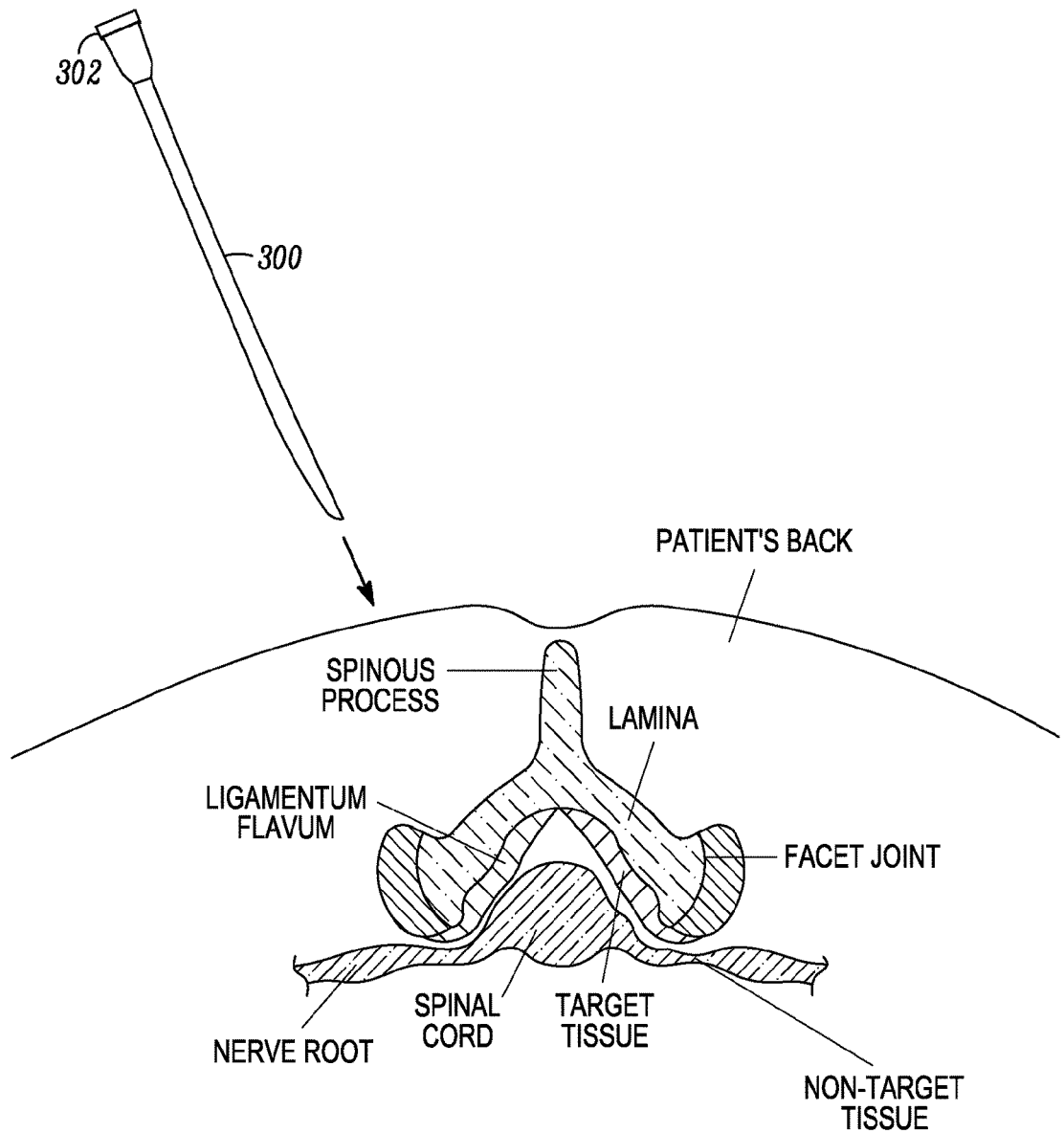
FIGS. 7A-7S are cross-sectional views of a portion of a patient's spine and back, demonstrating a method for introducing apparatus for modifying spinal tissue to an area in the spine for performing the tissue modification according to one embodiment of the present invention.
Figure 7B:
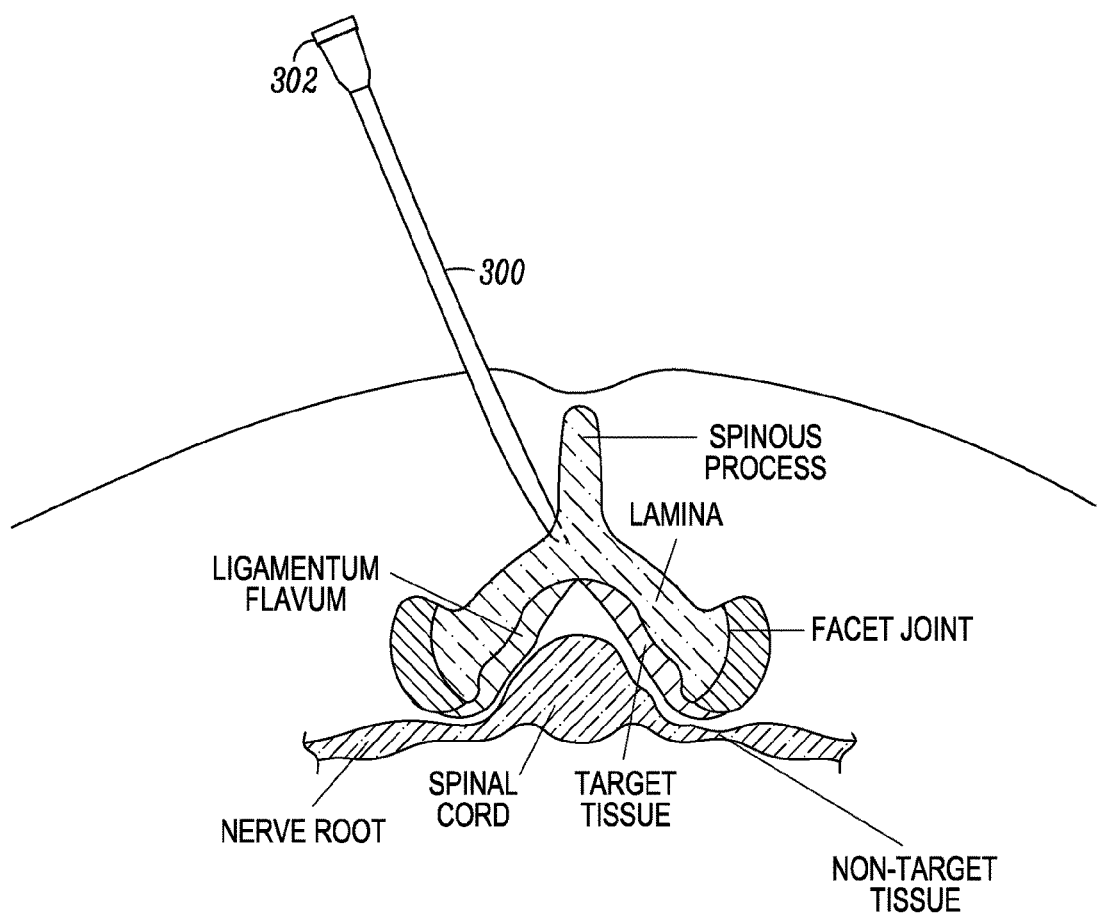
Figure 7C:
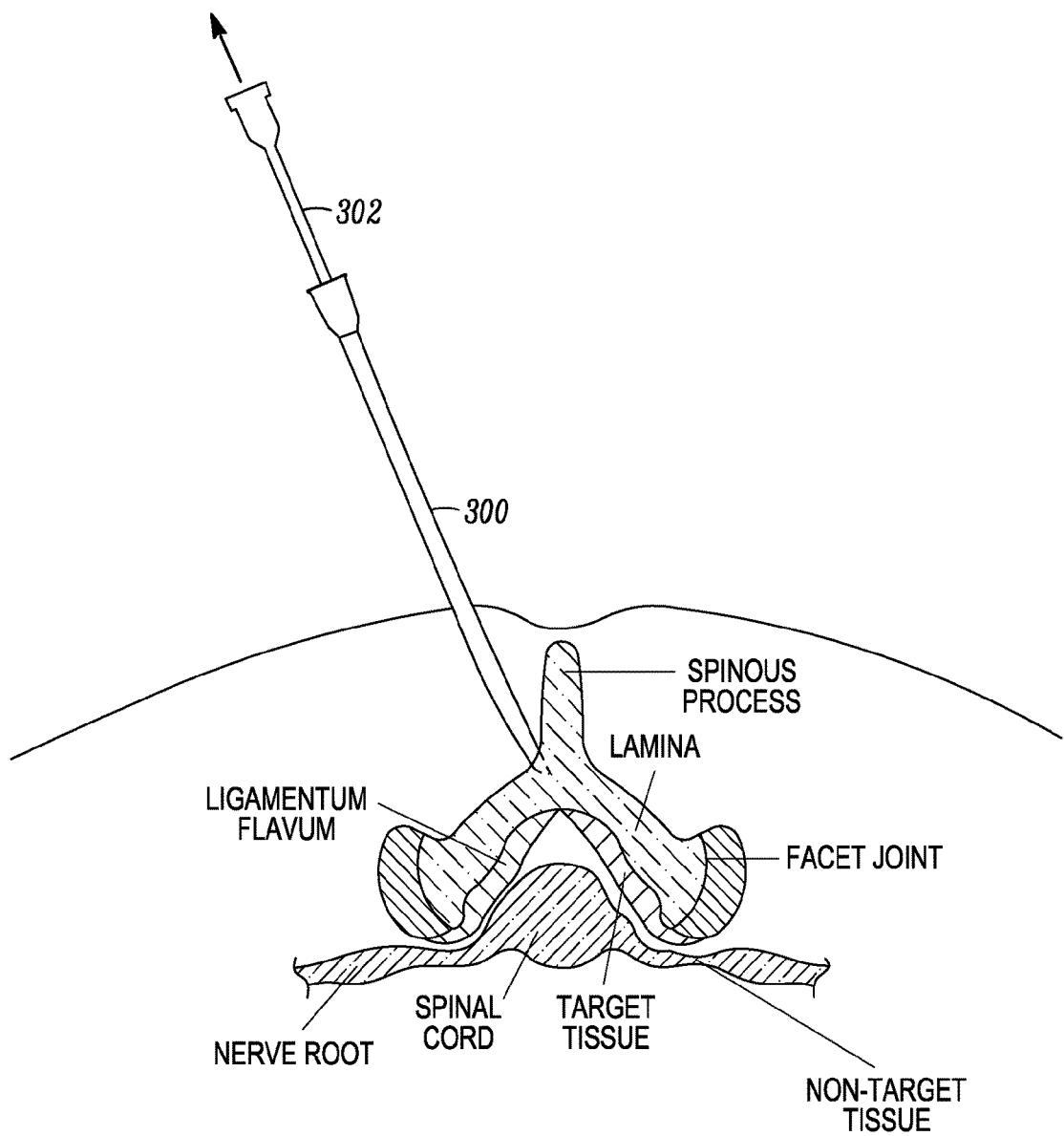
Figure 7D:
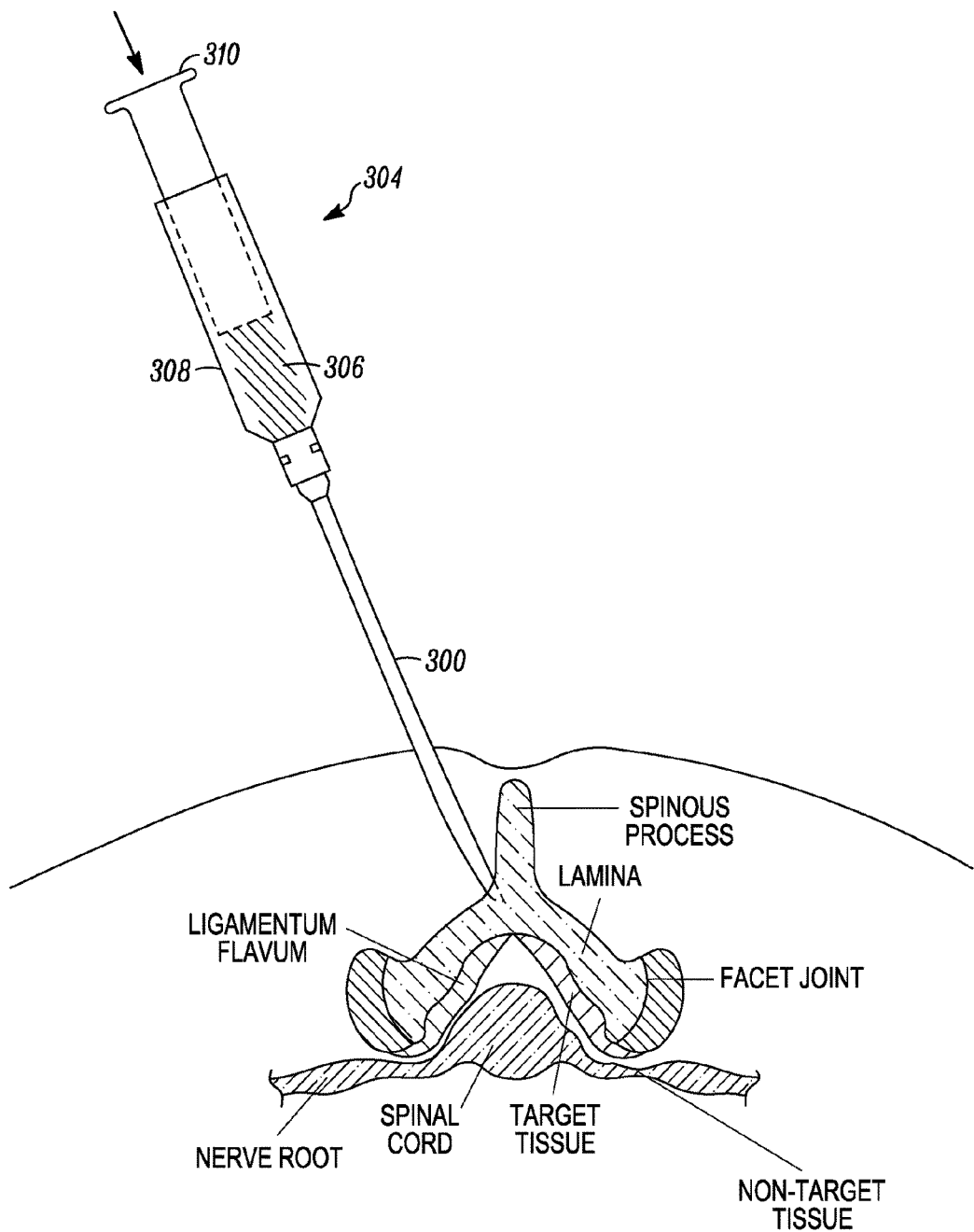
Figure 7E:
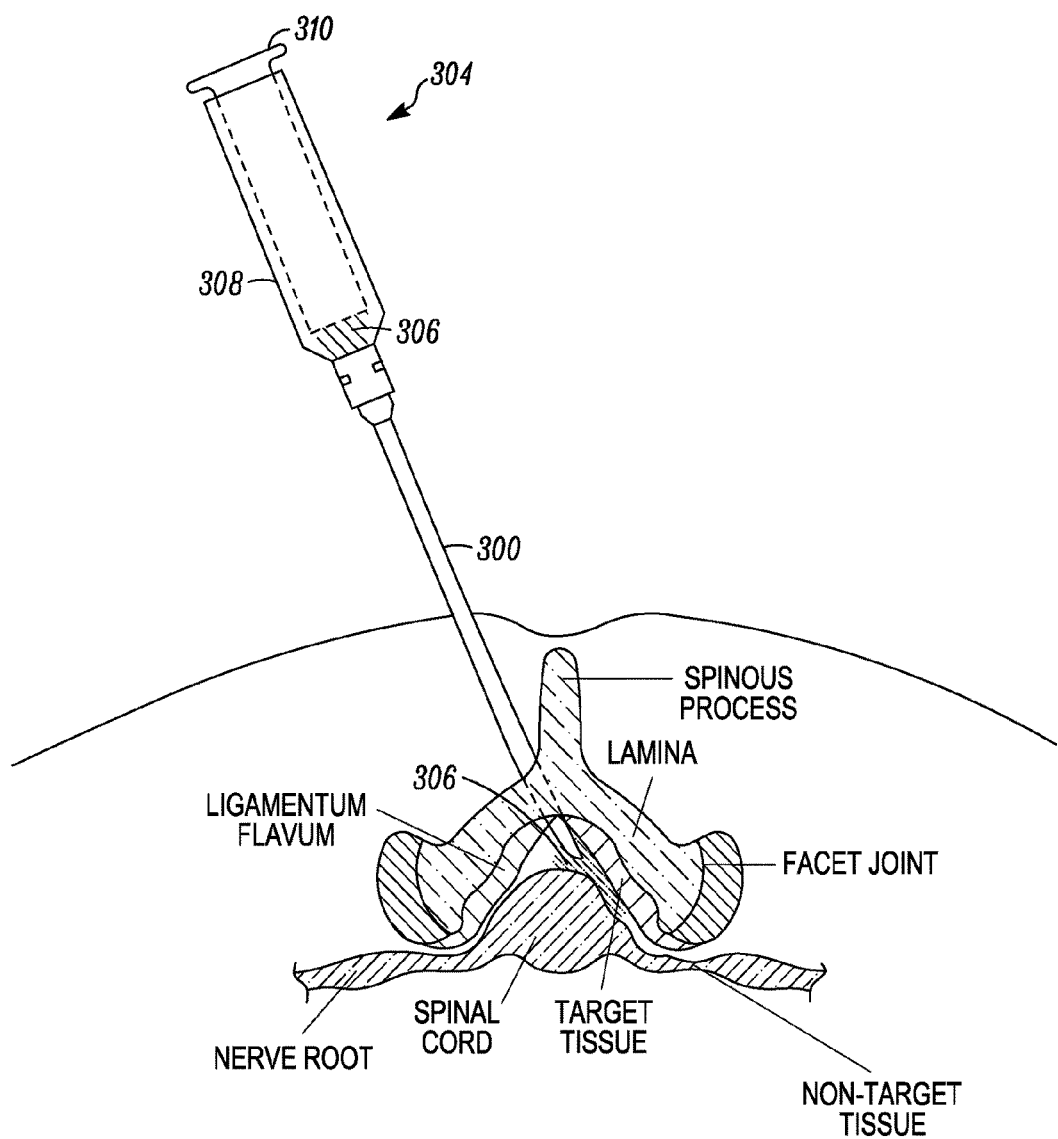
Figure 7F:
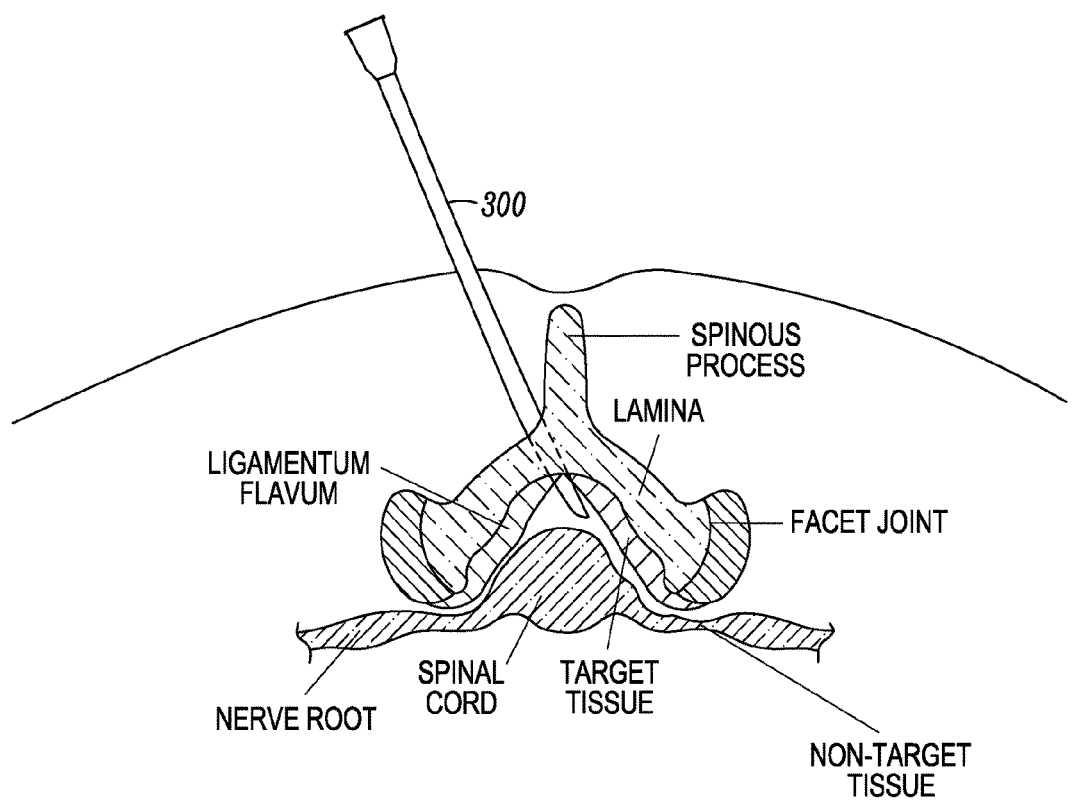
Figure 7G:
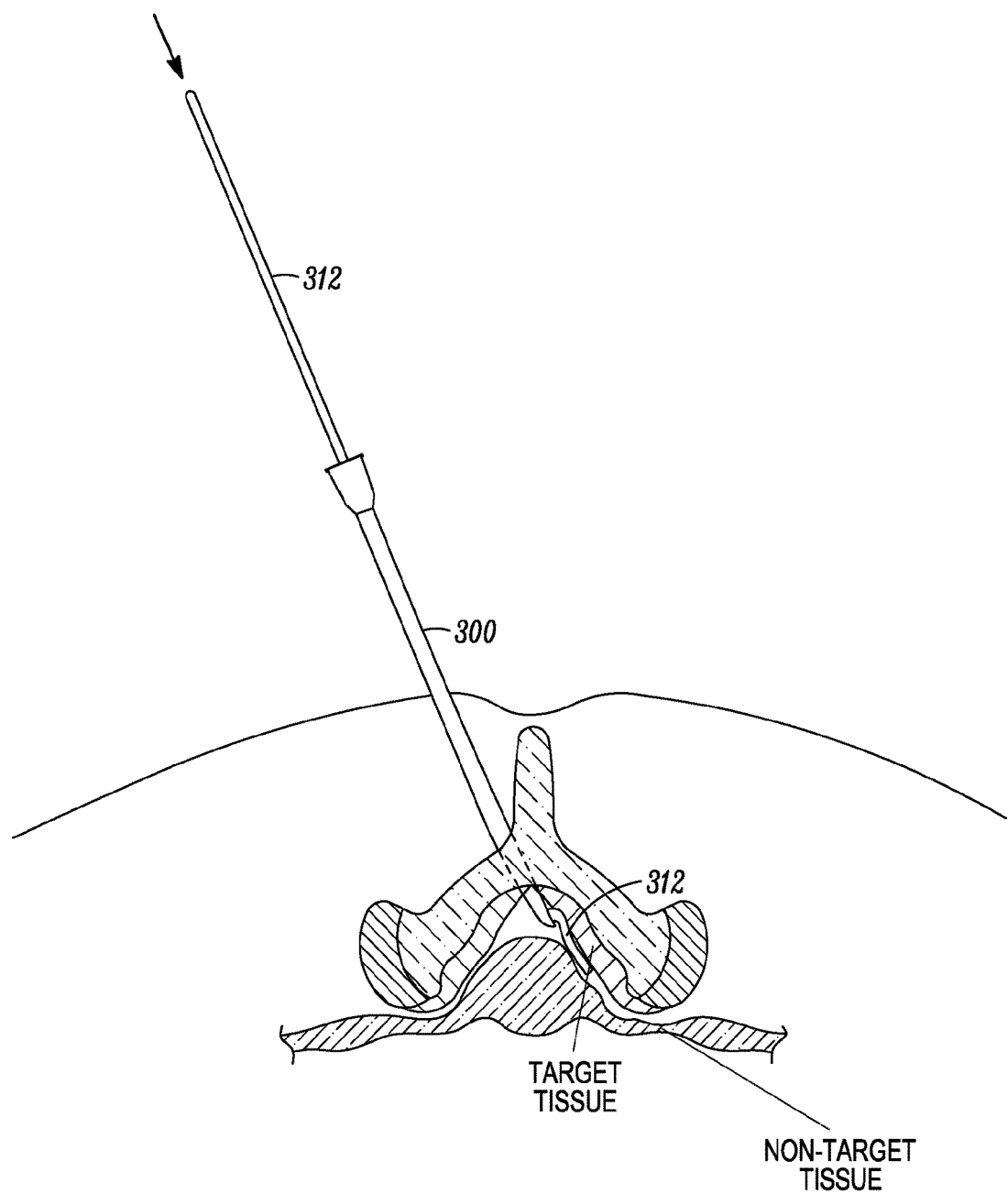
Figure 7H:
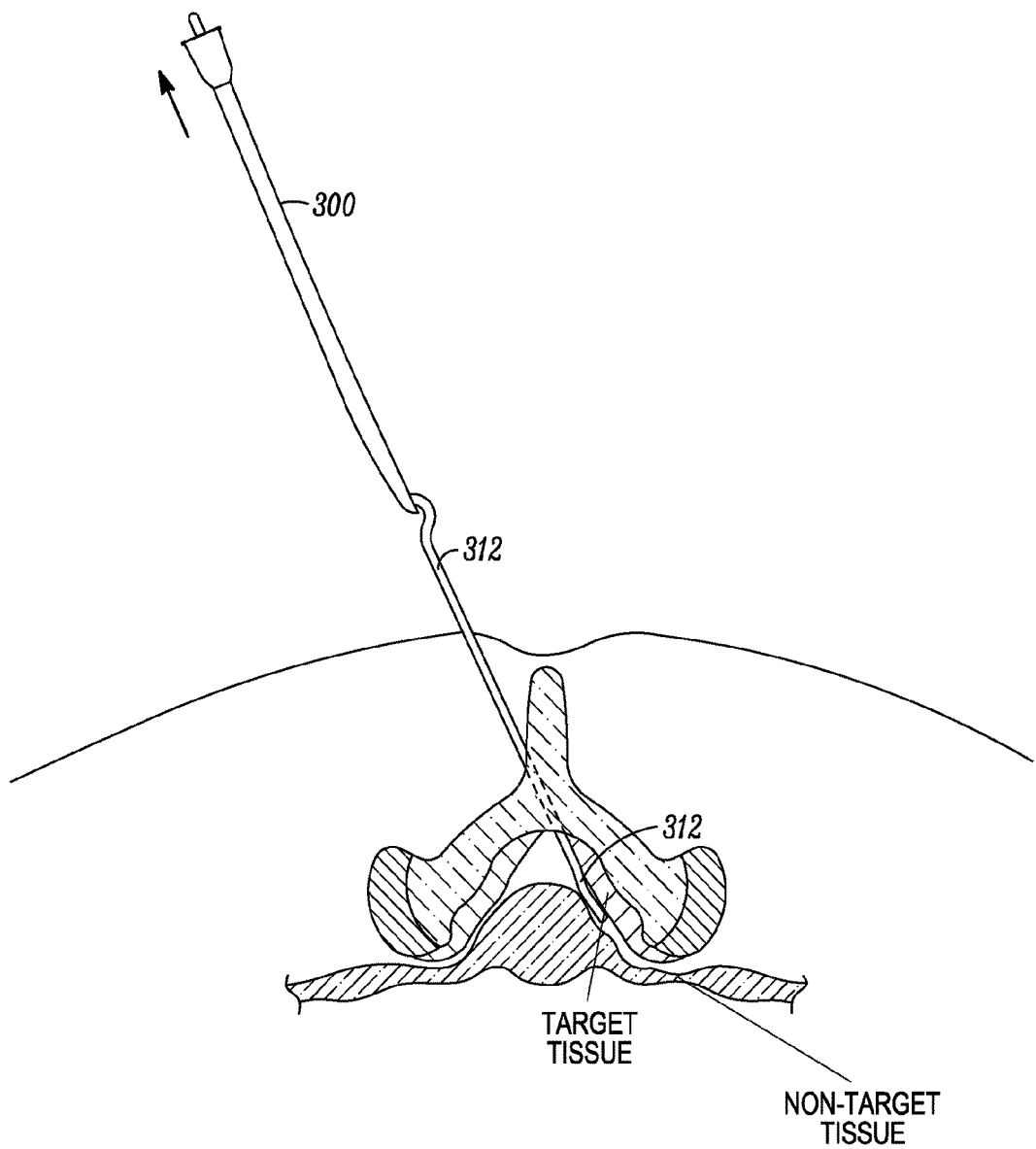
Figure 7I:
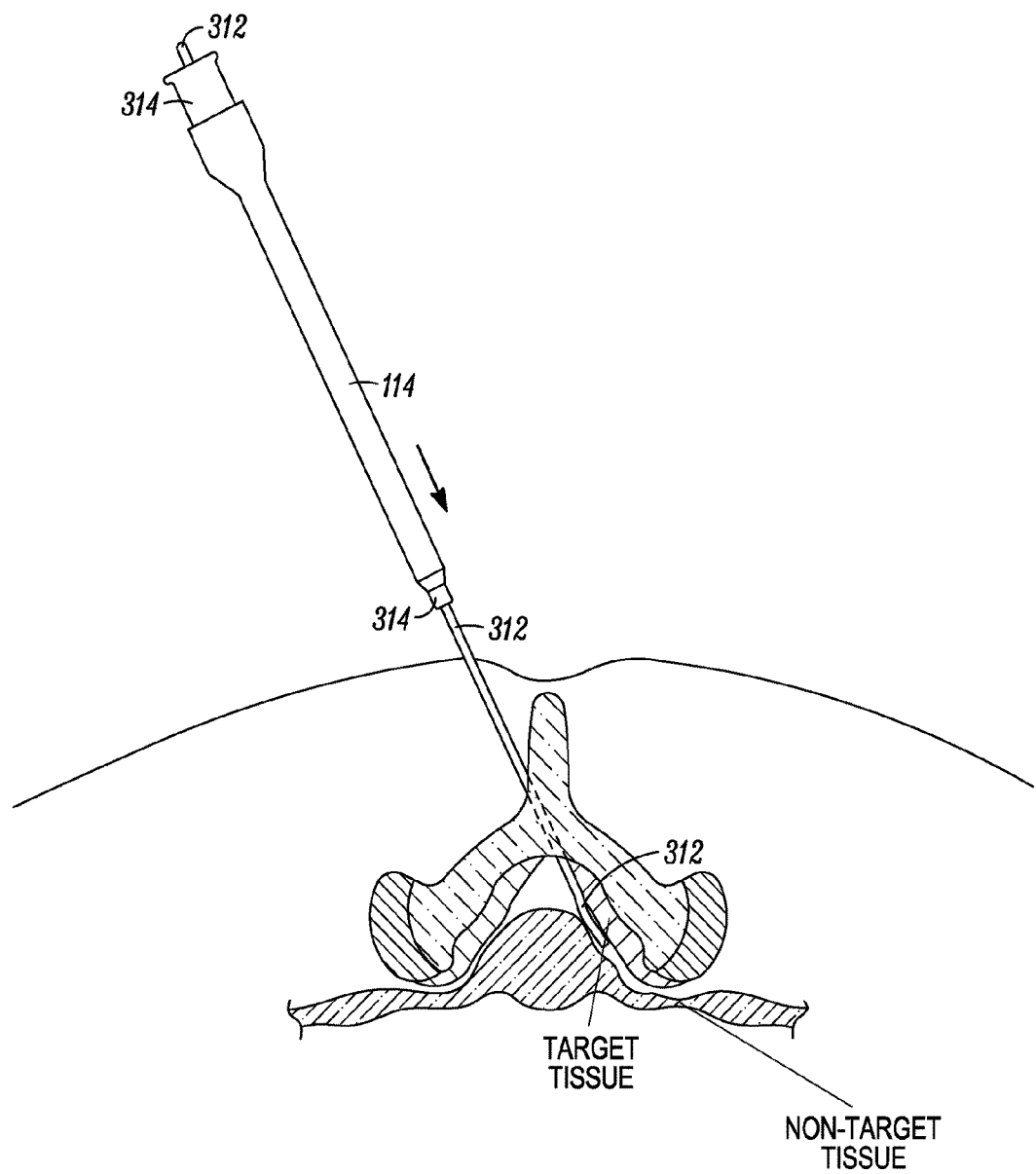
Figure 7J:
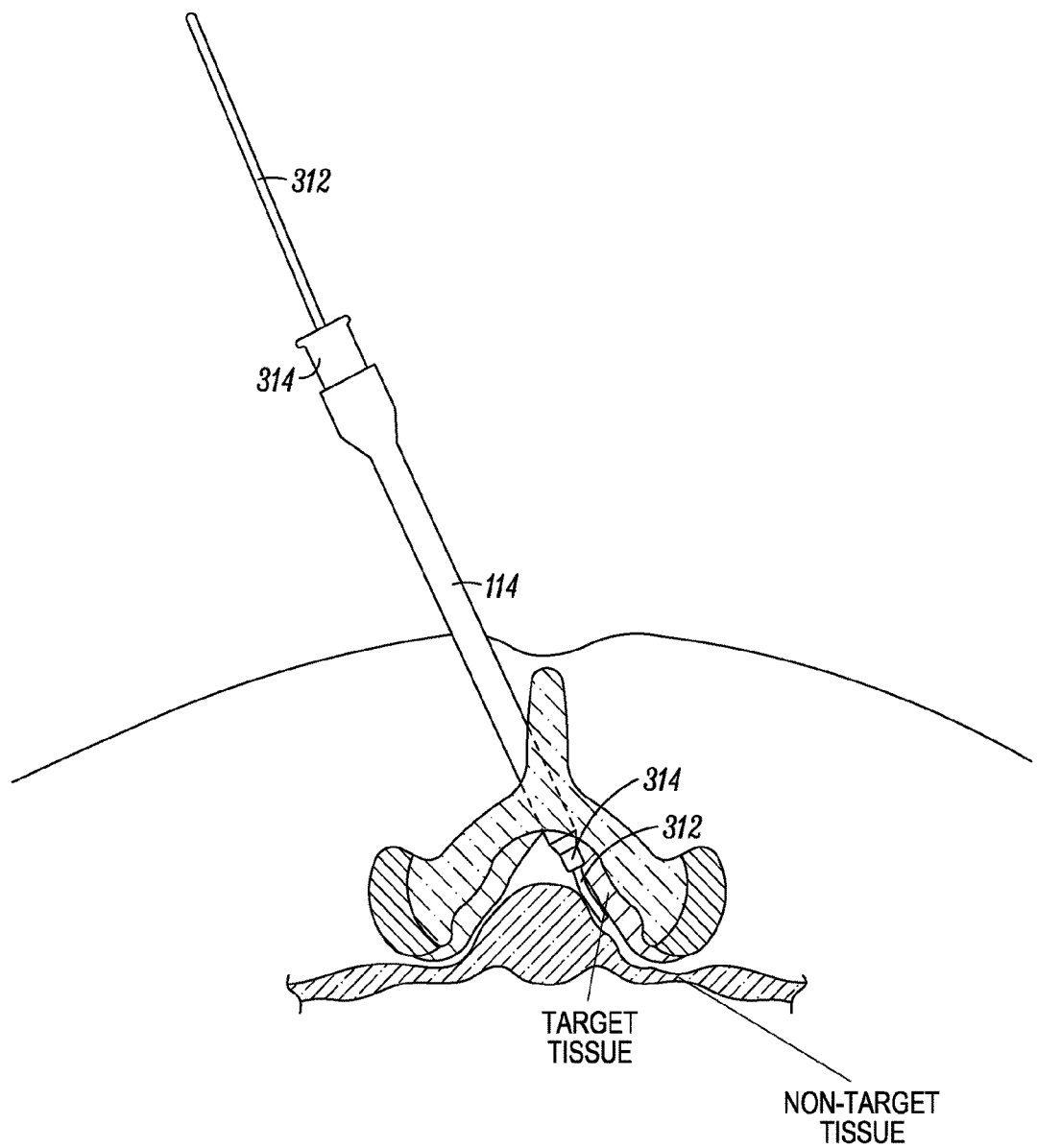
Figure 7K:
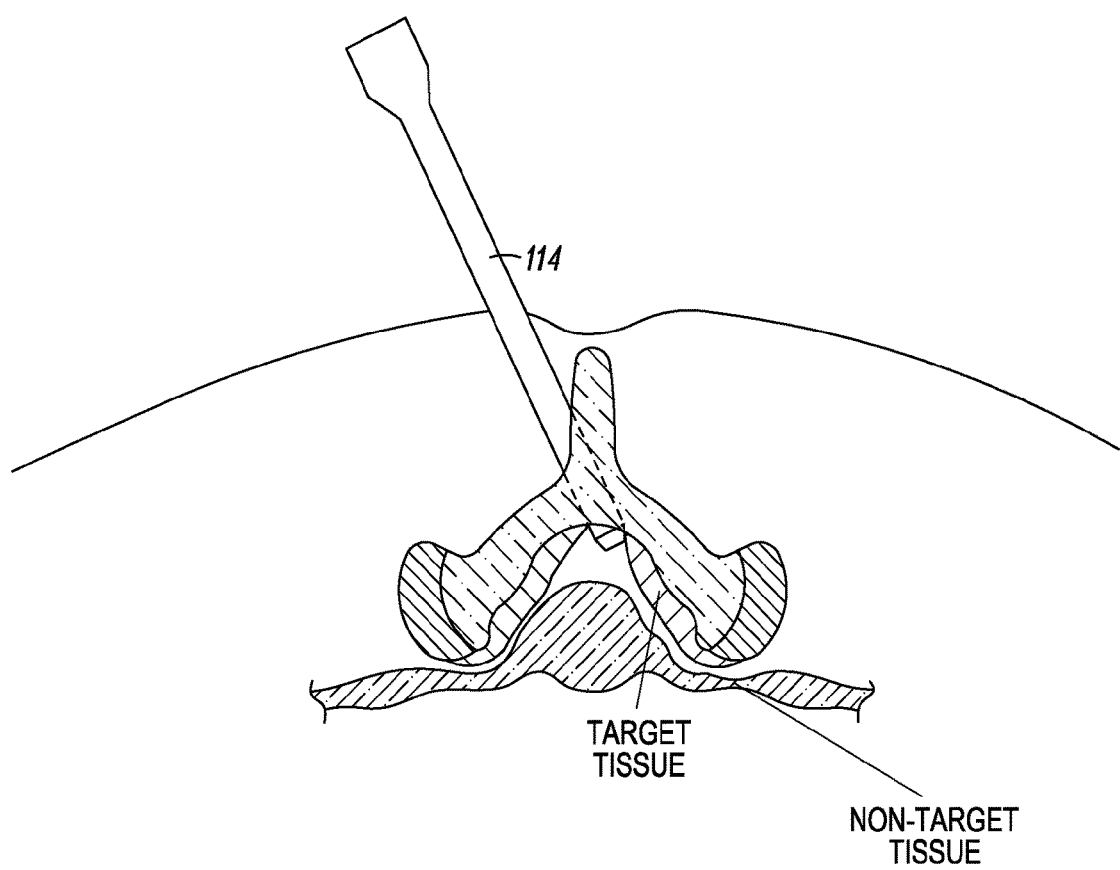
Figure 7L:
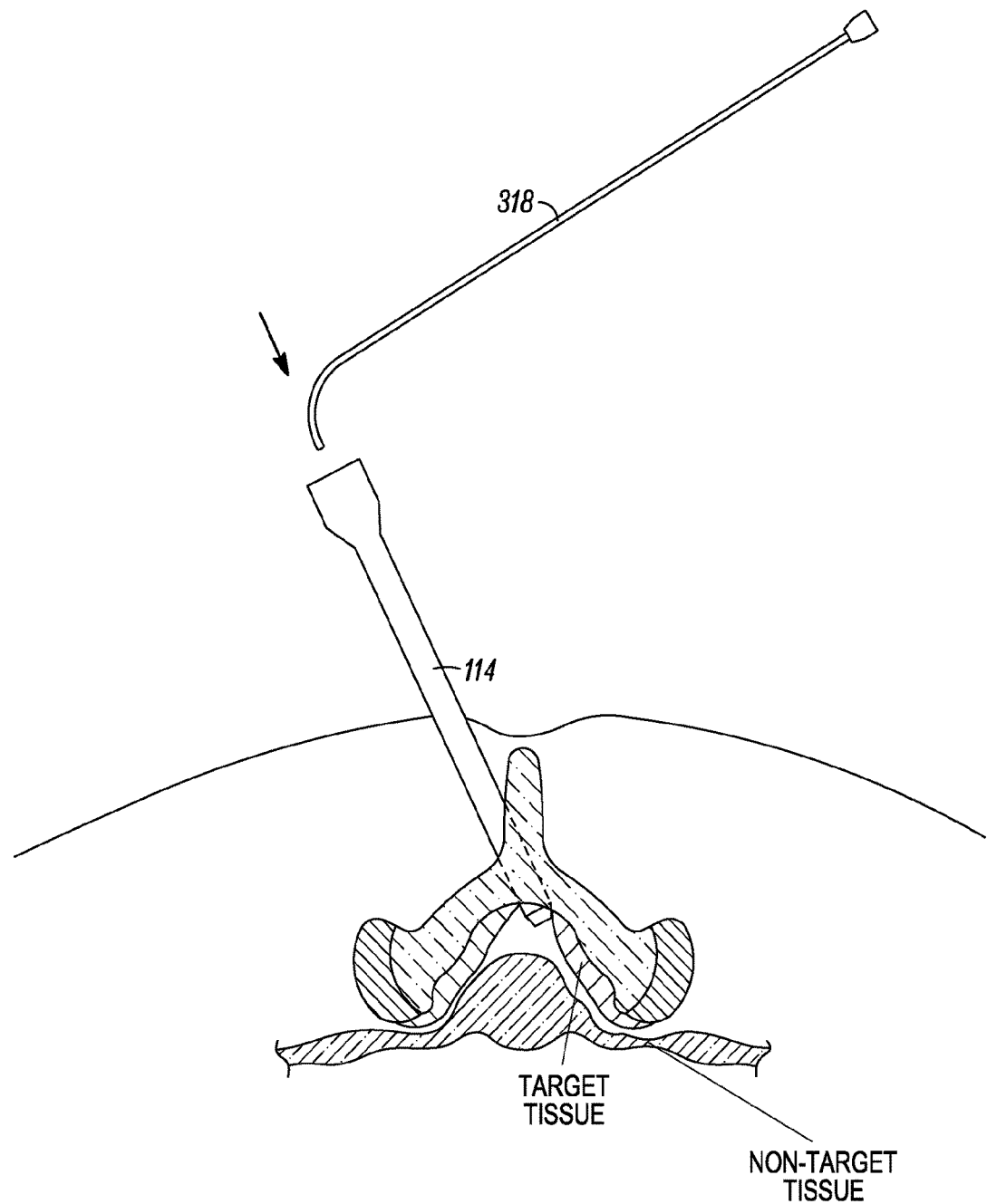
Figure 7M:
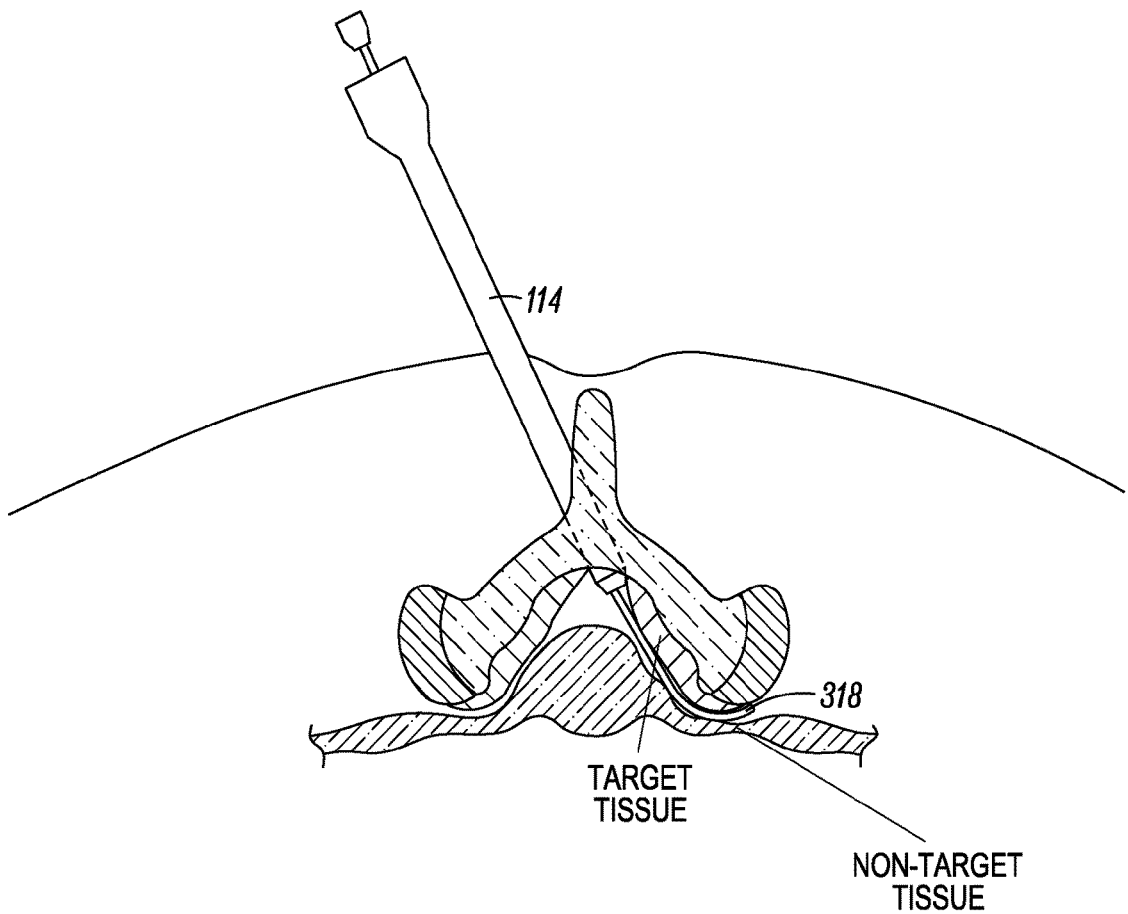
Figure 7N:
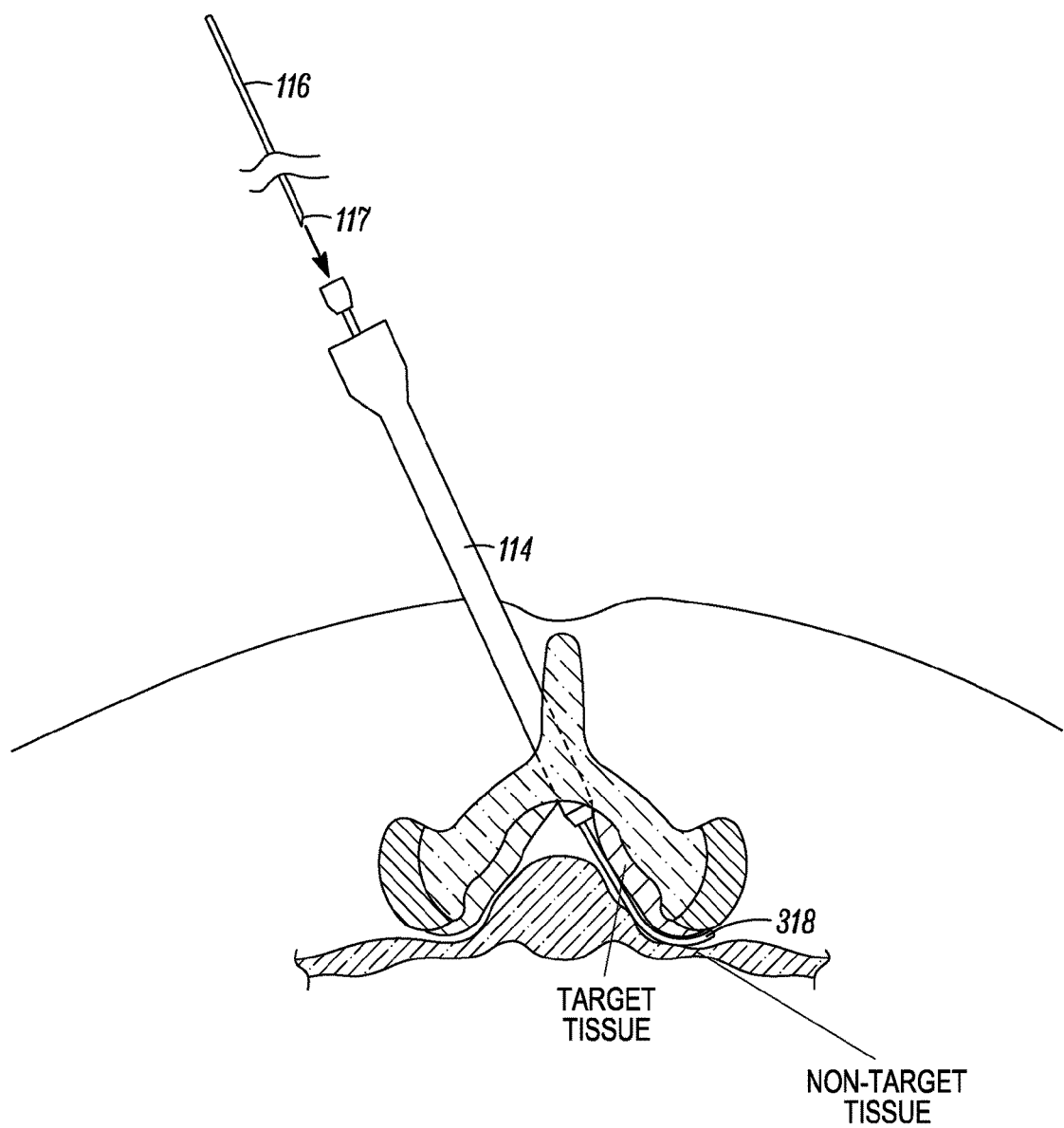
Figure 7O:
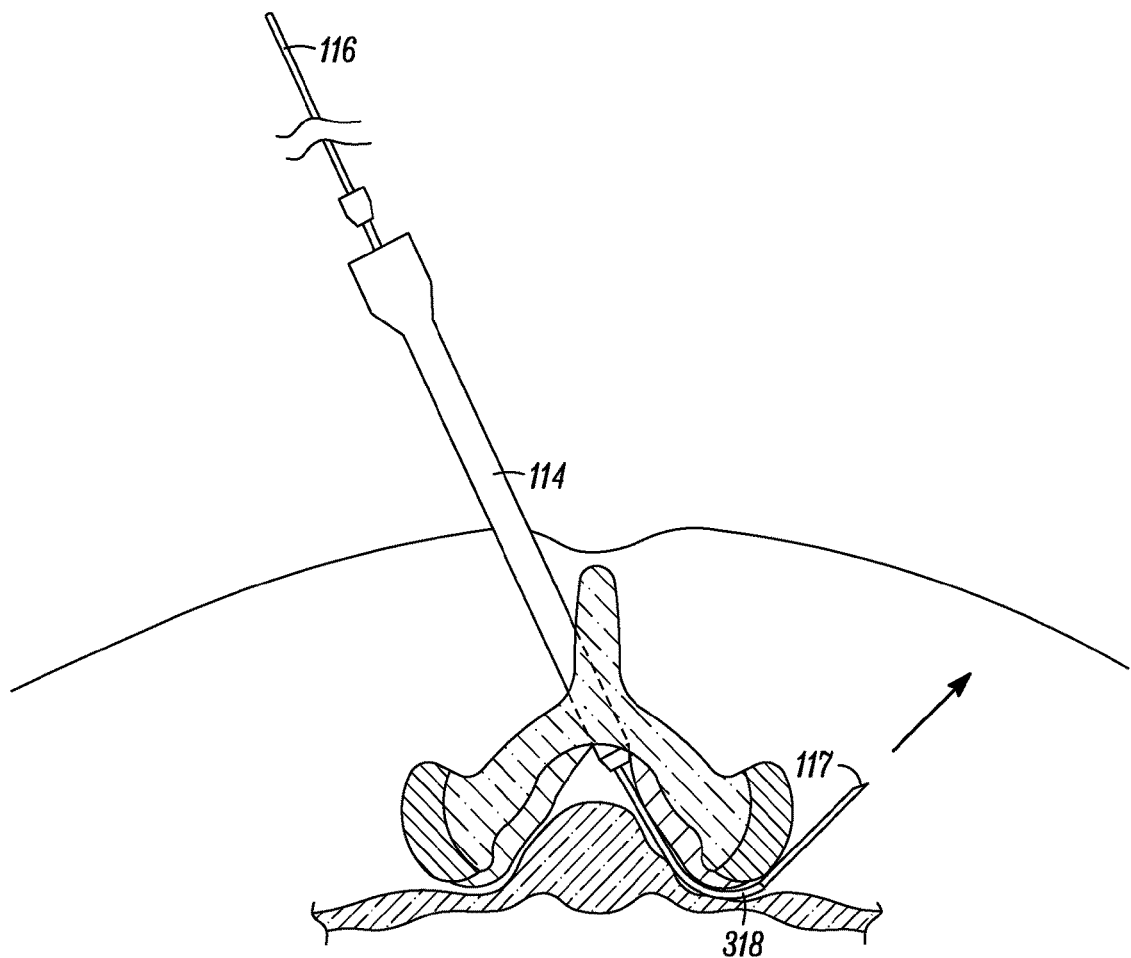
Figure 7P:
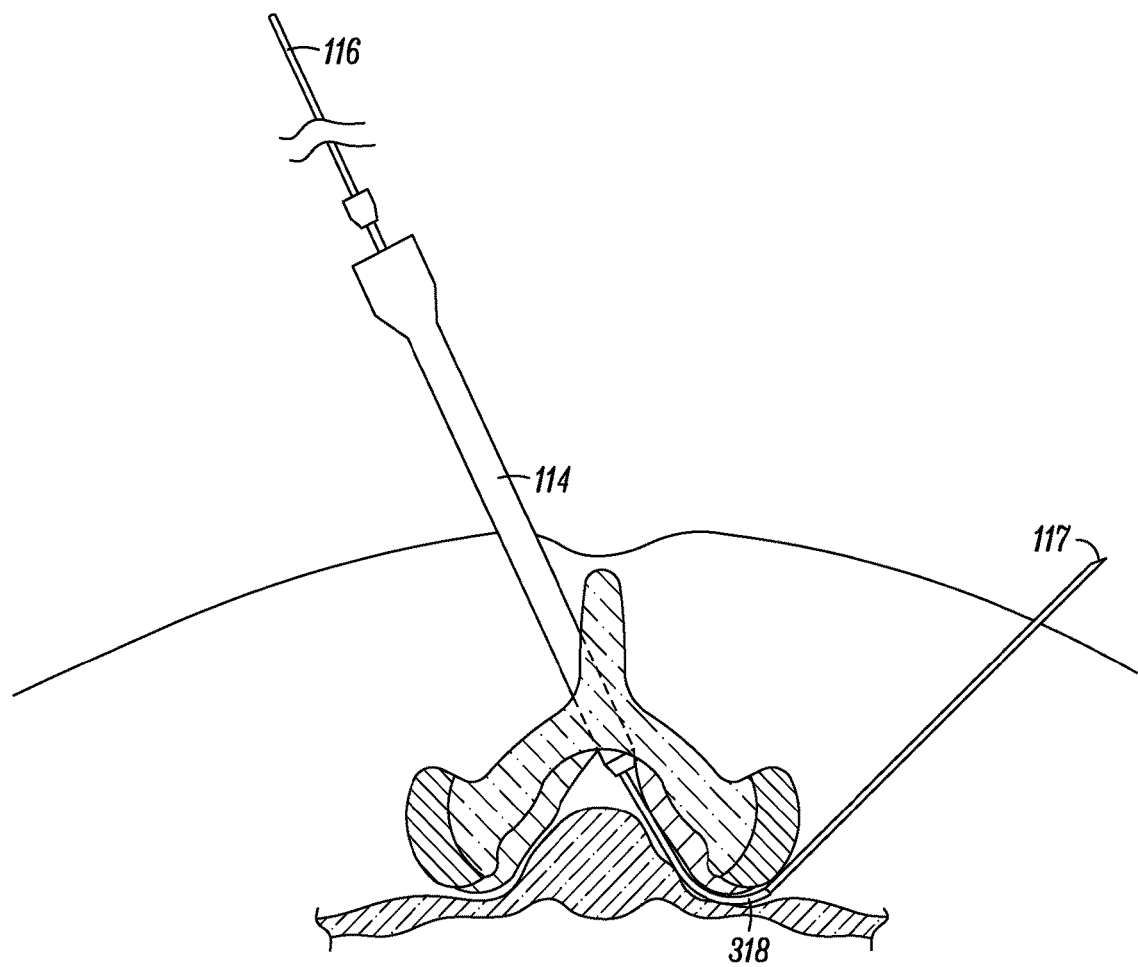
Figure 7Q:
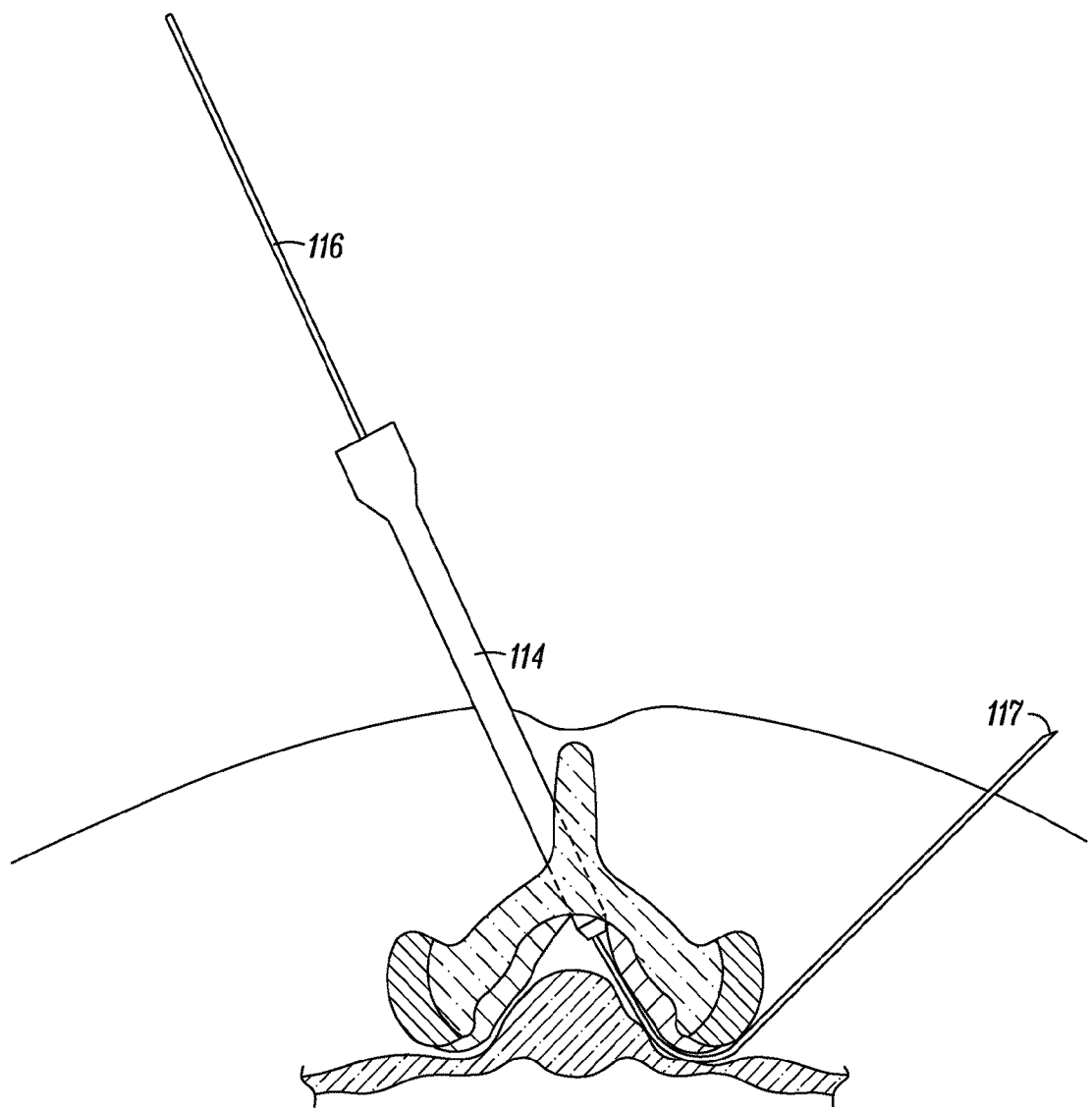
Figure 7R:
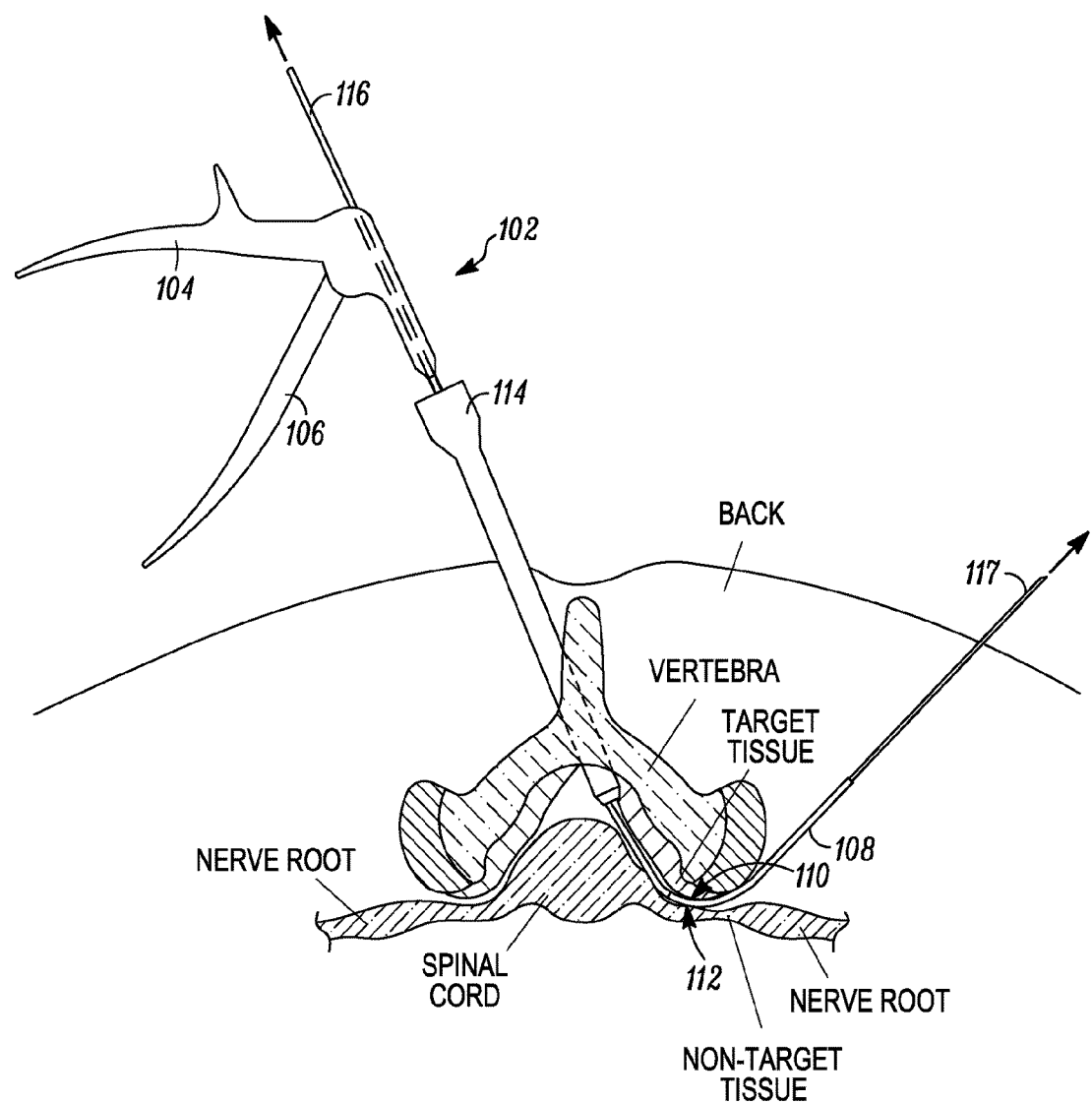
Figure 7S:
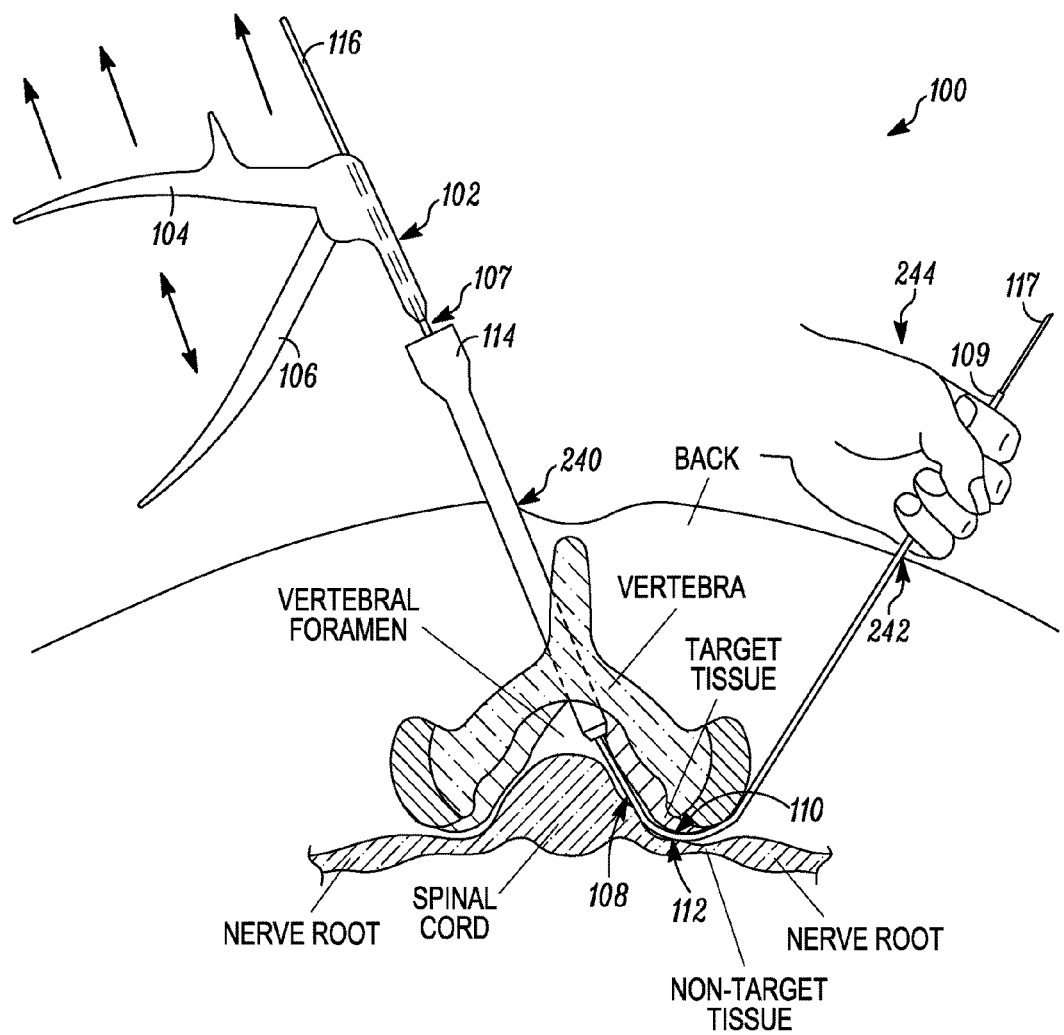

Referring now to FIGS. 7A-7S, a system and method for introducing a tissue modification device into a spine is demonstrated. This system and method may be referred to as an "access system" or "access method," in that they provide or facilitate gaining access to a target tissue to be modified. Of course, the embodiment shown is merely one exemplary embodiment, and any of a number of other suitable methods, devices or systems may be used to introduce one or more devices for modifying tissue in spine. For example, in one alternative embodiment, a spinal tissue modification procedure may be carried out through an open surgical approach. Therefore, the following description is provided primarily for exemplary purposes and should not be interpreted to limit the scope of the invention as it is defined in the claims.

Referring to FIG. 7A, in one embodiment a device delivery method first involves advancing an introducer cannula 300 coupled with a stylet 302 into the patient's back. Cannula 300 and stylet 302 are then passed between adjacent vertebrae and into the ligamentum flavum or an adjacent spinal ligament, as shown further in FIG. 7B. As shown in FIG. 7C, when the distal tip of cannula is positioned as desired, stylet 302 is removed. Referring to FIGS. 7D and 7E, a loss of resistance syringe 304 including a plunger 310, barrel 308 and fluid and/or air 306, is coupled with the proximal portion of cannula 300. The distal portion of cannula 300 is advanced through the ligamentum flavum until it enters the central spinal canal where a loss of resistance to pressure placed on plunger 310 is encountered, and fluid and/or air 306 is injected into central spinal canal to confirm correct placement of cannula 300 as shown in FIG. 7E. Syringe 304 is then removed, as in FIG. 7F, and a guidewire 312 with a non-rigid, atraumatic tip is advanced through cannula 300 into the central spinal canal, as in FIG. 7G. Next, cannula 300 is removed, as in FIG. 7H, leaving behind guidewire 312. As shown in FIGS. 7I and 7J, an introducer sheath 114, coupled with a dilator 314, is then advanced over guidewire 312 to position a distal portion of sheath 114 at a desired location within the spine. Dilator 314 and guidewire 312 are then removed, as in FIG. 7K.

Once introducer sheath 114 is in place, one or more curved or steerable guide devices 318 may be advanced through it to desired positions in and/or through the spine, as shown in FIGS. 7L and 7M. One or more guide members 116, may then be advanced through guide device 318, as shown in FIGS. 7N-7P. In some embodiments, guide member 116 may comprise a guidewire having a beveled tip 117 to facilitate passage of guidewire 116 through tissue (FIG. 7O). Also in some embodiments, passing guidewire 116 through guide device 318 may partially straighten the distal portion of guide device 318. Finally, guide device 318 may be removed, as in FIG. 7Q, and elongate body 108 of tissue modification device 102 may be advanced over guide member 116 and through introducer sheath 114 to a desired position in the spine, as in FIG. 7R. In an alternative embodiment, guidewire 116 may be coupled with tissue modification device 102 at or near its distal end and used to pull tissue modification device 102 into a desired position. As shown in FIG. 7S, elongate body 108 may be tensioned to urge tissue modifying members 110 against target tissue, as shown with arrows at opposite ends of device 102, while distal portion 109 is anchored, in this case by hand 244. In an alternative embodiment, guide member 116 may be tensioned to urge tissue modifying members 110 against target tissue as shown in FIG. 7R.

Once tissue modification device 102 is in a desired position, tissues which may be modified in various embodiments include, but are not limited to, ligament, tendon, tumor, cyst, cartilage, scar, "bone spurs," inflammatory and bone tissue. In some embodiments, modifying the target tissue reduces impingement of the tissue on a spinal cord, a branching nerve or nerve root, a dorsal root ganglia, and/or vascular tissue in the spine. Actuator 106 on handle 104 may be activated to modify target tissue using tissue modification member(s) 110, while elongate body 108 may be held relatively stable by hand 244 and by tension force applied to handle 104.

In various embodiments, the system and method described immediately above may include additional features or steps, may have fewer features or steps, may have an alternate order of implementation of steps, or may have different features or steps. For example, in some embodiments placement of device 102 will be performed in a medial-to-lateral direction (relative to the patient), while in alternative embodiments device placement will be performed lateral-to-medial. In some embodiments, one or more components of the system described may be anchored to the patient, such as guide member 116 or introducer sheath 114. In various embodiments, one or more guide members 116 may include one or more wires, rails or tracks and may be inserted through guide device 318, introducer sheath 114 without guide device 318, cannula 300, an epidural needle, a lumen of an endoscope, a lumen of a tissue shield or barrier device, a curved guide device 318 placed through a lumen of an endoscope, or the like. In other embodiments, for example, guide device 318 may be placed through introducer cannula 300 and then introducer sheath 114 may be passed over guide device 318. Tissue modification device 102 may similarly be inserted with or without using any of these devices or components in various combinations. Various guidewires 312, guide devices 318 and/or guide members 116 may be pre-shaped to have one or more curves, may be steerable, and/or may include one or more rails, tracks, grooves, lumens, slots, partial lumens, or some combination thereof.

In some embodiments, tissue modification device 102 may be inserted through one or more hollow devices as described above (such as introducer sheath 114, as shown, or cannula 300 in an alternative embodiment) in such a way that device 102 expands upon extending out of a distal portion of the hollow delivery device, thereby assuming a wider profile for modifying a greater amount of target tissue from a single location. In an alternative embodiment, device 102 may retain the same overall profile during insertion and during use. In some embodiments, one or more delivery devices may remain in the patient during use of tissue modification device 102, while in alternative embodiments, all delivery devices may be removed from the patient when tissue modification device 102 is operating. In some embodiments, tissue modification device 102 may be slidably coupled with one or more delivery devices during delivery and/or during use. In one embodiment, tissue modification device 102 may be advanced through introducer sheath 114, and sheath 114 may be used as an irrigation and evacuation lumen to irrigate the area of the target tissue and evacuate removed tissue and other debris, typically by applying a vacuum. In alternative embodiments, tissue modification device 102 may include an irrigation and/or evacuation lumen to irrigate an area of the target tissue and evacuate removed tissue and other debris.

Some embodiments of an access system for facilitating tissue modification may further include one or more visualization devices (not shown). Such devices may be used to facilitate placement of the access system for introducing the tissue modification device, to facilitate tissue modification itself, or any combination of these functions. Examples of visualization devices that may be used include flexible, partially flexible, or rigid fiber optic scopes, rigid rod and lens endoscopes, CCD (charge-coupled device) or CMOS (complementary metal-oxide semiconductor) chips at the distal portion of rigid or flexible probes, LED illumination, fibers or transmission of an external light source for illumination or the like. Such devices may be slidably couplable with one or more components of an access system or may be slidably or fixedly coupled with a tissue modification device. In other embodiments, additional or alternative devices for helping position, use or assess the effect of a tissue modification device may be included. Examples of other such devices may include one or more neural stimulation electrodes with EMG or SSEP monitoring, ultrasound imaging transducers external or internal to the patient, a computed tomography (CT) scanner, a magnetic resonance imaging (MRI) scanner, a reflectance spectrophotometry device, and a tissue impedance monitor disposed across a bipolar electrode tissue modification member or disposed elsewhere on a tissue modification device or disposed on the access system.

Figure 8A:
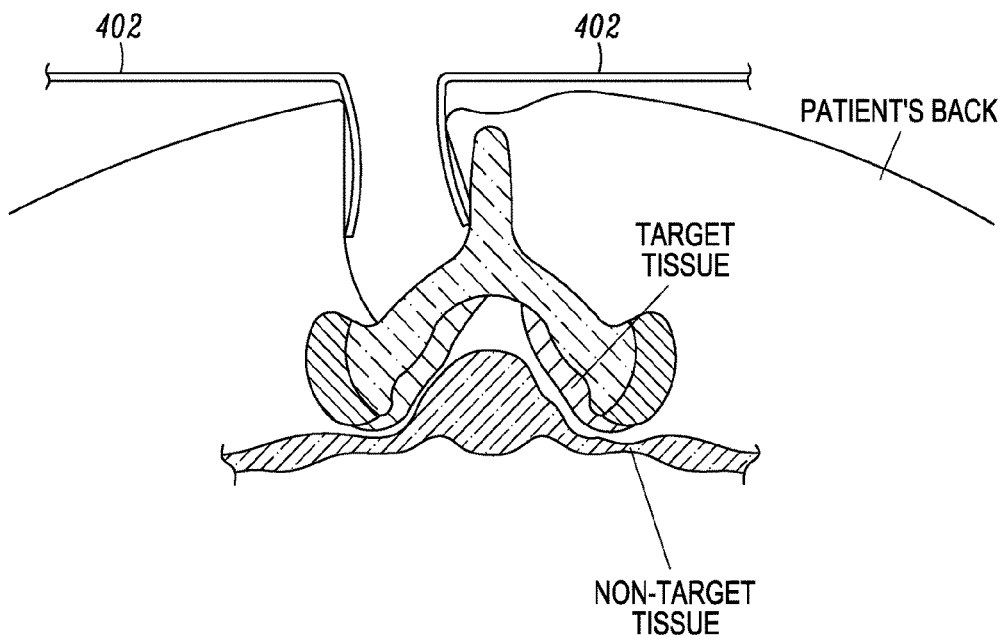
FIGS. 8A-8F are cross-sectional views of a portion of a patient's spine and back, demonstrating a method for introducing apparatus for modifying spinal tissue to an area in the spine for performing the tissue modification according to an alternative embodiment of the present invention.
Figure 8B:
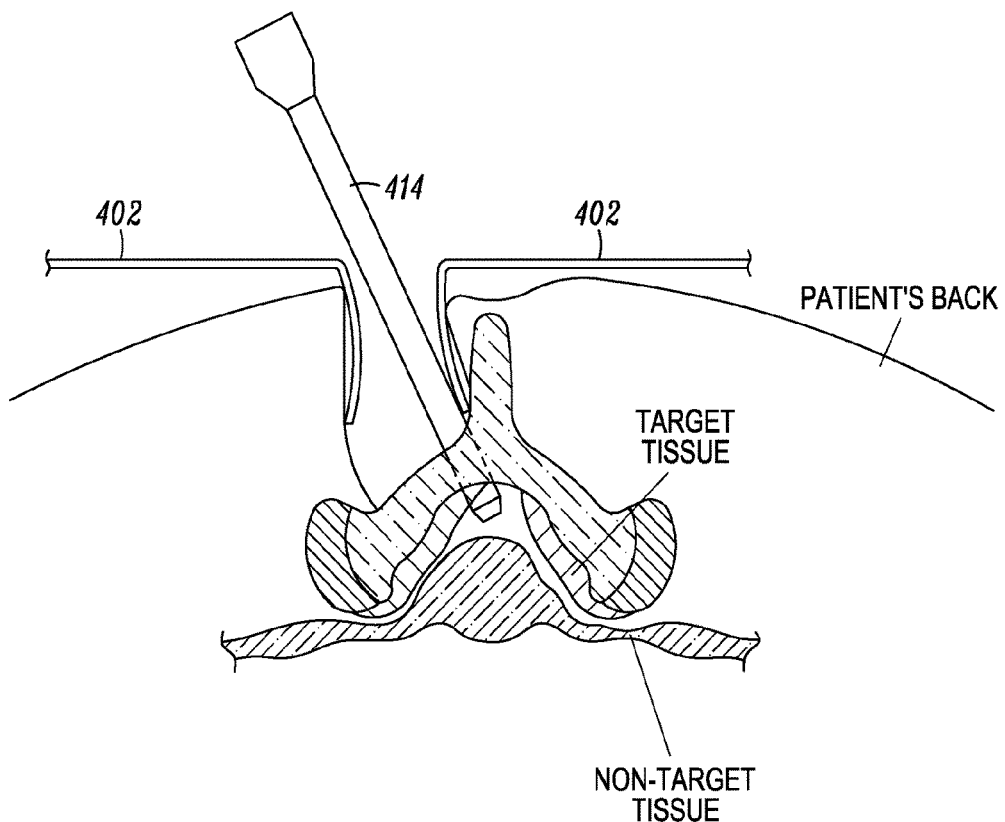
Figure 8C:
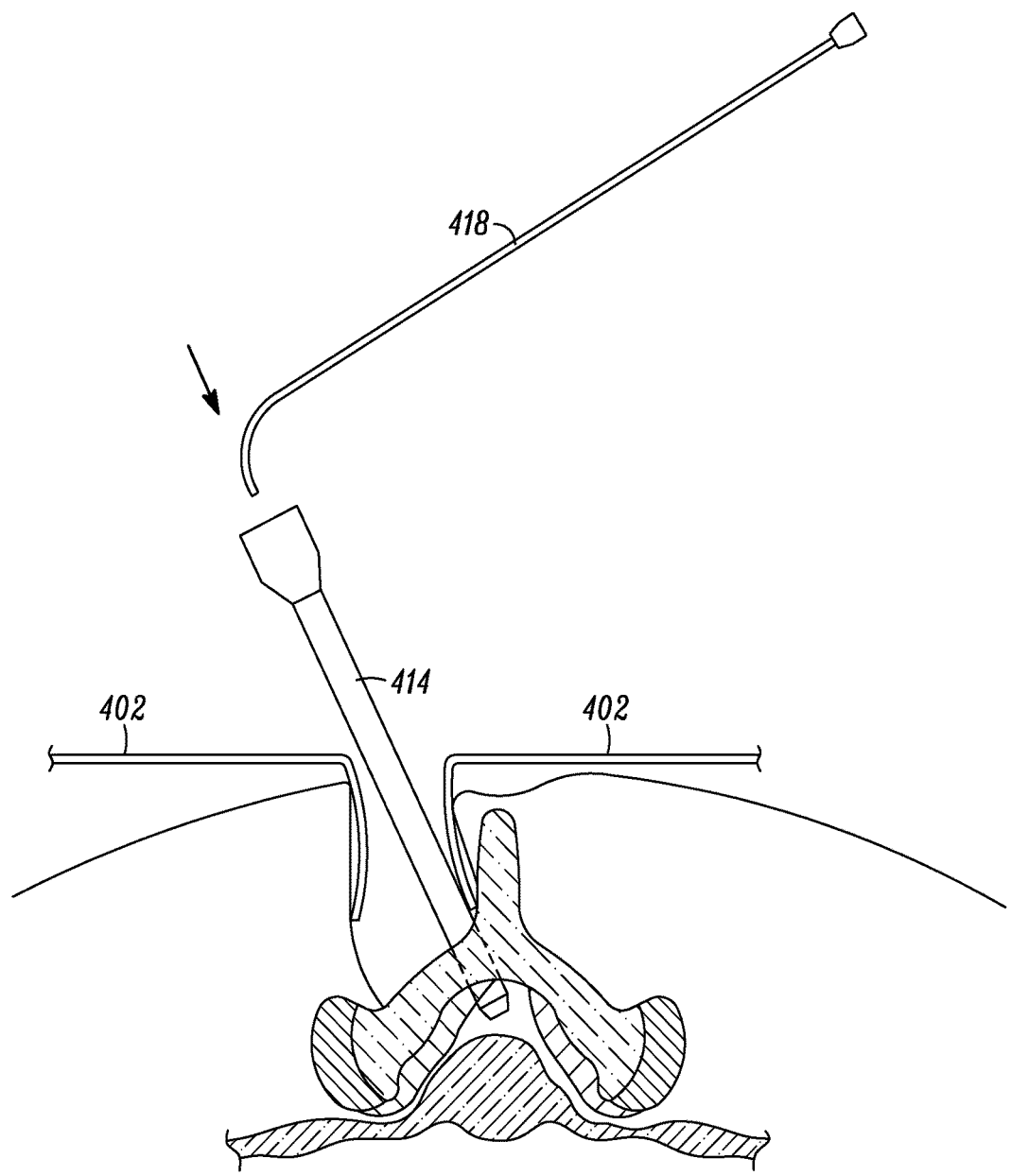
Figure 8D:
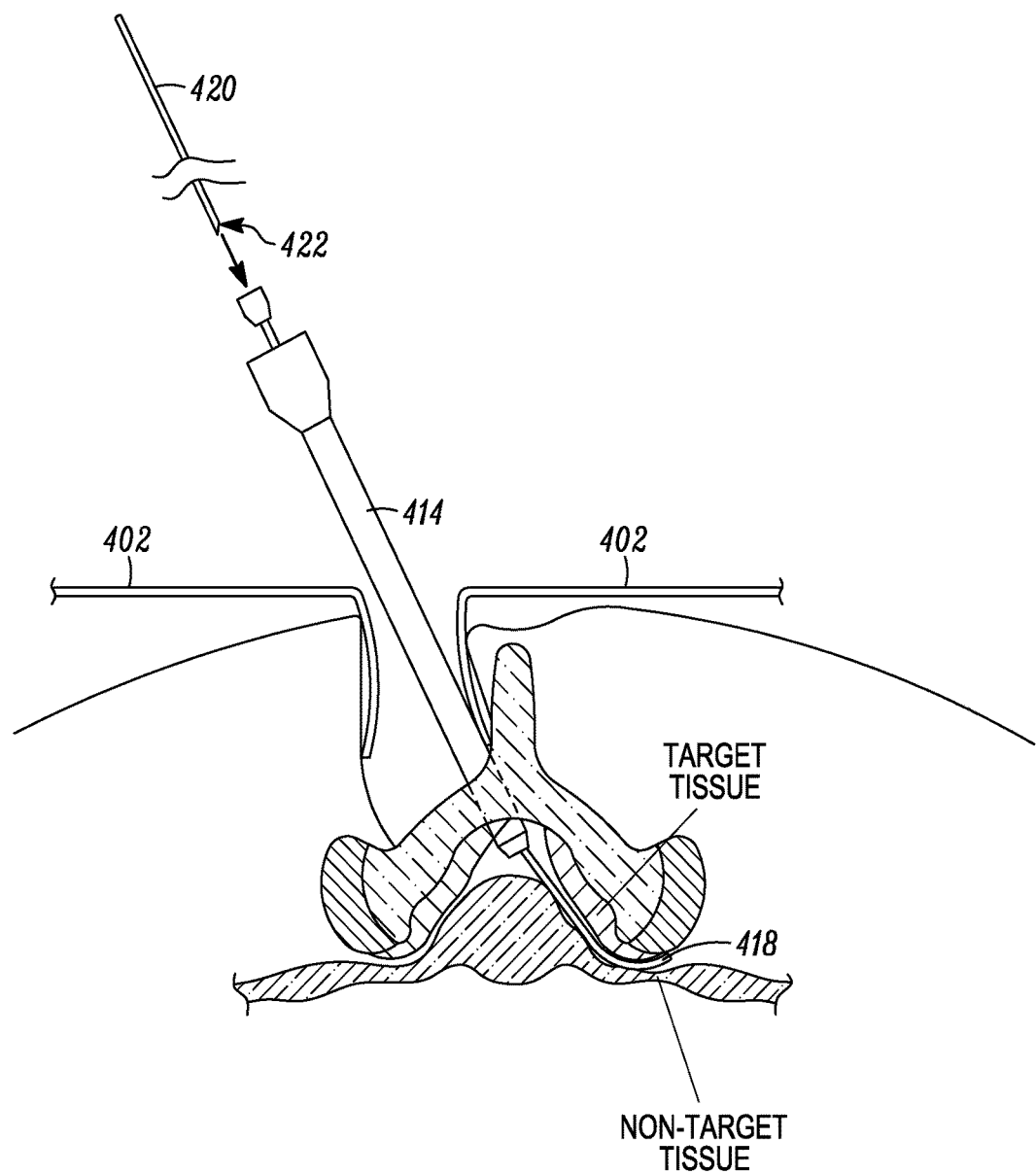

Referring now to FIGS. 8A-8E, in an alternative embodiment, a tissue modification device and optionally one or more introduction/access devices may be positioned in a patient using an open surgical technique. As shown in FIG. 8A, for example, in one embodiment an open surgical incision is made on a patient's back, and two retractors 402 are used to expose a portion of the patient's vertebra. As shown in FIG. 8B, an introducer sheath 414 may then be inserted through the incision, between retractors 402. As in FIG. 8C, a curved guide device 418 may then be inserted through introducer sheath 414. Guide device 418 extends into the epidural space and through the intervertebral foramen as shown in FIG. 8D.

In some embodiments, a curved and cannulated thin, blunt probe may be placed directly through the open incision into the epidural space of the spine, or alternatively may be placed through introducer sheath 414. The probe tip may be advanced to or through a neural foramen. Such a probe may be similar in shape, for example, to a Woodson elevator, Penfield 3, hockey stick probe, ball tipped probe, or the like. In alternative embodiments, probes that may be manually bent to change their shapes, or probes with articulating tips, or probes with shape lock portions, and/or probes having grooves instead of cannulas may be used.

Figure 8E:
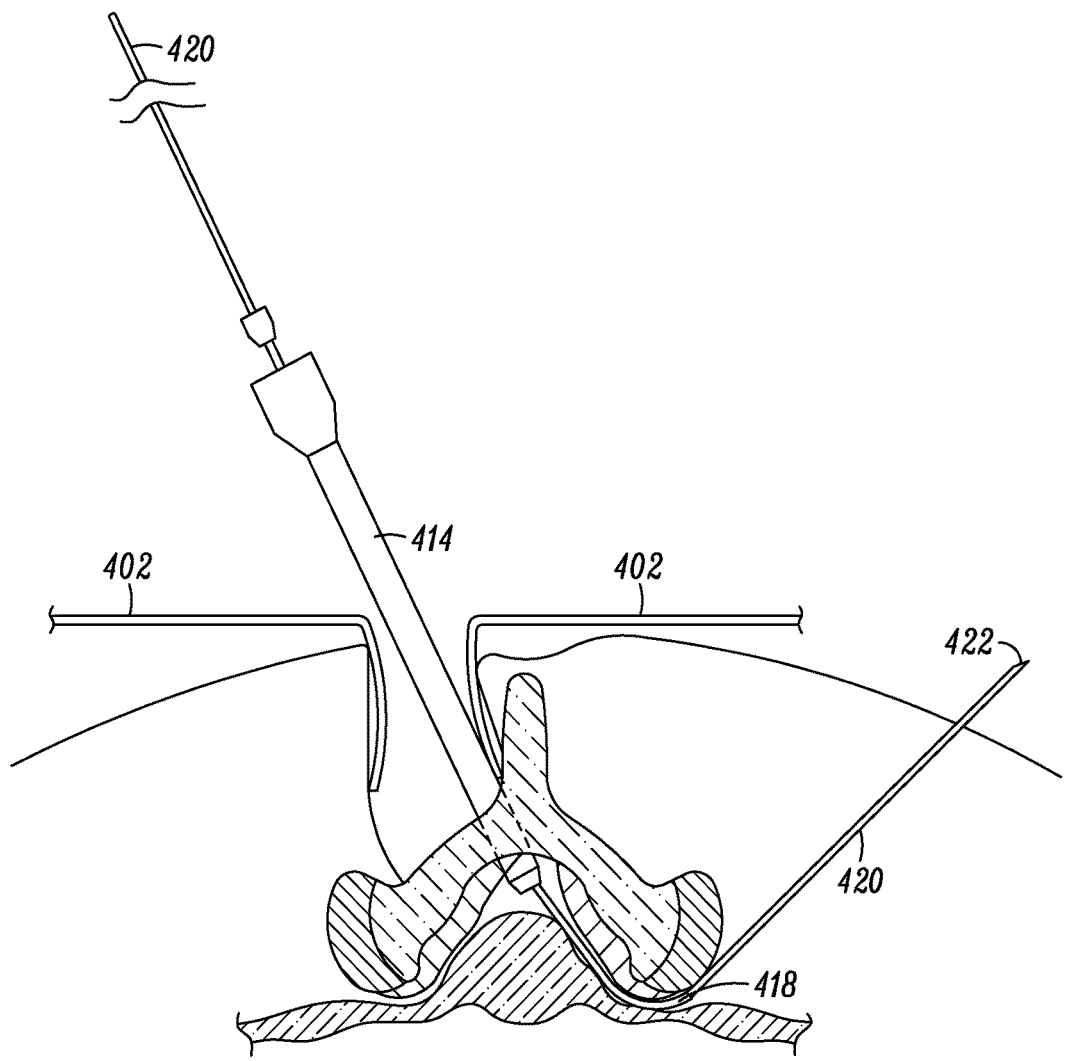

As shown in FIGS. 8D-8E, a substantially straight, flexible guidewire 420 with a sharp tip 422 may then be inserted through curved guide device 418 and advanced so that its distal portion with sharp tip 422 extends outside the patient's back at a location separate from the open incision (FIG. 8E).

Figure 8F:
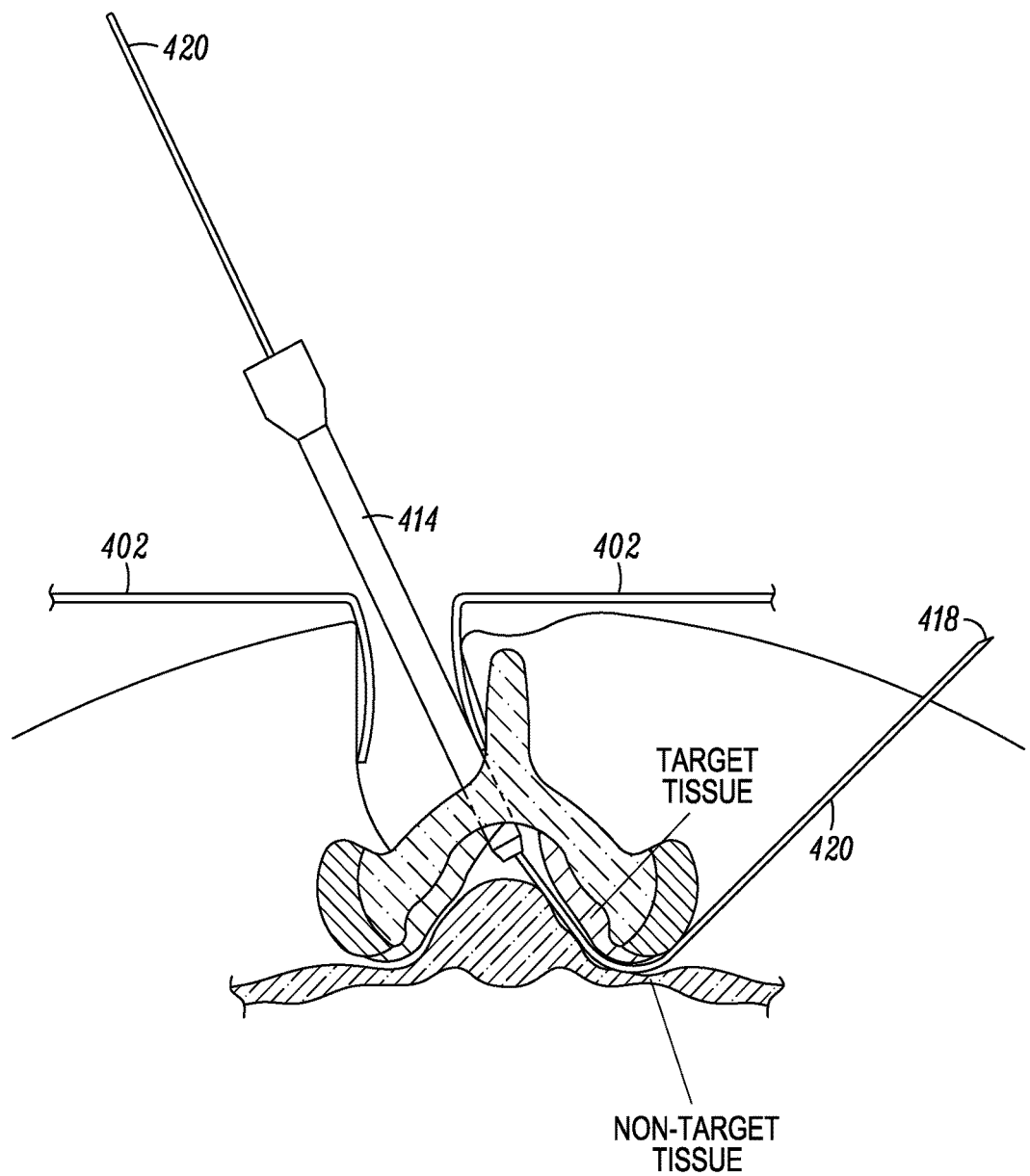

Guide device 418 may then be removed, as in FIG. 8F, and in subsequent steps a tissue modification device may be inserted over guide wire 420 and through introducer sheath 414 and used to modify tissue as described in more detail above. In an alternative embodiment, a curved, flexible cannula may be inserted through the curved guide device, until it extends lateral to the neural foramen, after which a substantially straight, flexible guidewire with a sharp tip may then be inserted through curved cannula and advanced so that its distal portion with sharp tip extends outside the patient's back.

Figure 9A:
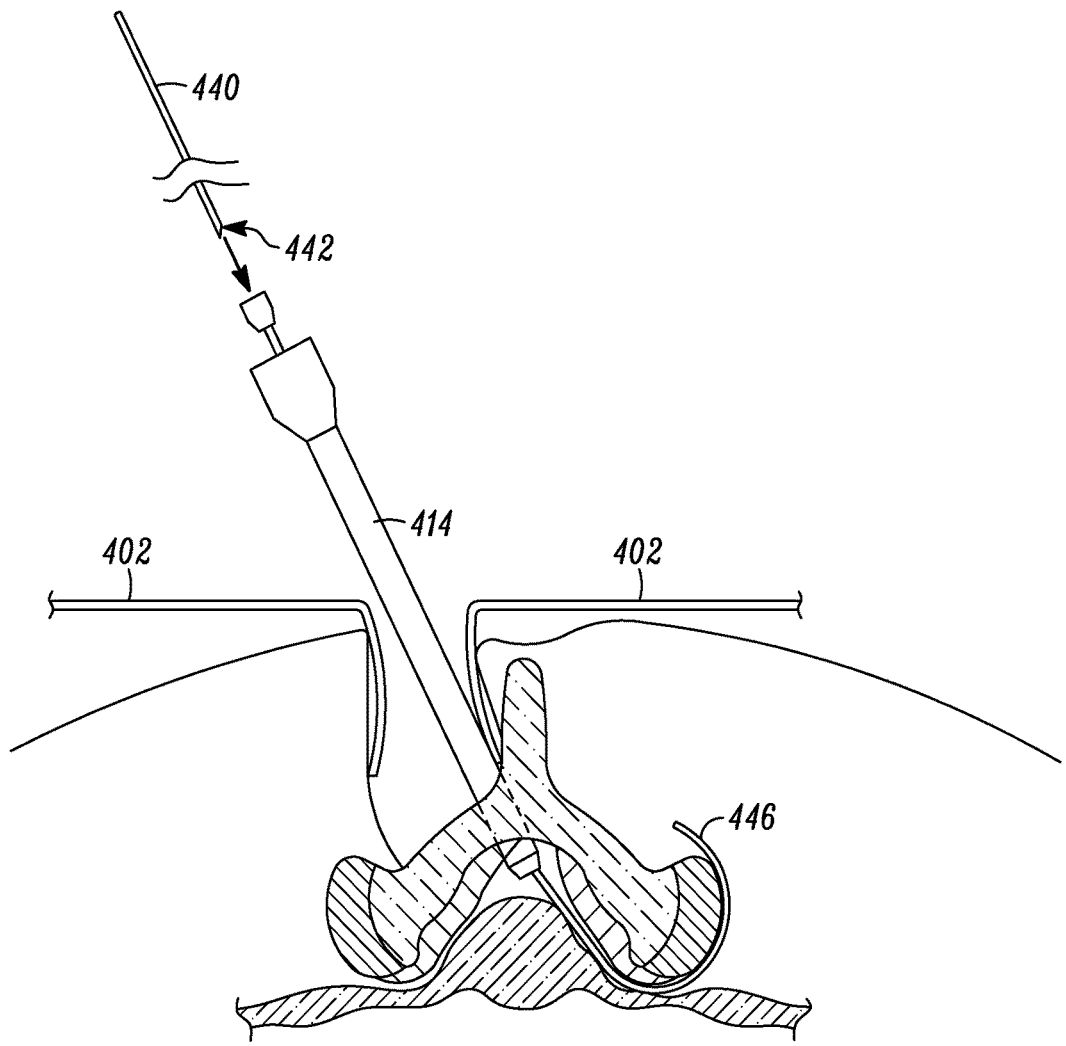
FIGS. 9A-9B are cross-sectional views of a portion of a patient's spine and back, demonstrating a method for introducing apparatus for modifying spinal tissue to an area in the spine for performing the tissue modification according to an alternative embodiment of the present invention.
Figure 9B:
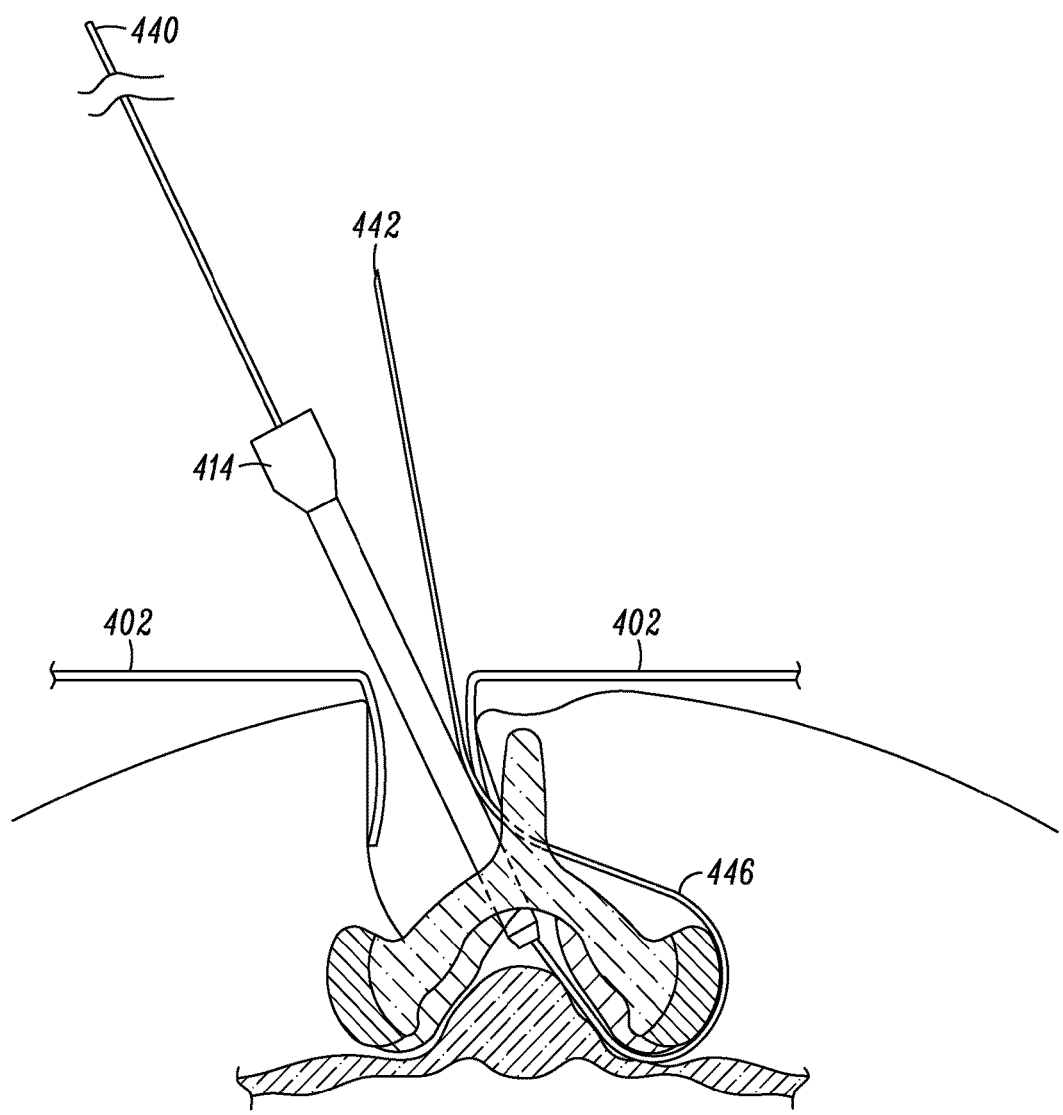

Referring now to FIGS. 9A and 9B, another alternative open surgical access method is shown. In FIG. 9A, a curved guide device 446 is shown in place through the epidural space and intervertebral foramen, and a guidewire 440 with a beveled distal tip 442 is about to be advanced through guide device 446. As shown in FIG. 9B, in this embodiment, guidewire 440 is directed by guide device 446 back through the open incision through which the various access devices are introduced. In such an embodiment, then, only one incision is created and the proximal and distal portions of one or more devices extend out of the patient's back through the same incision.

In various alternative embodiments, open surgical access may be through exposure down to a vertebral lamina, through ligamentum flavum without lamina removal, through ligamentum flavum with partial or complete lamina removal, through ligamentum flavum with or without lamina removal with partial or complete medial facet joint removal, through open exposure and out through skin laterally, through open exposure and back out through the open exposure, or through a lateral open exposure that accesses the neural foramen from the lateral side. One or more visualization devices may be used with open surgical access procedures as well as with percutaneous or other less invasive procedures. In another alternative embodiment (not shown), a tissue modification device may be placed in the patient directly, without any introduction devices.

With reference to FIGS. 1A-10F, an alternative method and apparatus for obtaining access to the neural foramen utilizing an open surgical approach are described. Similar methods and apparatus are described in U.S. patent application Ser. Nos. 11/251,205 (FIGS. 26-27 and accompanying description) and 60/681,719, which were previously incorporated by reference.

FIGS. 10A and 10B illustrate two alternative embodiments of an access device 84, 85. In one embodiment (FIG. 10A), access device 84 may comprise a cannulated probe 86, illustratively an elevator probe having a first lumen 88 and a second lumen 90. In one embodiment, a visualization element 92, such as an epidural endoscope, may be advanced through or coupled to first lumen 88 (or alternatively second lumen 90) to provide visualization at the distal tip of probe 86.

In an alternative embodiment (FIG. 10B), an access device 85 may comprises a probe 87 and a single lumen 89. Visualization device 92, as well as a cannula 94 or curved guidewire (shown in later figures), may be advanced through lumen 89, either in parallel or in sequence. Alternatively, visualization device 92 may be omitted or may be attached directly to probe 87. In various embodiments, access device 84, 85 may comprise any desired number of lumens 88, 89, 92.

Figure 10C:
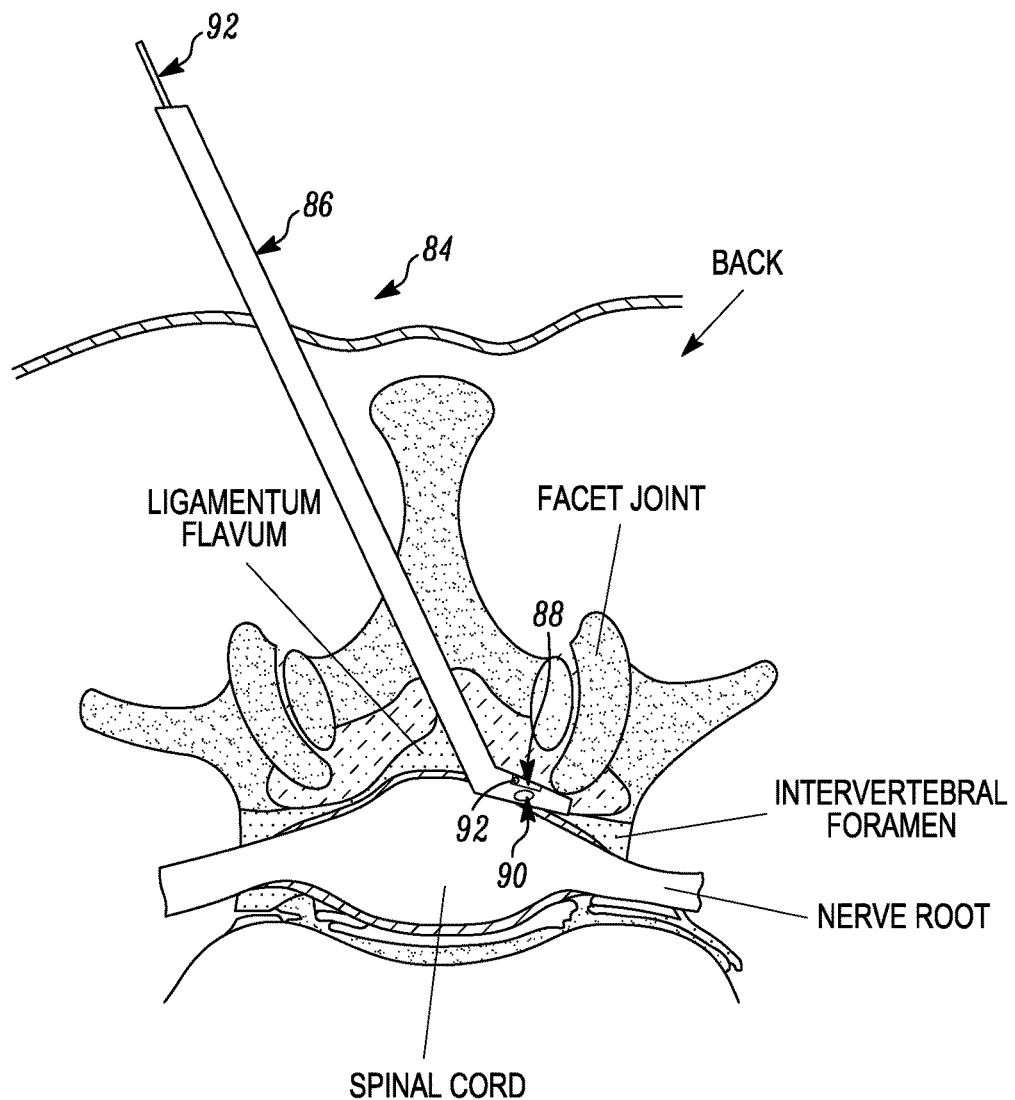
FIGS. 10C-10F illustrate a method of placing a guidewire between tissues using the access probe device shown in FIG. 10A according to one embodiment of the present invention.

In one embodiment, and with reference now to FIG. 10C, the dual lumen embodiment of access device 84 may be passed through a surgical incision or cut-down to position its distal end in proximity to an intervertebral (or "neural") foramen while under optional visualization via visualization device 92. Visualization may facilitate access via a minimally invasive or keyhole surgical cut-down and may also facilitate a fully open approach. Direct visualization alternatively or additionally may be utilized. In some embodiments, as described in greater detail below, probe 86 may include one or more electrodes at or near upper and/or lower surfaces of its distal end. Such electrodes may be used to test for proper placement of probe 86 above the nerve root and/or cauda equine or spinal cord.

Figure 10D:
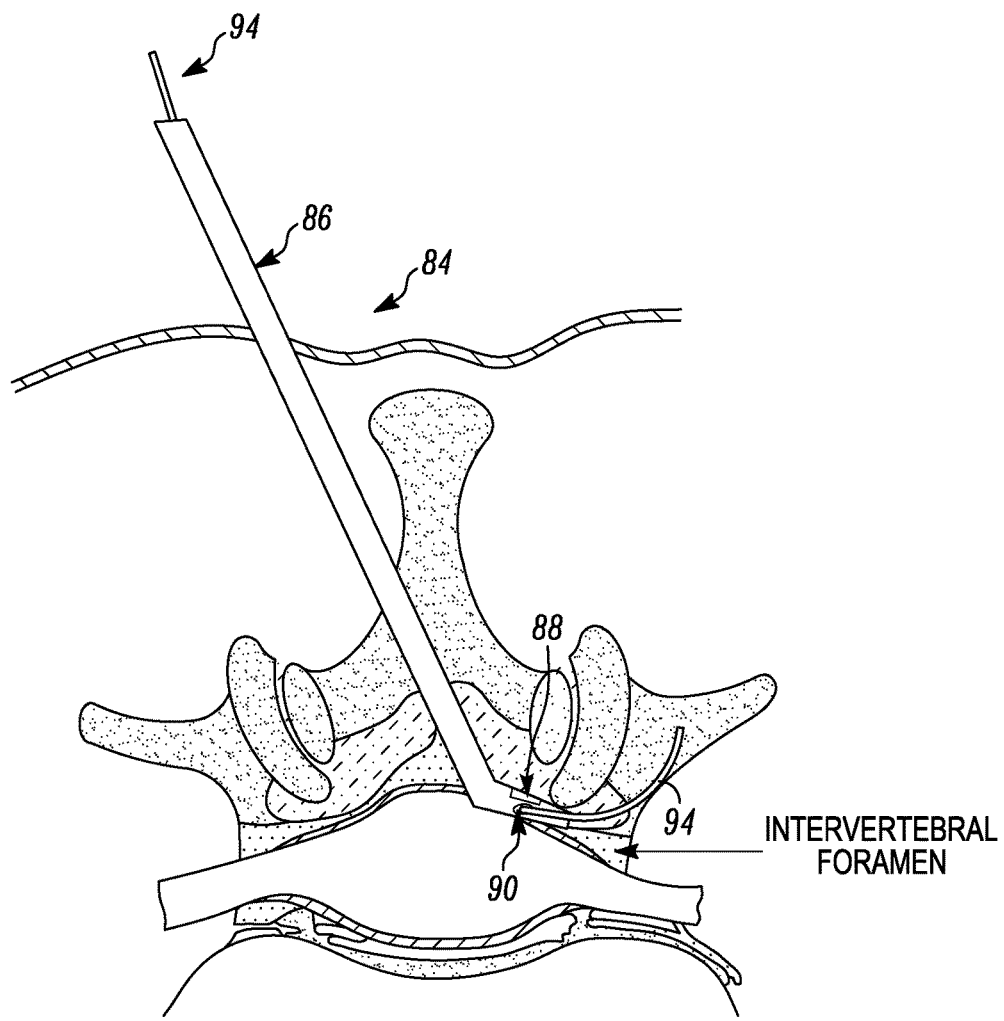

As seen in FIG. 10D, with probe 86 properly positioned, an atraumatic curved tube, introducer or cannula 94 may be advanced through either lumen 88, 90 of probe 86 and driven laterally to cannulate the intervertebral foramen. In some embodiments, visualization device 92 may be removed from probe 86, as shown in FIG. 10D, while in other embodiments device 92 may remain in one of lumens 88, 90. Cannula 94 optionally may be configured to deliver a stimulation waveform at or near its distal tip for monitoring proximity to the nerve root during cannulation of the foramina with the cannula.

Figure 10E:
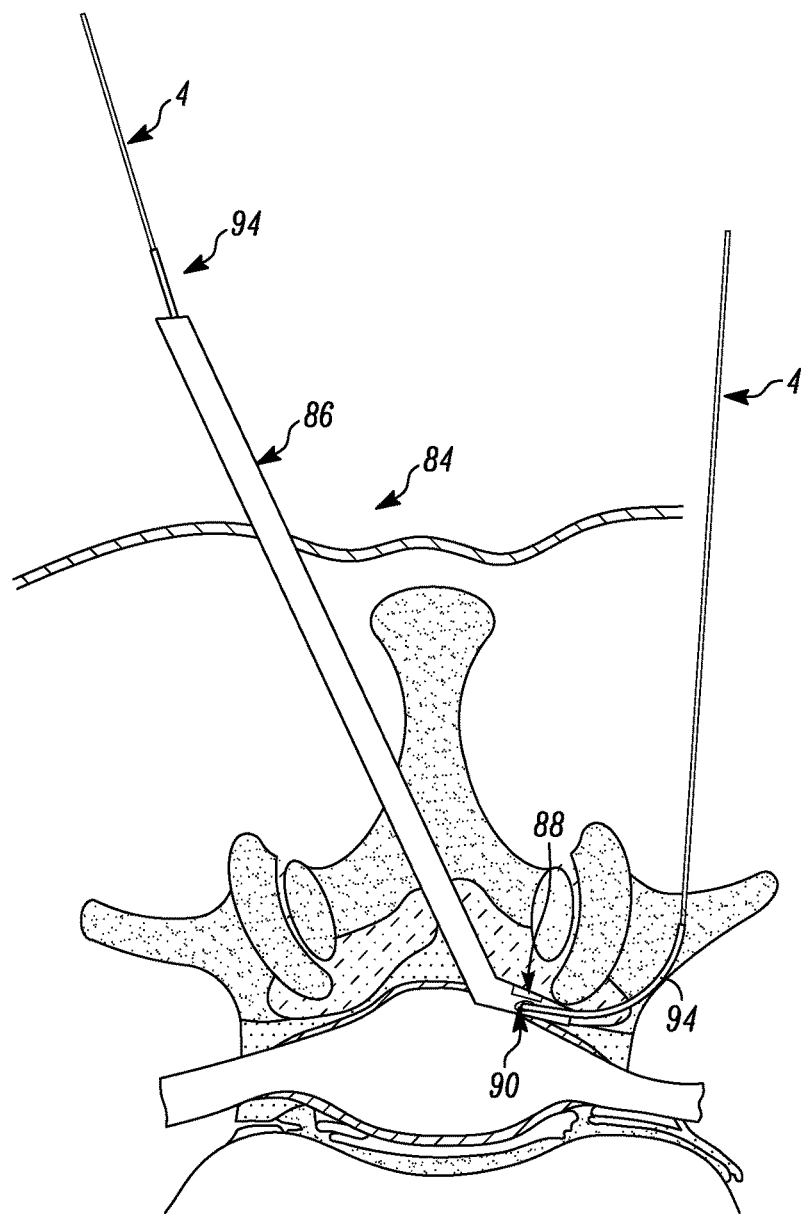
Figure 10F:
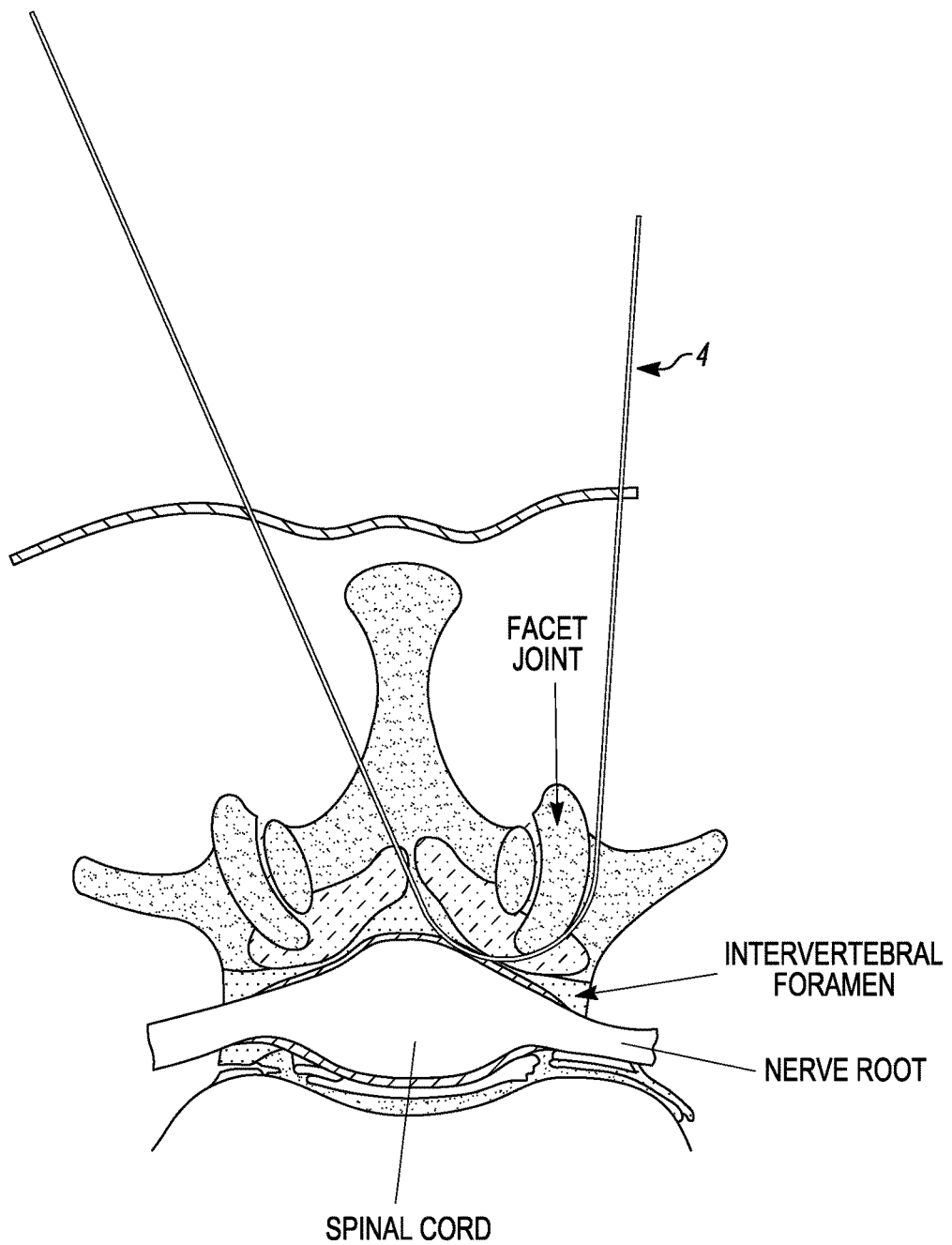

As seen in FIG. 10E, once access device 84 is in a desired location, in one embodiment a straight, flexible guidewire 4 or needle, which optionally comprises a sharpened tip, may be advanced through cannula 94 and driven posteriorly through the skin of the patient's back. Alternatively, a second surgical incision and or cut-down may be formed at or near the exit of the intervertbral foramen for grasping guidewire 4 and pulling it through. As shown in FIG. 10F, with access guidewire 4 positioned through and across the intervertebral foramen, probe 86 may be removed. This leaves guidewire 4 in place to provide access for any other suitable device or devices, such as a tissue modification device.

Figure 11A:
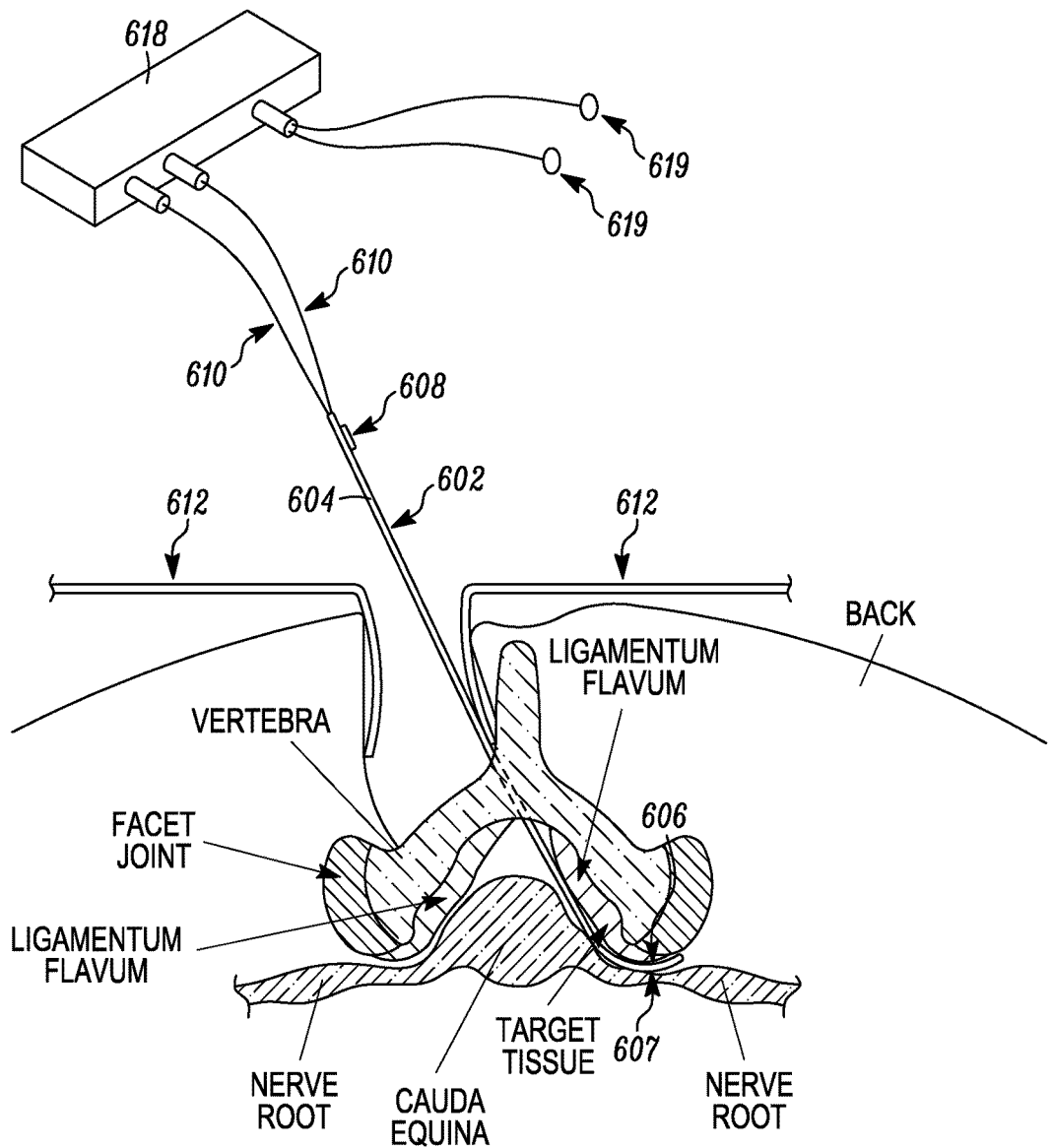
FIGS. 11A-11E are cross-sectional views of a portion of a patient's spine and back, demonstrating a method for introducing a guidewire and a tissue modification device between target and non-target tissue in the spine according to one embodiment of the present invention.
Figure 11B:
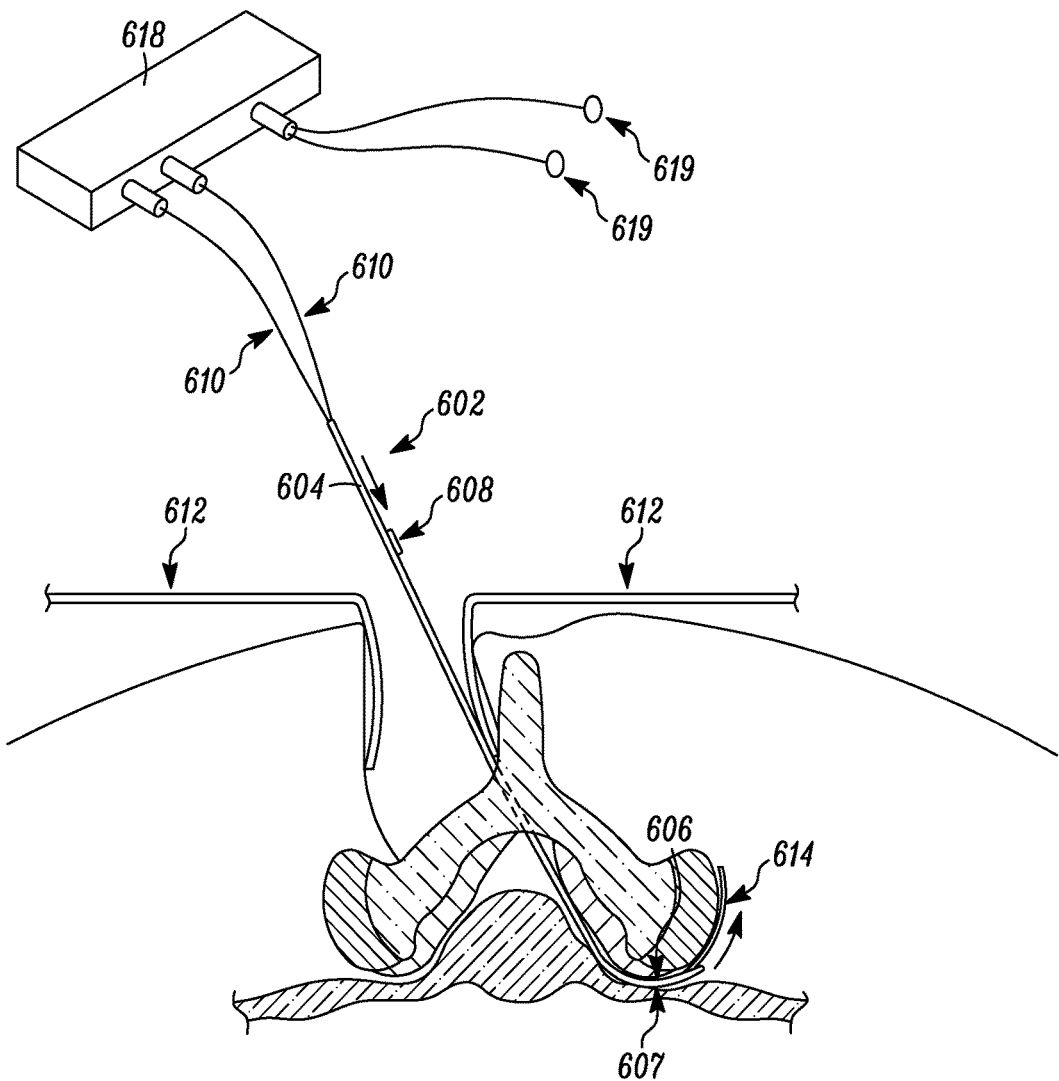
Figure 11C:
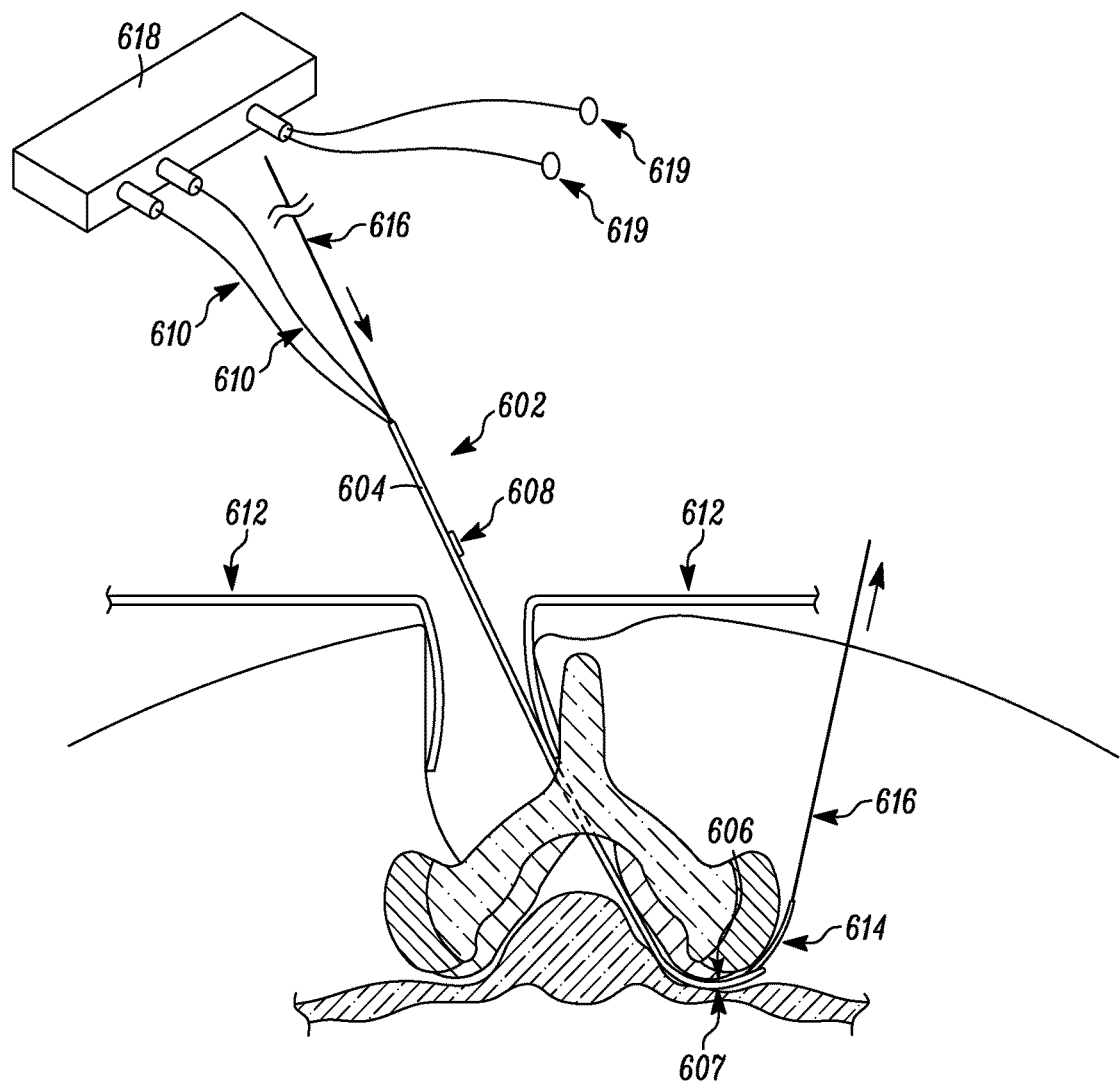

With reference now to FIGS. 11A-11E, an alternative embodiment of a spinal access method and device, similar to that described in FIGS. 10A-10F, is shown. (FIGS. 11A-11E are not drawn to scale.) In one embodiment, a probe 602 may be inserted into a patient's back via an open surgical approach using retractors 612, although less invasive ("partial open") or percutaneous access approaches may be employed in alternative embodiments. Probe 602 may include an elongate shaft 604 (or "body") having a longitudinal axis, a distal portion with a flat configuration having an upper surface 606 and an opposed lower surface 607, and an inner lumen. Probe 602 may also include a flexible, tubular guide member slidably disposed in the lumen of shaft 604 (lumen and guide member not shown in FIG. 11A) and a slide member 608 coupled with shaft 604 and the guide member. Optionally, some embodiments may also include one or more electrodes (or "signal transmitters") or energy modulated members coupled with upper surface 606 and/or lower surface 607. In FIGS. 11A-11C, the electrodes/signal transmitters are not visible, because they are embedded in upper surface 606 and lower surface 607.

Electrodes coupled with upper and lower surfaces 606, 607 may be coupled proximally with wires 610, which extend along the length of shaft 604 and then extend to a signal source 618 (or "power source"). In an alternative embodiment, probe 602 may include an internal power source, such as a battery housed in or coupled with shaft 604. Signal source 618 may, in some embodiments, be coupled with one or more electromyograhpy (EMG) electrodes 619. EMG electrodes 619 generally comprise electrodes capable of detecting an EMG response and are configured to be inserted into a muscle physiologically coupled to a nerve to be monitored or placed on skin above the muscle. Signal source 618 may be configured to receive sensed EMG signals from EMG electrodes 619 and process such signals to provide data to a user. In such systems, a display monitor may optionally be included, either as a separate unit or as part of signal source 618. Any suitable number of EMG electrodes 619 may be coupled with signal source 618, in various embodiments, and the two EMG electrodes 619 shown are for exemplary purposes only. For example, in some embodiments, such as when a lumbar spinal stenosis treatment is to be performed, EMG electrodes 619 may be placed bilaterally in a patient's tibialis anterior, vastus medialis, biceps femoris and medial gastroc muscles, or some combination thereof. In alternative embodiments, other nerve monitoring or sensing technologies may be used instead of or in addition to EMG, such as somatosensory evoked potentials (SSEPs), motor evoked potentials (MEPs), or the like. Additionally or alternatively, visible and/or palpable muscle twitch may be monitored in any embodiment.

As shown in FIG. 11A, probe 602 may be advanced along a natural tissue interface between neural tissue (cauda equina or spinal cord and nerve root, for example) and another tissue (or tissues) in the body, such as ligamentum flavum and/or vertebral bone, such as superior and inferior articular processes of a facet joint. In other words, probe 602 may be advanced along this tissue interface such that lower surface 607 is oriented toward the neural tissue and upper surface 606 is oriented away from the neural tissue. In some embodiments, the distal portion of shaft 604 may be advanced to position upper surface 606 and lower surface 607 partially or completely within an intervertebral foramen. In some embodiments, the tissue interface comprises two adjacent tissue planes, and advancing probe 602 may cause the distal end of probe 602 to dissect neural tissue from other tissue, such as target ligament and/or bone tissue, along the tissue interface. Generally, probe 602 may be advanced along a path approximating a path along which a tissue removal or modification device may be passed.

In some cases, the distal portion of shaft 604 may be positioned between neural and non-neural tissue without the surgeon being able to view the positioning. In other embodiments, it may be possible to visualize placement of shaft 604 using one or more visualization devices, such as externally applied fluoroscopy or a visualization device coupled with probe 602. In some embodiments, a surgeon or other physician placing probe 602 between two tissues will typically want to confirm that a desired positioning of probe 602 relative to the tissues has been achieved. For example, a surgeon may want to confirm that the distal portion of probe 602 has not been placed under the nerve root rather than between the nerve root and target tissue. In some embodiments, confirming a desired placement of probe 602 may involve delivering a first electrical current to a first electrode along lower surface 607, delivering a second electrical current to a second electrode along upper surface 606, and verifying that lower surface 607 of the advanced probe 602 remains oriented toward the neural tissue and upper surface 606 remains oriented away from the neural tissue by monitoring neural response (e.g., action potentials) to the first and second electrical currents. In an alternative method, the order of delivering current may be switched, so that the electrode on the upper surface 606 is activated before the electrode on the lower surface 607.

In some embodiments, electrical current may be applied to either electrode, and the current may be increased (if necessary) until a response in nearby nerve tissue is measurable, such as by EMG measurements, and/or observable, such as by viewing or feeling a muscle twitch. It has been found that even when an electrode on an upper surface 606 of probe 602 is located adjacent non-neural tissue, the electrode will eventually stimulate a nearby nerve if the current is increased to a sufficient level. It has also been found that an electrode located on a surface 606, 607 immediately adjacent or in direct contact with neural tissue requires significantly less current to stimulate a nerve response than the current required in the electrode farther from the nerve. Thus, in one embodiment, sufficient current may be applied to an electrode on upper surface 606 to stimulate neural tissue, sufficient current may be applied to an electrode on lower surface 607 to stimulate neural tissue, and the amounts of current required for each electrode ("threshold currents") may be compared, to determine which surface 606, 607 is closest to the nerve, nerve root, cauda equina and/or spinal cord. In this way, the location of neural tissue relative to probe 602 may be determined, thus facilitating safe placement and orientation of a guidewire, and subsequently a tissue modification device, between target and non-target tissues. This is just one example of a method for locating neural tissue. Further description of optional energy-delivery members and various neural localization methods are described further below, and as mentioned earlier, neural localization is an optional feature.

Referring to FIG. 11B, with the distal portion of probe 602 in place between target and non-target tissue, slide 608 may be advanced toward the distal end of probe 602 (solid-tipped arrow), to push a flexible, hollow, curved guide member 614 out of a distal opening in the lumen within probe 602 (hollow-tipped arrow). Curved guide member 614 may be housed within the lumen (not shown) in probe 602 during placement/positioning of probe 602 and may then be advanced, as shown in FIG. 11 B. In one embodiment, guide member 614 may be hollow and tubular, with one central lumen running longitudinally through it. In alternative embodiments, guide member 614 may have multiple lumens and/or have an alternative cross-sectional shape, such as but not limited to flat/hollow, ovoid, elliptical, rectangular, figure-8 or the like. In various embodiments, curved guide member 614 may be made of any of a number of different materials, may have a variety of different lengths, diameters and wall thicknesses, and may have any of a variety of different radii of curvature. For example, in various alternative embodiments, curved guide member 614 may be made of a metal, a polymer, such as nylon, polyester, Dacron®, polyethylene, acetal, Delrin® (DuPont, Wilmington, Del.), polycarbonate, nylon, polyetheretherketone (PEEK), and polyetherketoneketone (PEKK), or some combination of polymers or metals and polymers.

In various embodiments, curved guide member 614 may extend out of the distal opening on probe for any desired length, such as between about 1 mm and about 5 cm. In some embodiments, guide member 614 may have a first shape (such as predominantly straight) while residing within the lumen in probe 602 and may assume a second, curved shape upon exiting the distal opening. To allow for such a shape change, in some embodiments, guide member 614 may be fabricated, at least in part, of shape memory or super-elastic materials. In alternative embodiments, guide member 614 may assume a straight configuration upon exiting the distal opening in probe 602. For example, in one embodiment, the distal portion of probe 602 may be curved, and guide member 614 may exit the distal opening and proceed in approximately a straight line from the distal opening. In various curved embodiments, guide member 614 may have any suitable radius of curvature. In one embodiment (shown in FIG. 11 B), guide member 614 may be configured to curve around a surface of a facet joint between two vertebrae. In alternative embodiments, rather than (or in addition to) activating one or more electrodes on one or more surfaces of the distal portion of probe 602, such electrodes may be disposed on one or more surfaces of guide member 614. Examples of such embodiments are described further below.

As shown in FIG. 11C, after guide member 614 has been advanced at least partially out of the distal opening in probe 602, a guidewire 616 may be advanced into probe 602 (solid-tipped arrow) and through guide member 614 to pass through the patient's tissue and out the back (hollow-tipped arrow). In one embodiment, probe 602 includes an inner lumen that is continuous from a proximal opening, into which guidewire may be inserted, through to a distal opening, through which guide member 614 is advanced. Guidewire 616 thus may be advanced into the lumen of probe 602, into a proximal opening of a lumen of guide member 614, which resides in the probe lumen, and out of a distal opening of the lumen of guide member 614. Generally, guide member 614 helps direct guidewire 616 out of the patient's back in approximately a desired direction. In some embodiments, guide member 614 may be sufficiently rigid that passing guidewire 616 through guide member 614 will not significantly change the radius of curvature of guide member 614. In an alternative embodiment, guide member 614 may be more flexible, such that guidewire 616 may at least partially straighten guide member 614 when it passes through its lumen. In some embodiments, guide member 614 may be shaped to direct guidewire 616 out of the patient's back at a location apart from the entry point of probe 602 into the back (as shown in FIG. 11C), while in alternative embodiments, guide member 614 may have a smaller radius of curvature and/or may be less flexible, to direct guidewire 616 out of the patient's back at a location at or near the entry point of probe 602 into the back. Guidewire 616 may have a beveled or sharpened distal tip to facilitate its passage through tissue in the back, the skin or elsewhere.

Once guidewire 616 is in a desired location in the patient, probe 602 may be removed from the patient. In one embodiment, guide member 614 may be retracted back into shaft 604 before probe 602 is withdrawn from the patient, while in alternative embodiments, probe 602 may be withdrawn without retracting guide member 614.

Figure 11D:
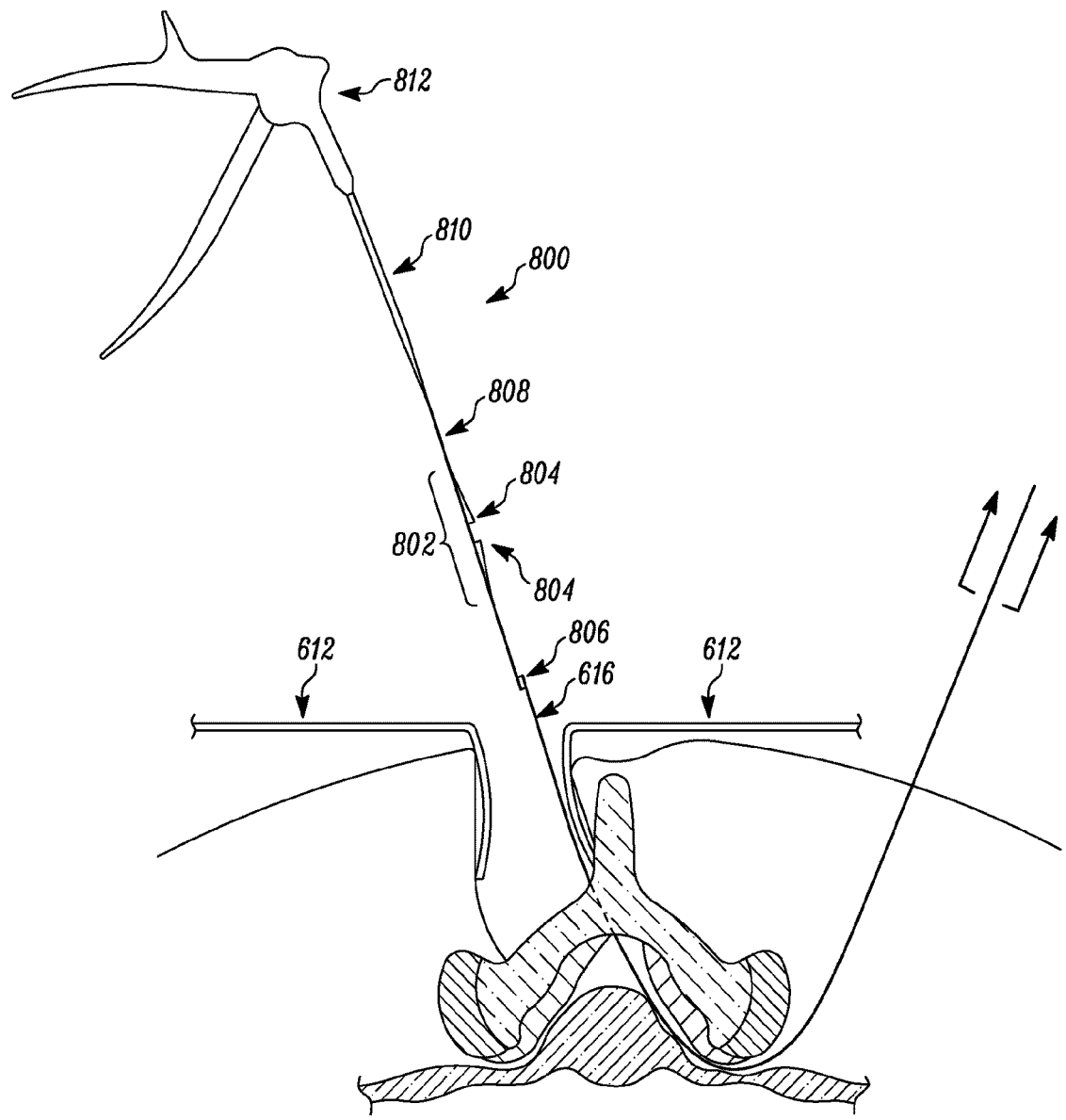

Referring now to FIG. 11D, once guidewire 616 is in a desired position and probe 602 is removed, one end of guidewire 616 may be coupled with a tissue modification device 800 at or near its distal end. In the embodiment shown, tissue modification device 800 includes a low-profile segment 808, which includes a tissue modifying portion 802 having two cutting blades 804, a guidewire connector 806 near the distal end of low-profile segment 808, a shaft 810 extending proximally from low-profile segment 808, and a proximal handle 812 coupled with shaft 810. In the embodiment shown, guidewire 616 may be pulled through the patient's back to pull tissue modification device 800 into the patient's back and to a desired position for performing a tissue modification procedure. In an alternative embodiment, tissue modification device 800 may be advanced over guidewire 616, such as over a guidewire lumen in tissue modification device 800, into the patient.

Figure 11E:
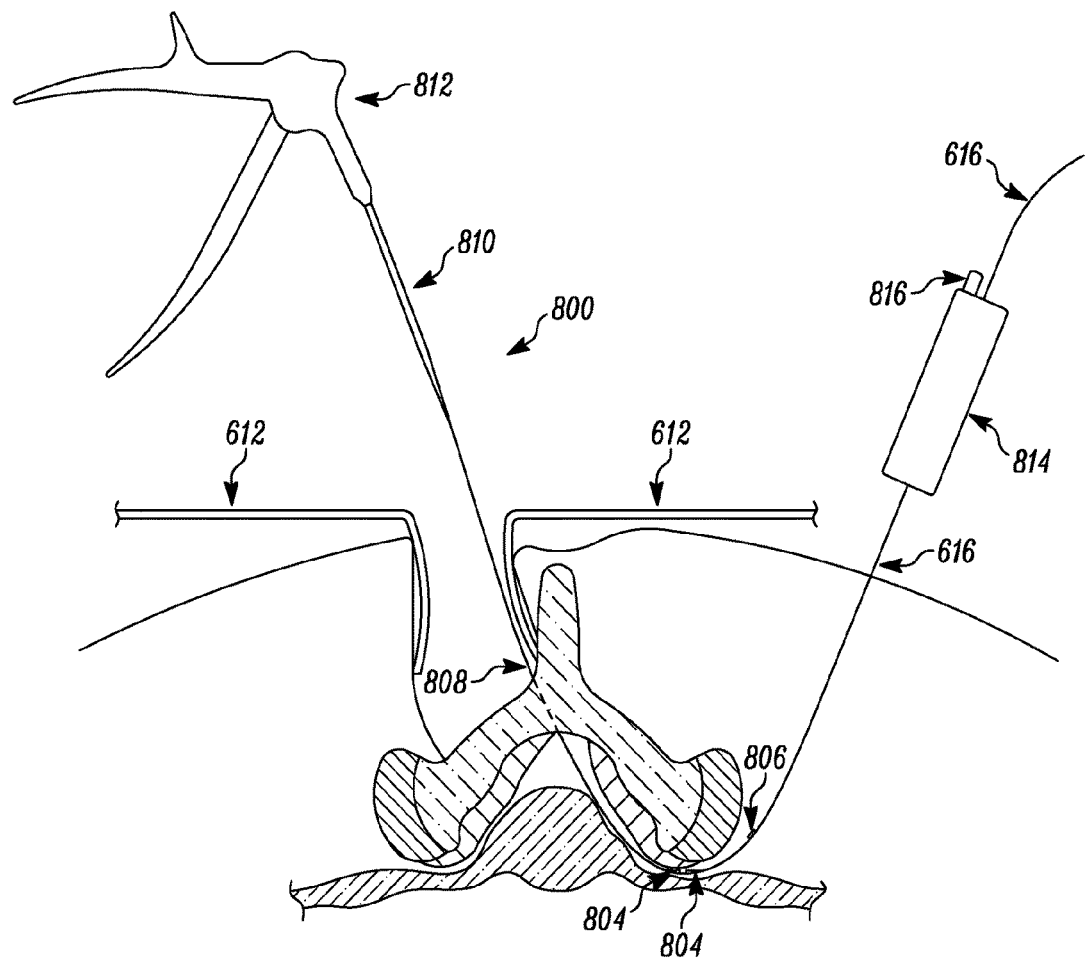

FIG. 11E shows tissue modification device 800 in position for performing a tissue modification procedure, with tissue modifying portion 802 located between target and non-target (i.e., nerve root) tissue and facing the target tissue. Additionally, a distal handle 814 has been removably coupled with guidewire 616. Handle 814 may include a lever 816 for clamping handle tightly to guidewire 616 to enable a user to apply tensioning and/or anchoring force to guidewire 616 and thus help urge tissue modifying portion 802 against target tissue. In various embodiments, any of a number of other tissue modification devices may be used, some of which have been described above.

Figure 12:
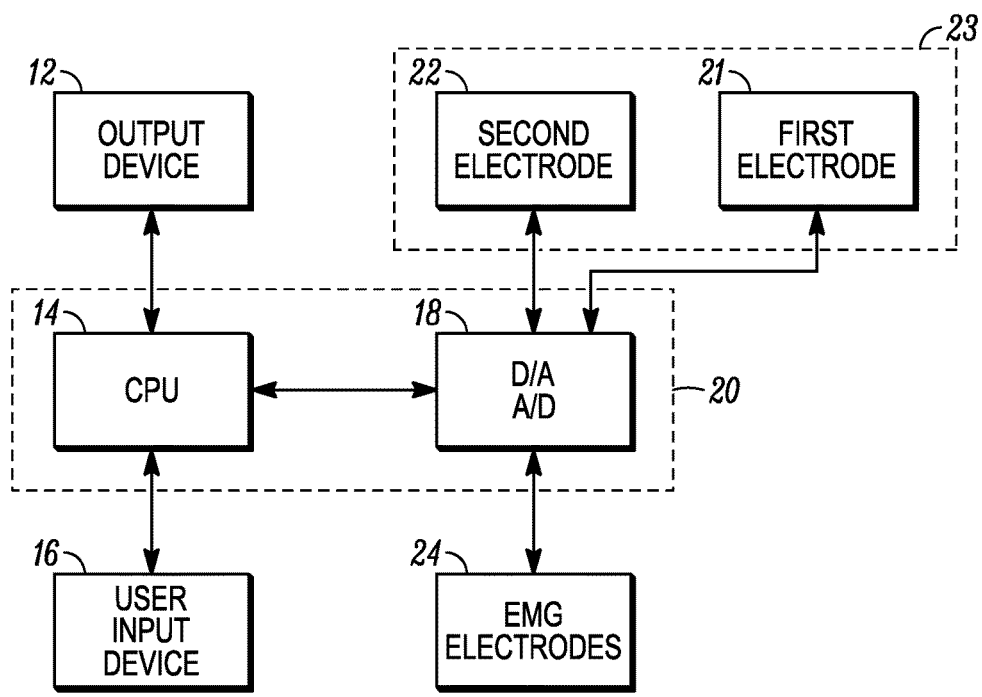
FIG. 12 is a diagram of a system for providing neural localization according to one embodiment of the present invention.

Referring now to FIG. 12, a diagrammatic representation of one embodiment of a neural localization system 10 is shown. Neural localization system 10 may include a probe 23, having a first electrode 21 and a second electrode 22 (or optionally any other number of electrodes in alternative embodiments), multiple EMG electrodes 24, an output device 12, an optional user input device 16, and a processor 20. Processor 20 may include a central processing unit ("CPU") 14 and a Digital to Analog converter (D/A) and Analog to Digital Converter (A/D) 18. CPU 14 may comprise any microprocessor having sufficient processing power to control the operation of D/A A/D converter 18 and output device 12. D/A A/D converter 18 may comprise such device having a sufficient operating cycle to generate signals as described herein and a sufficient sampling rate.

Generally, CPU 14 controls the operation of D/A A/D converter 18 and output device 12, in some embodiments based on data received from a user via user input device 16, and in other embodiments without input from the user. User input device 16 may include any input device or combination of devices, such as but not limited to a keyboard, mouse and/or touch sensitive screen. Output device 12 may include any output device or combination of devices controllable by CPU 14, such as but not limited to a computer monitor, printer and/or other computer controlled display device. System 10 generates electrical signals, which are transmitted to electrodes 21 and 22, and receives signals from EMG electrodes 24. Generally, CPU 14 may generate a digital representation of signals to be transmitted by electrodes 21 and 22, and D/A A/D converter 18 may convert the digital signals to analog signals before they are transmitted to electrodes 21 and 22. EMG electrodes 24 receive EMG or evoked muscle action potential ("EMAP") signals generated by muscle electrically coupled to EMG electrodes 24 and to a depolarized nerve (motor unit). One or more nerves may be depolarized by one or more electrical signals transmitted by electrodes 21 and/or 22. D/A A/D converter 18 converts an analog signal received by EMG electrodes 24 into a digital signal that may be processed by CPU 14. CPU 14 may hold any suitable software for processing signals from EMG electrodes 24, to electrodes 21, 22 and the like. According to various embodiments, output device 12 may display any of a number of different outputs to a user, such as but not limited to information describing the signals transmitted to electrodes 21 and 22, information describing signals sensed by EMG electrodes 24, a visual and/or auditory warning when a nerve has been stimulated, and/or the like. In various alternative embodiments, system 10 may include additional components or a different combination or configuration of components, without departing from the scope of the present invention.

Figure 13A:
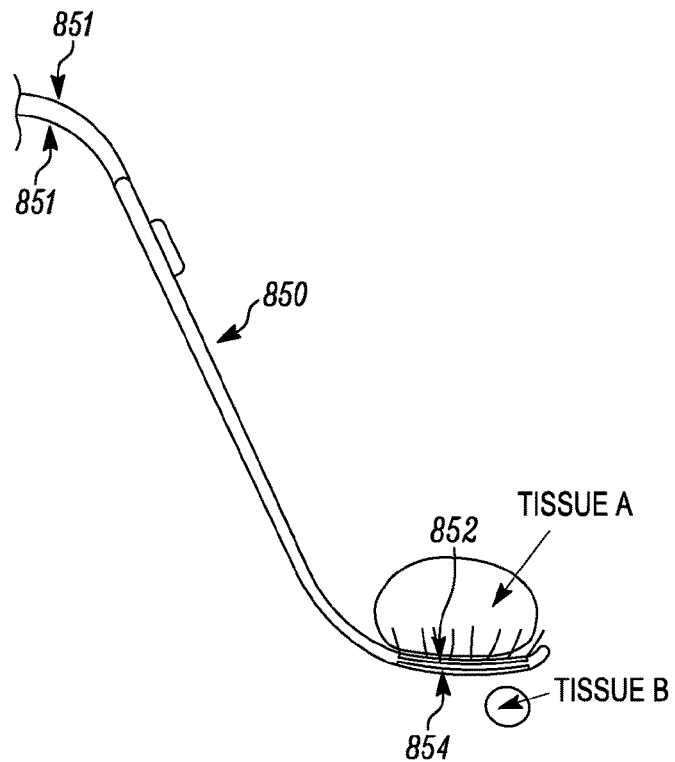
FIGS. 13A and 13B are diagrammatic side views demonstrating a method for applying energy to electrodes on two surfaces of a probe according to one embodiment of the present invention.
Figure 13B:
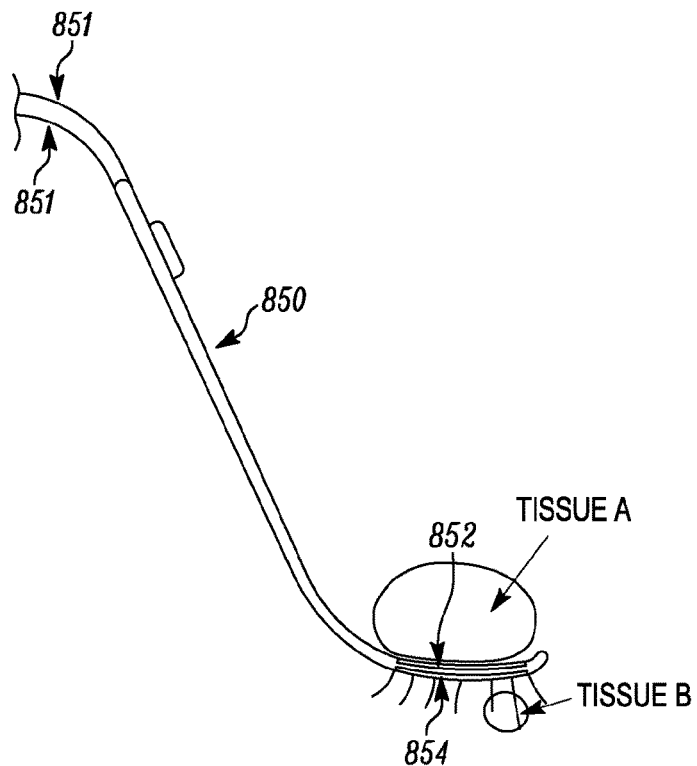

FIGS. 13A and 13B demonstrate, in diagrammatic form, one embodiment of a method for neural localization, similar to the methods described above. In these figures, a probe 850 is shown having an upper surface electrode 852 and a lower surface electrode 854, each of which is coupled with a wire 851 that extends to a signal source (not shown). A distal portion of probe 850 is disposed between two tissues, Tissue A and Tissue B. For example, Tissue A may comprise a combination of vertebral bone and ligamentum flavum tissue, and Tissue B may comprise a nerve root exiting a spine. It may be the case, during a tissue modification procedure in a spine (or in other areas of the body) that a surgeon or other practitioner places a probe between two tissues without knowing for sure what the two tissues are or which might be a target tissue and which might be nerve tissue the surgeon does not want to adversely affect or damage during the procedure. In one embodiment, using probe 850, current may be supplied to upper electrode 852, as in FIG. 13A. If the initial amount of current supplied does not result in measurable or observable action potentials in the nerve, as seen for example in EMG measurement, an observed or felt muscle twitch, and/or other indicia of response, it may be surmised that upper electrode 852 is not in contact with or immediately adjacent nerve tissue. In one embodiment, the amount of current delivered to upper electrode 852 may be adjusted until a threshold (or minimal) amount of current required to stimulate measurable action potentials in the nerve is determined. It has been found that on some probes 850 an electrode not immediately in contact with or adjacent a nerve may still stimulate the nerve if enough current is delivered.

Referring to FIG. 13B, current may also be delivered to lower electrode 854, which in this case happens to be in contact with Tissue B, a nerve root. The threshold amount of current required to stimulate measurable action potentials via lower electrode 854 will most likely be significantly less than the amount required to stimulate measurable action potentials via upper electrode 852. Of course, the difference between the threshold current amounts may differ depending on the thickness, width or material of the distal portion of the probe, the shape or location of electrodes 852, 852 relative to probe 850, various characteristics of the tissues themselves, and/or the like. As an example, however, a threshold amount of current required from an electrode farthest from neural tissue on a probe may be greater than about 2 milliamps, while a threshold amount of current required from an electrode closest to neural tissue on the same probe may be less than about 1 milliamp. In another example, a threshold amount of current required from an electrode farthest from neural tissue on a probe may be greater than about 1 milliamp, while a threshold amount of current required from an electrode closest to neural tissue on the same probe may be less than about 0.1 milliamp. Thus, in some embodiments, it may take at least about two times more current, and more preferably at least about ten times more current, provided to an electrode on a probe surface facing opposite neural tissue than on a probe surface directly facing neural tissue to stimulate measurable action potentials. Therefore, in one embodiment, the amounts of current required to stimulate a nerve response via two different electrodes on a probe may be compared to help determine the location of nerve tissue. In some embodiments, a ratio between the two amounts of required current may be calculated.

Figure 14A:
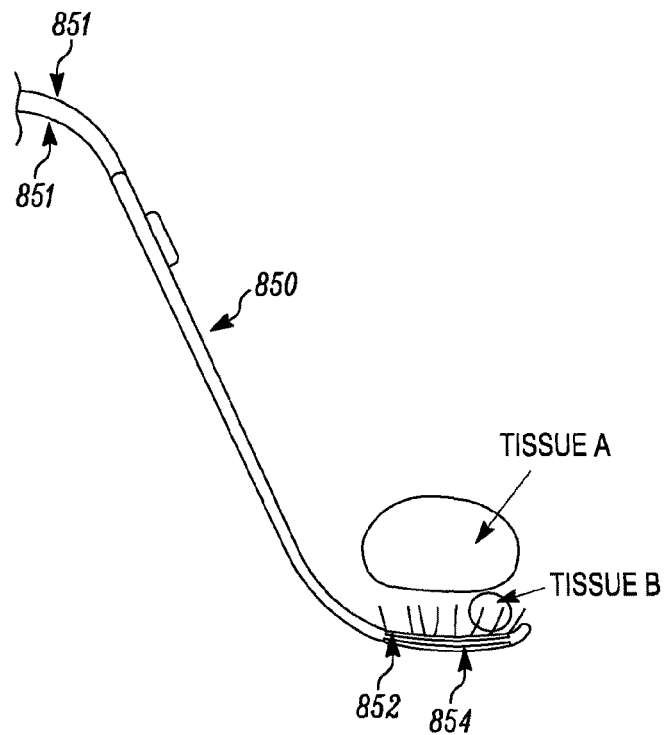
FIGS. 14A and 14B are diagrammatic side views demonstrating a method for applying energy to electrodes on two surfaces of a probe according to the embodiment shown in FIGS. 13A and 13B but with a different location relative to body tissue.
Figure 14B:
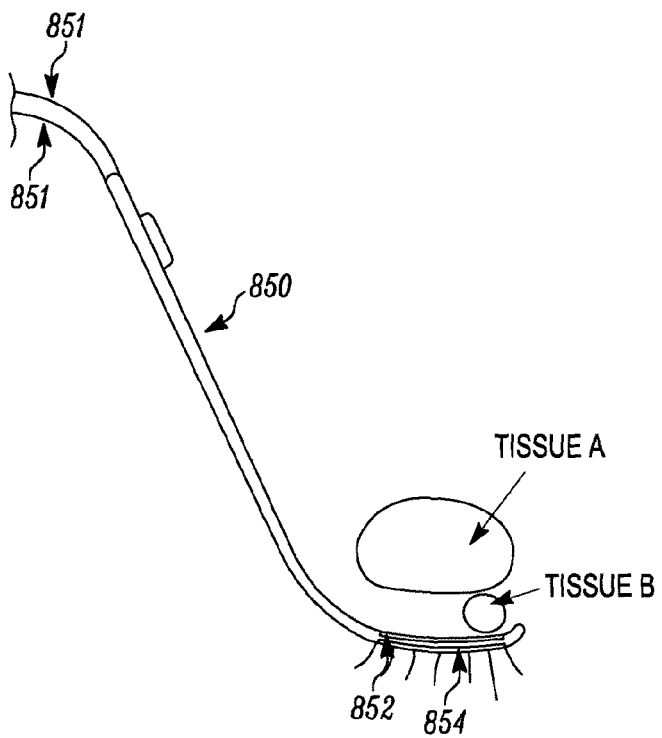

Referring now to FIGS. 14A and 14B, in another exemplary procedure, probe 850 may be inserted so that Tissue A (bone/ligament) and Tissue B (nerve root) are on the same side of the distal portion of probe. In this example, as demonstrated in FIG. 14A, when upper electrode 852 is activated, the nerve root (Tissue B) will be stimulated with a relatively low amount of current. This might quickly tell a surgeon that probe 850 is positioned under the nerve root. The surgeon may then further confirm the location of probe 850 relative to Tissues A and B by activating lower electrode 854, as in FIG. 14B. It would likely take significantly more current to stimulate the nerve root via lower electrode 854 than it did via upper electrode 852, thus confirming probe's 850 location under the nerve root. In some instances, where the surgeon is trying to position probe 850 above nerve root tissue, he/she may then remove and reposition probe 850 to achieve a desired positioning.

In various alternative embodiments, any of a number of alternative methods for positioning a probe and localizing neural tissue may be used. For example, some embodiments may involve using only one electrode on one surface of a probe, while others may involve using more than two electrodes. Any combination of electrodes and comparisons of current required to stimulate a measurable action potential or other indication of nerve response may be used, without departing from the scope of the present invention. As another example, the order in which current is delivered to various electrodes may be altered in different embodiments.

Furthermore, and with reference now to FIGS. 15A-15D, in various embodiments, any of a number of nerve stimulation and/or tissue distinguishing techniques and devices may be employed, either alone or in combination. The examples described above have generally been directed to the use of electrodes, such as radiofrequency (RF) electrodes. In alternative embodiments, however, it may be possible to examine tissue densities using ultrasound, piezoelectric devices, optical coherence tomography (OCT), or the like. By examining tissue density, it may be possible to distinguish tissues that a surgeon wishes to avoid, such as nerve and blood vessel, from target tissues, such as ligament and bone.

Figure 15A:
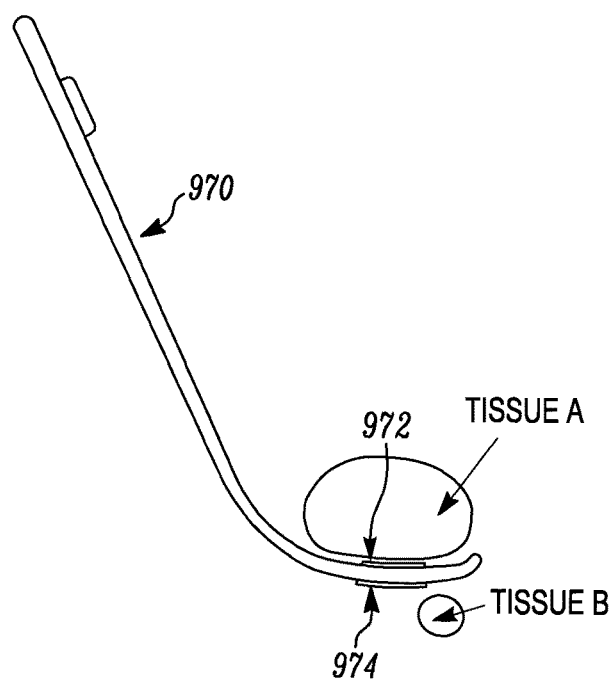
FIGS. 15A and 15C are diagrammatic side views demonstrating a method for applying energy to electrodes on two surfaces of a probe according to an alternative embodiment of the present invention.
Figure 15B:
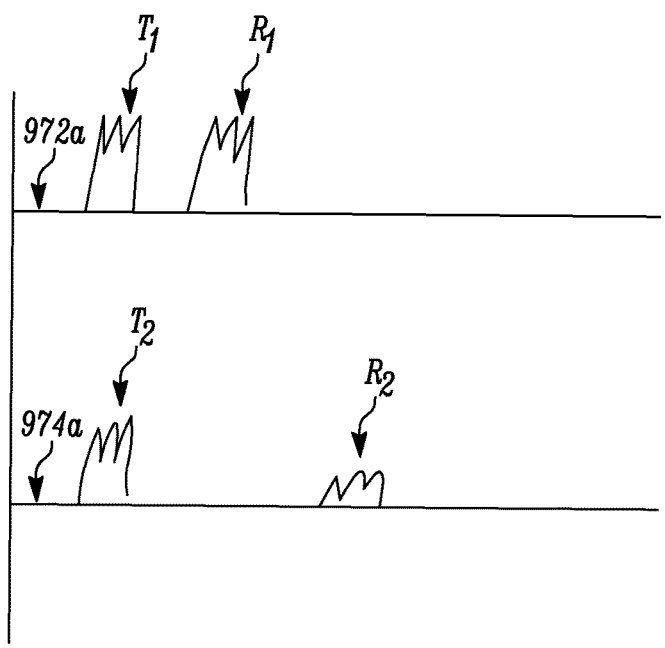
FIGS. 15B and 15D are diagrammatic representations of transmitted and reflected signals from and ultrasound transducers of the probes of FIGS. 15A and 15C.

In one embodiment, for example, a probe 970 may include an upper ultrasound transducer 972 on an upper surface of its distal portion and a lower ultrasound transducer 974 on a lower surface of its distal portion. Ultrasound energy may be delivered from transducers 972, 974 and time of flight and/or amplitude of reflected signals may be measured. If probe 970 is positioned between bone/ligament (Tissue A) and neural tissue (Tissue B), for example, its position may be confirmed by applying ultrasound energy separately from upper transducer 972 and lower transducer 974. Harder tissues, like bone, will reflect ultrasound energy faster (shorter time of flight) and with higher amplitude than softer tissues, like nerve. For example, FIG. 15B diagrammatically shows exemplary signal measurements 972a, 974a from upper transducer 972 and lower transducer 974, respectively. When probe 970 is positioned as in FIG. 15A and upper transducer 972 is activated (such as in pulse mode), signal measurement 972a may show a transmitted signal T1 and a reflected signal R1. The reflected signal R1 may return quickly from the nearby, relatively hard bone/ligament tissue, and may have an amplitude almost the same as the transmitted signal T1. When lower transducer 974 is activated, it reflects off of neural tissue and thus, signal measurement 974a shows the transmitted signal T2 and then a reflected signal R2 with a longer time of flight and smaller amplitude than the received signal R1.

Figure 15C:
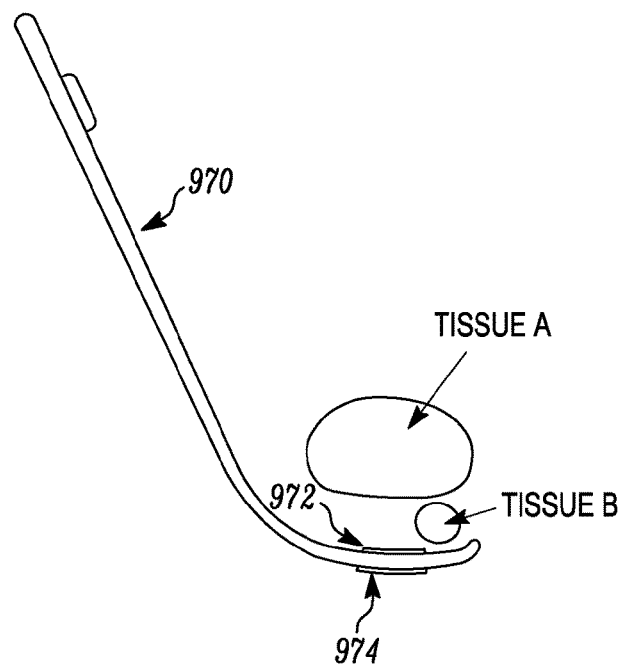
Figure 15D:
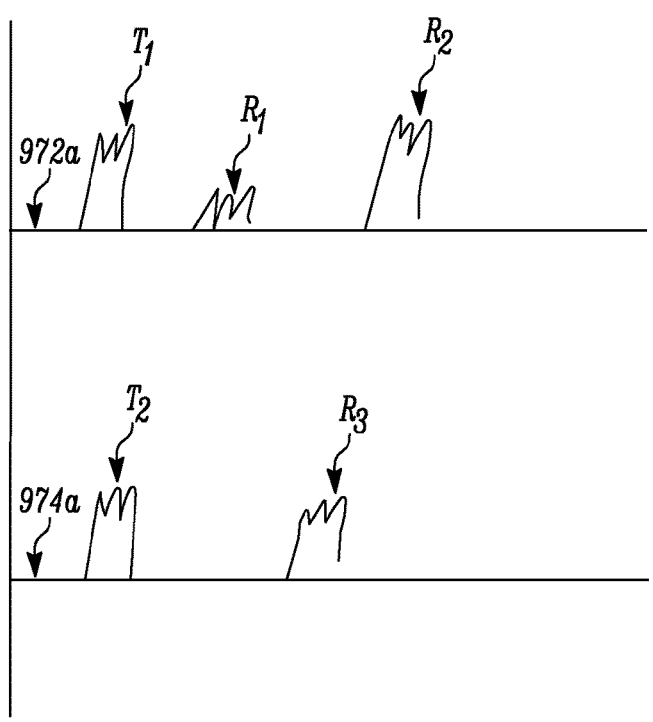

If probe 970 is placed under the bone/ligament and nerve root, as in FIG. 15C, it would be expected that ultrasound signals would look differently, as shown in the signal measurements 972a, 974a of FIG. 15D. When upper transducer 972 is activated, creating a first transmitted signal T1, a first reflected signal R1 with a smaller amplitude will come back first from the nearby nerve tissue, and then a second reflected signal R3 with a larger amplitude will come back from the bone/ligament tissue sometime later. When lower transducer 974 is activated, creating a second transmitted signal T2, a third reflected signal R3 will come back at some point from adjacent tissue and look different than first or second reflected signals R1 and R2. Using these or other combinations of ultrasound transducers and signals may help a surgeon or other user of probe 970 confirm that a desired probe positioning has been achieved. Various embodiments of a probe may thus include any suitable combination of ultrasound transducers and/or other devices such as electrodes, OCT devices or the like.

Figure 16A:
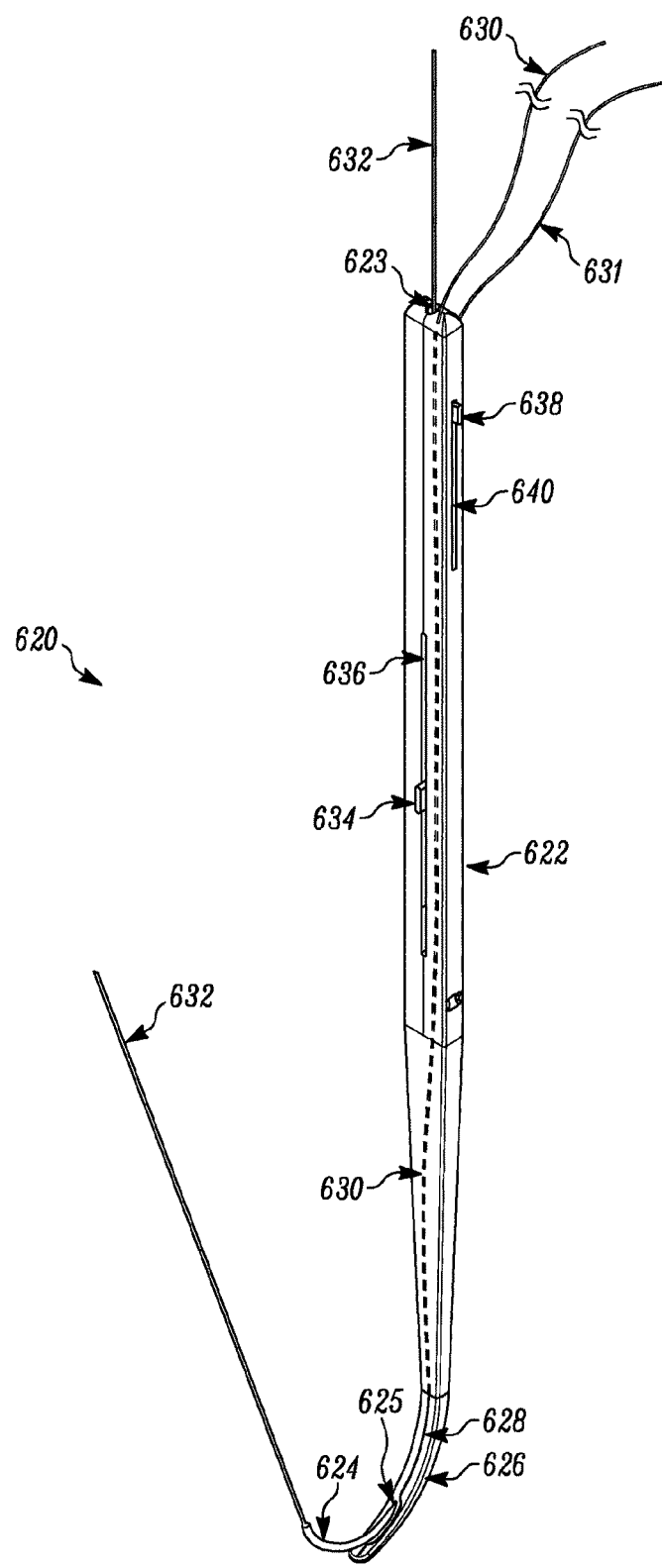
FIGS. 16A-16C are perspective, frontal and side/cross-sectional views, respectively, of a probe device for facilitating guidewire placement in a spine according to one embodiment of the present invention.
Figure 16B:
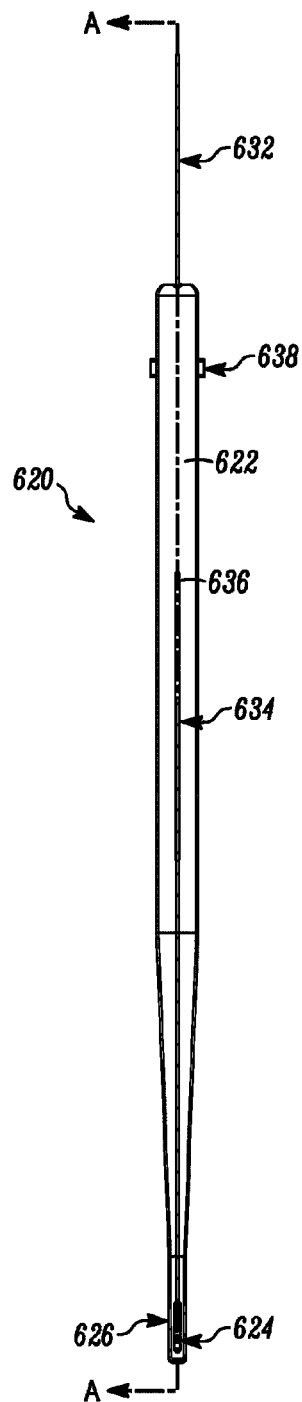
Figure 16C:
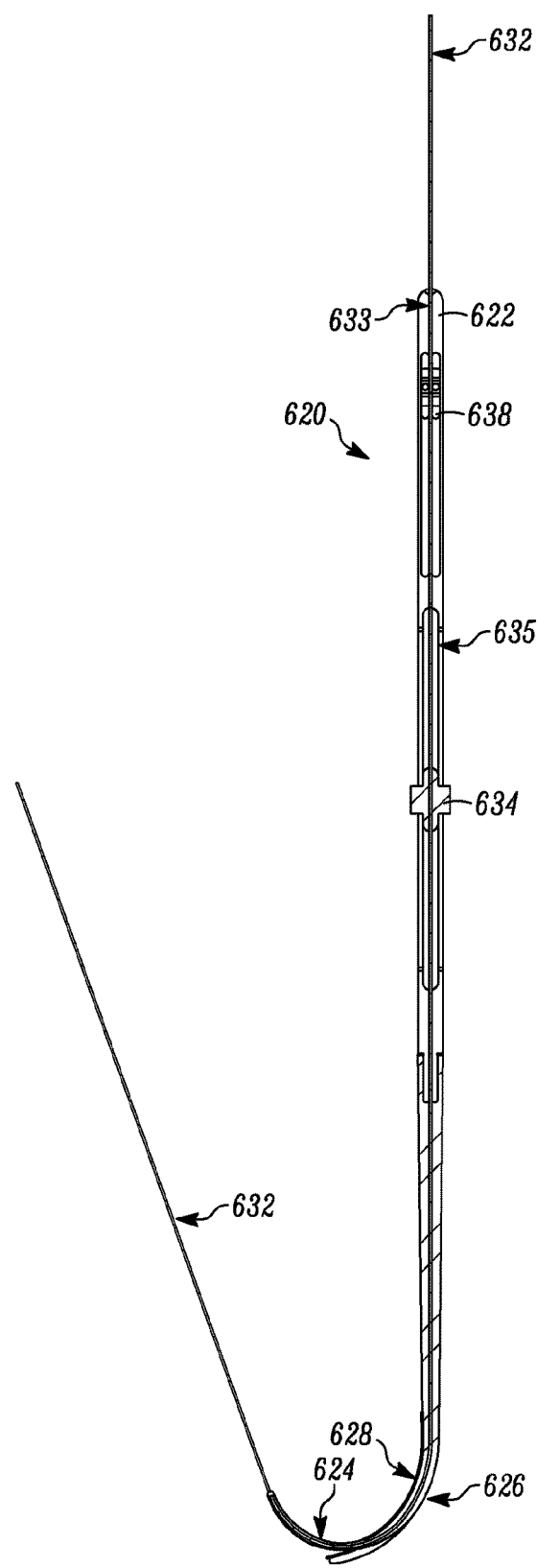

Referring now to FIGS. 16A-16C, one embodiment of a probe device 620 for facilitating passage of a guidewire 632 to a desired location in a patient is shown in greater detail. In the embodiment shown, probe 620 includes a shaft portion 622 having a proximal opening 623, a distal curved portion 626 having a distal opening 625, a tubular, curved guide member 624, a guide member slide 634 disposed in a channel 636, a guidewire slide 638 disposed in another channel 640, an upper surface electrode 628 coupled with distal portion 626, and a first wire 630 coupled with upper surface electrode 628 and disposed along the length of probe 620 to extend to a power source (not shown). This embodiment may further include a lower surface electrode (not visible) coupled with a second wire 631. Alternative embodiments may include only one electrode or more than two electrodes.

Distal portion 626 generally has a configuration with at least two major sides or surfaces, such as an upper surface and a lower surface. Electrode 628 (or multiple electrodes in some embodiments) may be disposed on upper and lower surfaces, as described previously, to test tissue above and below distal portion 626. In some embodiments, electrode 628 or an array of electrodes may be disposed along a length of a longitudinal axis of distal portion 626. This axial length may approximate a length of tissue to be treated by a subsequently placed device, and thus the axial length of electrode 628 may help verify that the length of tissue to be treated does not include neural tissue. Thus, electrode 628 may be described as being disposed along an "axial verification length" of distal portion 626. As explained previously, in some embodiments, guide member 624 may be housed predominantly or entirely within a guide member lumen 635 (shown in FIG. 16C) in probe 620 to facilitate delivery of probe 620 into a patient, and guide member 624 may then be advanced, using slide 634, to wholly or partially extend out of distal opening 625. Slide 634 is coupled with guide member 624 and may be used to advance and retract guide member 624 into the probe's lumen 635. Guidewire 632 may be advanced into proximal opening 623, through a guidewire lumen 633 (shown in FIG. 16C) in shaft 622, and then into and through guide member 624. In one embodiment, as shown, optional guidewire slide 638 may be included to help advance guidewire 632. Other embodiments may not include guidewire slide 638.

FIG. 16B is a front view of probe 620, and FIG. 16C is a side, cross-sectional view of probe 620, along line A-A of FIG. 16B. FIG. 16C shows guide member lumen 635 and guidewire lumen 633 of probe 620, neither of which is visible in FIGS. 16A and 16B. As seen in FIG. 16C, guidewire lumen 633 and the inner lumen of guide member 624 create one continuous lumen through which guidewire 632 may pass.

As shown in FIG. 16A, in one embodiment, electrode 628 has a long, thin configuration and extends along a length of distal curved portion 626 and around one side of distal opening 625. In various embodiments, distal portion 626 may also include one or more similar (or differently configured) electrodes on a bottom surface, side surface and/or any other surface.

With reference now to FIGS. 17A-17E, any given electrode on a probe may have any of a number of different configurations. For example, as shown in FIG. 17A, in one embodiment, an electrode 860 may stop before distal opening 625. In another embodiment, as in FIG. 17B, an electrode 870 may extend along the probe, around distal opening 625, and back up another side of the same surface of the probe. In another embodiment, as in FIG. 17C, multiple spot electrodes 880 may be used, and they may be activated all at once or separately, in various embodiments. As in FIG. 17D, in another embodiment, a circular electrode 890 may surround distal opening 625 and be connected to the shaft of the probe via a wire 892. In yet another embodiment, as in FIG. 17E, a first electrode 900 may be coupled with an upper surface of the probe, while a second electrode 902 may be coupled with a side surface. FIGS. 17A-17E are provided for exemplary purposes. Any of a number of other suitable electrode configurations and combinations may be included in alternative embodiments.

In a number of the examples described above, one or more electrodes, ultrasound transducers and/or the like are disposed on upper and/or lower surfaces of a distal portion of a shaft of a probe, and a curved guide member may be extended out of a distal opening on the probe shaft. In various alternative embodiments, and with reference now to FIGS. 18A and 18B, one or more electrodes may be located on a curved guide member extending from a probe shaft (or needle) instead of or in addition to locating one or more electrodes on the probe shaft. In yet another alternative embodiment, one or more electrodes may alternatively or additionally be placed on a guidewire, such as a flat guidewire.

Figure 18A:
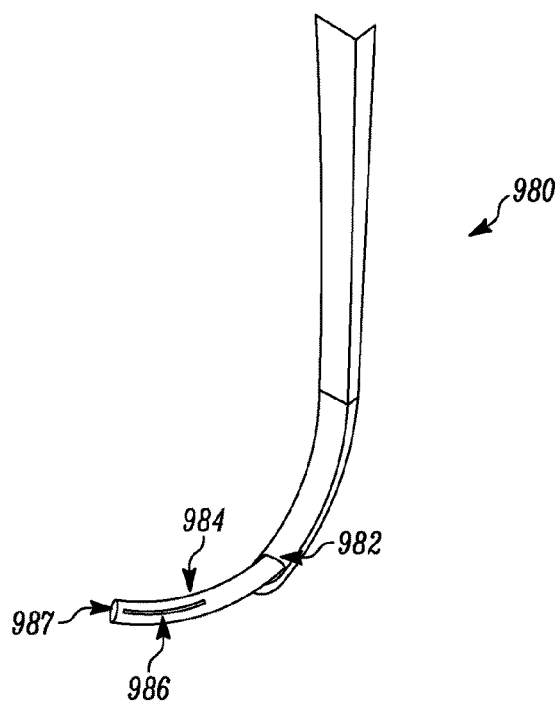
FIGS. 18A and 18B are perspective views of a probe and a needle, respectively, each with a guide member extension with electrodes according to one embodiment of the present invention.

In one embodiment, shown in FIG. 18A, a distal portion of a probe shaft 980 includes a distal opening 982, and a flat guide member 984 extends out of distal opening 982. Flat guide member 984 may include an upper surface electrode 986, a lower surface electrode (not visible), and a distal opening 987, through which a guidewire may pass. In this embodiment, guide member 984 has a flat (or flattened oval) cross-sectional shape so that it has upper and lower surfaces. This allows a user to separately activate upper electrode 986 and the lower surface electrode to help confirm a location of guide member 984 relative to neural tissue and/or other tissue in a body. Guide member 984 may have other shapes in alternative embodiments, but will typically have a shape having at least two sides, to facilitate determination of the orientation of guide member 984 relative to tissue.

Figure 18B:
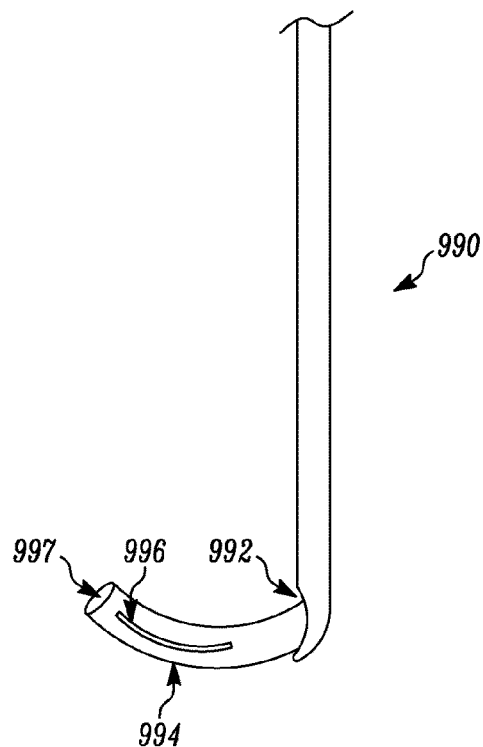

In an alternative embodiment, shown in FIG. 18B, a needle 990, such as an epidural needle, may be used to access an epidural space of the spine. Needle 990 may include a distal opening 992, and a guide member 994 may extend from opening 992. Guide member 994 may include an upper surface electrode 996, a lower surface electrode (not visible) and a distal opening 997. In some embodiments, guide member 994 may expand or unfold upon exiting distal opening 992 of needle 990 to assume a flat configuration. Again, guide member 994 may have any of a number of configurations, cross-sectional shapes and the like, but will often have a shape with at least two sides, for helping confirm an orientation of guide member 994 relative to tissue.

Figure 19A:
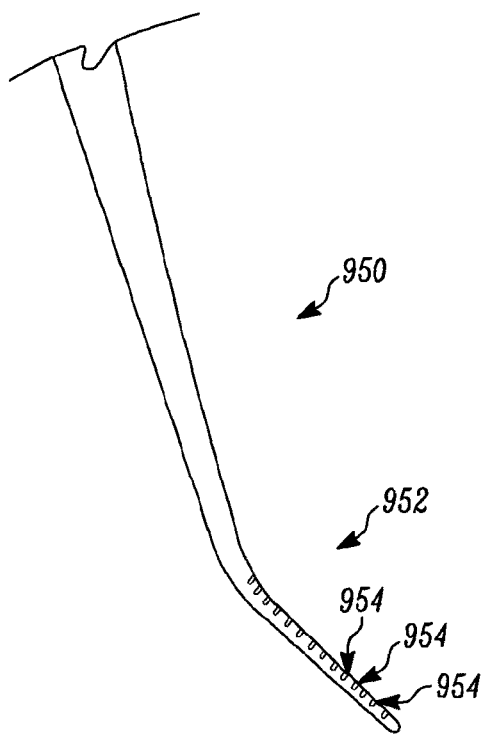
FIGS. 19A-19C are side views of a distal portion of an articulating probe device according to one embodiment of the present invention.
Figure 19B:
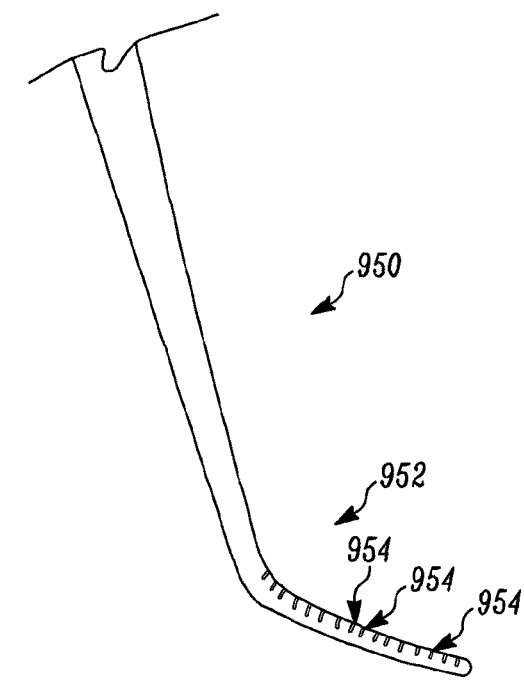
Figure 19C:
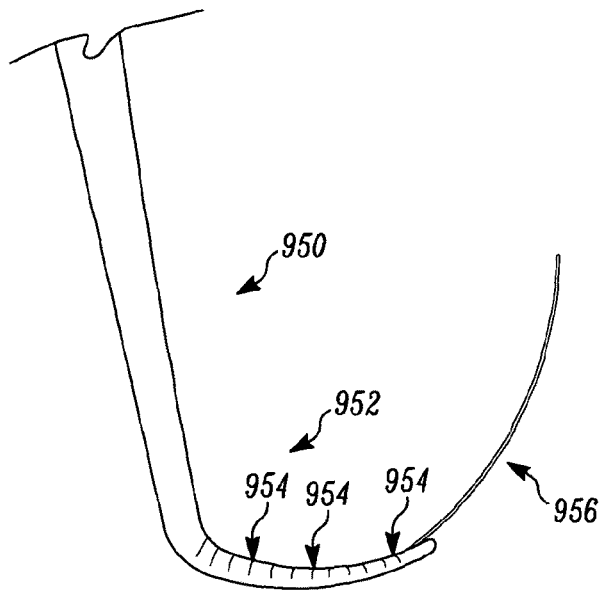

In further alternative embodiments, and with reference now to FIGS. 19A-19C, it may sometimes be advantageous to have a steerable or shape changing probe 950. For example, probe 950 (only a distal portion of which is shown) may include an articulating distal portion 952. Distal portion 952 may articulate, for example, from a straighter configuration, as in FIG. 19A, to a more bent configuration, as in FIG. 19B, and then to a curved/bent configuration, as in FIG. 19C. Any of a number of different mechanisms, actuators and the like may be used to articulate such a distal portion 952 in various embodiments. For example, in the embodiment shown, multiple slits 954 may be disposed along one side of distal portion 952, and one or more pull wires (not visible) may be coupled with distal portion 952 and extend to a more proximal portion of probe 950 to enable a user to pull the wires to bend/curve distal portion 952. In another embodiment, push rods might be used to straighten distal portion 952. A number of different technologies are known for articulating various tools, and any such suitable technology may be applied in various embodiment of probe 950. In some embodiments where such an articulating distal end 952 is included, probe 950 may not include a curved guide member, and instead, a guidewire 956 may be advanced directly out of a distal opening on probe 950, as shown in FIG. 19C. Articulating distal end 952 may facilitate advancement of probe 950 into narrow passages and/or use of a percutaneous or less invasive approach to a given target tissue.

Figure 20A:
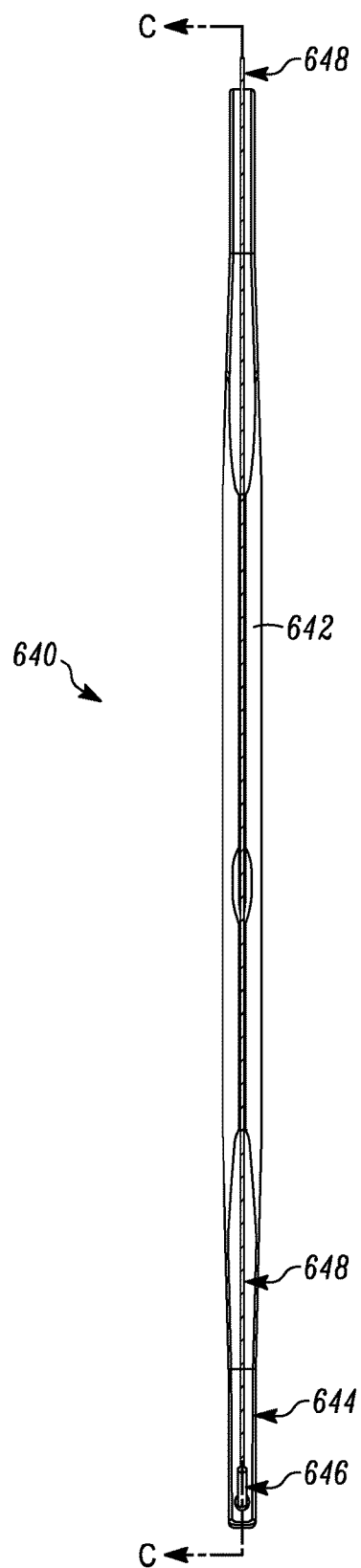
FIGS. 20A and 20B are frontal and side/cross-sectional views, respectively, of a probe device for facilitation guidewire placement in a spine according to an alternative embodiment of the present invention.
Figure 20B:
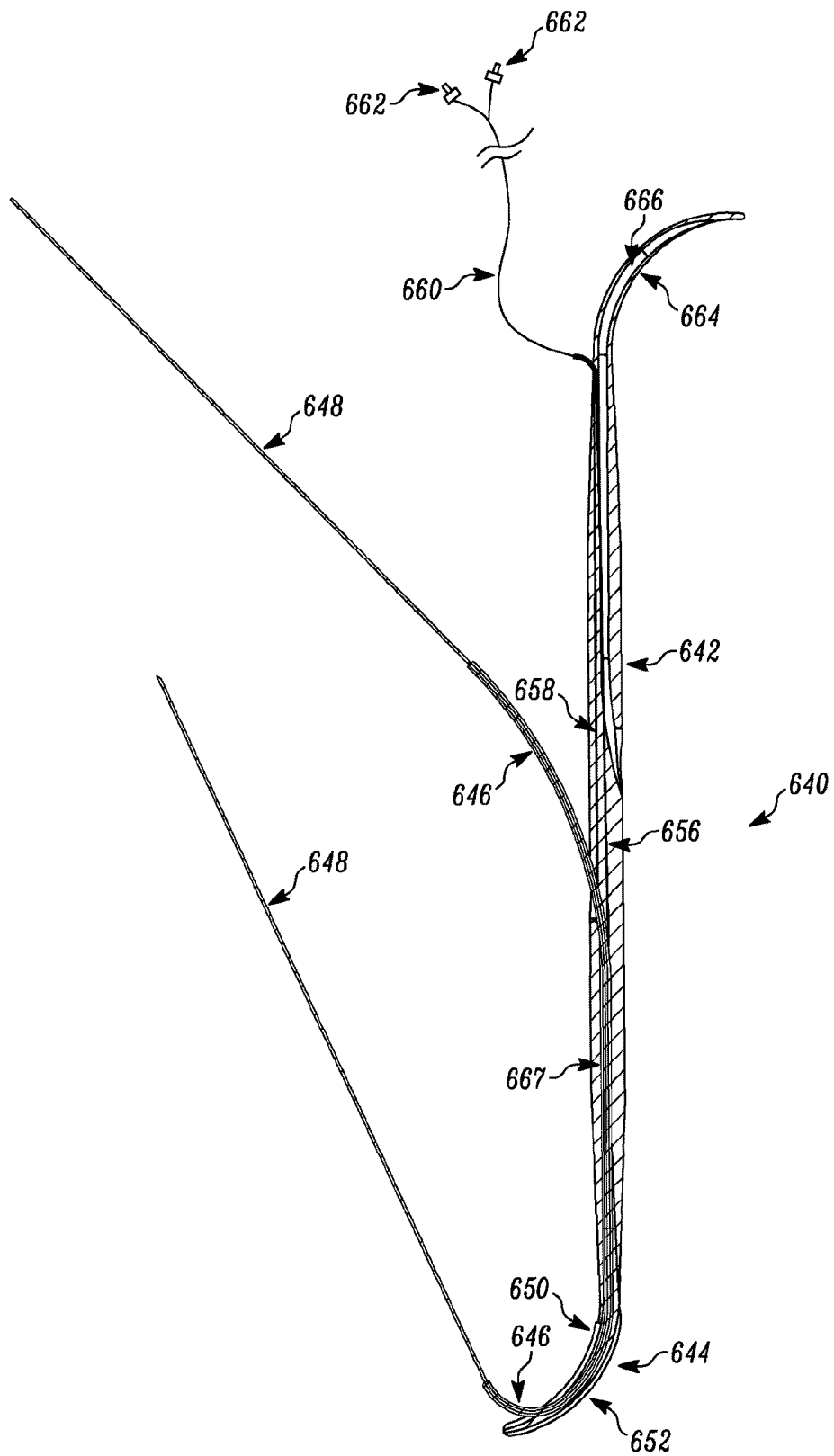

FIGS. 20A and 20B illustrate another alternative embodiment of a probe device 640, in front and side cross-sectional views, respectively. In this embodiment, probe 640 may include a shaft portion 642, two curved ends 664, 644 extending from opposite ends of shaft 642, two tubular channels 666, 667, a guide member 646, electrodes 650, 652 coupled with one end 644, wires 656, 658 coupled with electrodes 650, 652, and a common extension 660 of wires 656, 658, which splits to two separate power connectors 662. In this embodiment, it may be possible to use one end 644 for accessing one part of a spine, for example, and to use the opposite end 664 for accessing another part of the spine or the same part from a different approach or angle. For example, it may sometimes be desirable to pass probe 640 through an opening between two vertebrae, into the epidural space, and between an ipsilateral intervertebral foramen. During the same procedure, or in an alternative procedure, it may be desirable to pass probe 640 into the contralateral intervertebral foramen. Thus, ends 644, 664 may have different shapes, lengths, radii of curvature or the like, to facilitate access to different spaces and/or different approaches to the same space. In some embodiments, both ends 644, 664 may have guide members 646 and/or electrodes 650, 652, while in other embodiments, only one end 644 may include these features. In some embodiments, it may be possible to remove guide member from one channel 667 and advance it into the other channel 666. Although no slide device is shown in this embodiment, a slide may optionally be added, or guide member 646 may be advanced and/or retracted manually.

Figure 20C:
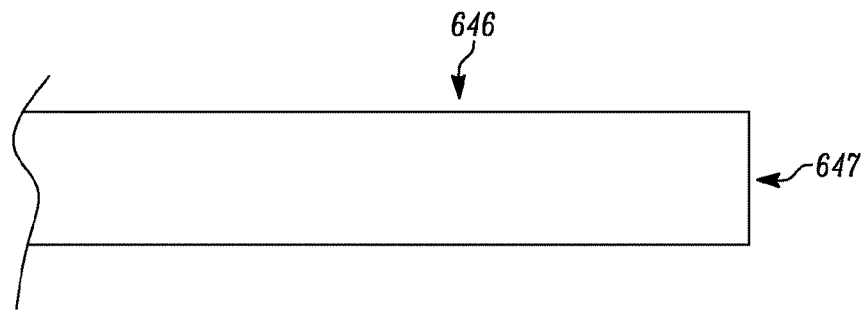
FIG. 20C is a side view of a portion of a guide member of the probe device of FIGS. 20A and 20B.
Figure 21A:
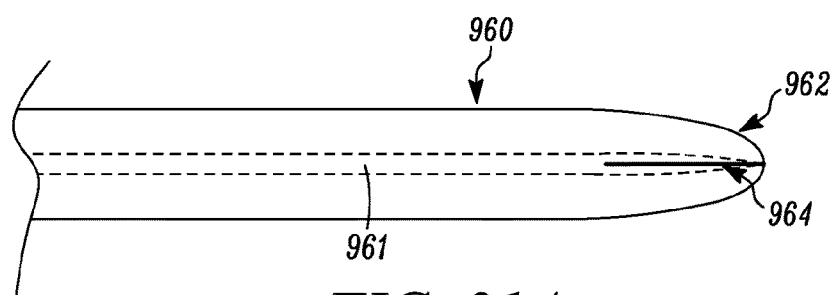
FIGS. 21A and 21B are side views of a guide member of a probe device according to an alternative embodiment of the present invention.
Figure 21B:
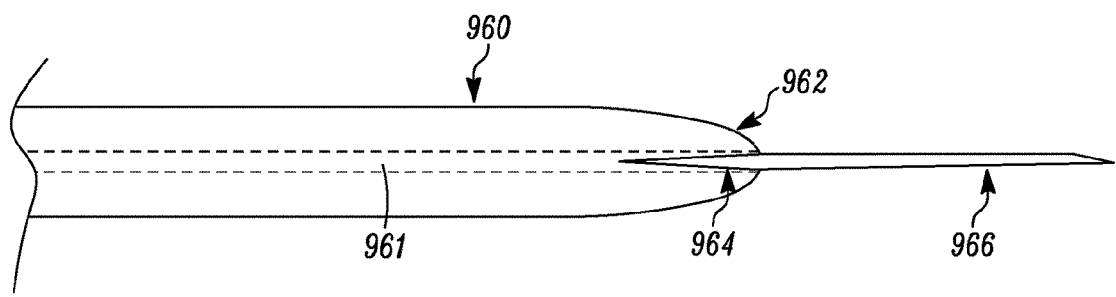

Referring now to FIG. 20C, guide member 646 from the embodiment in FIGS. 20A and 20B may have a cylindrical shape with a blunt distal end 647. In an alternative embodiment, as in FIGS. 21A and 21B, a guide member 960 may have a tapered distal end 962 with a longitudinal slit 964 that opens into a guidewire lumen 961 (dotted lines). When a guidewire 966 is advanced through the guidewire lumen, as in FIG. 21B, slit 964 opens to allow guidewire 966 to exit distal end 962. Slit 964 allows distal end 962 to remain closed while being advanced through tissue, and the tapered distal end 962 facilitates atraumatice passage of the guide member through tissue. In an alternative embodiment, distal end 962 may include a circular opening at its far distal tip, rather than slit 962.

Figures 22A, 22B:
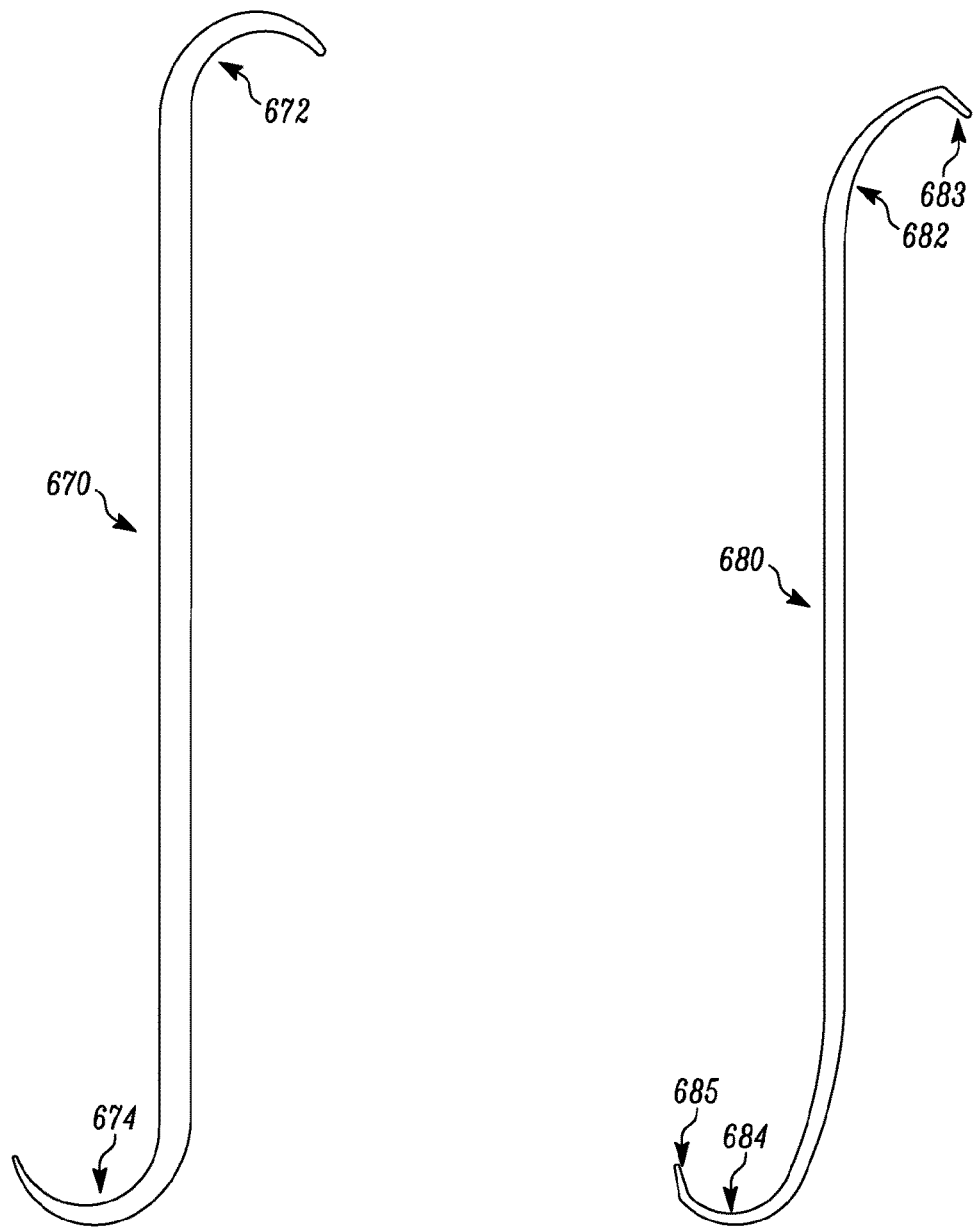
FIGS. 22A and 22B are side views of probes having different shapes according to alternative embodiments of the present invention.
Figure 22C:
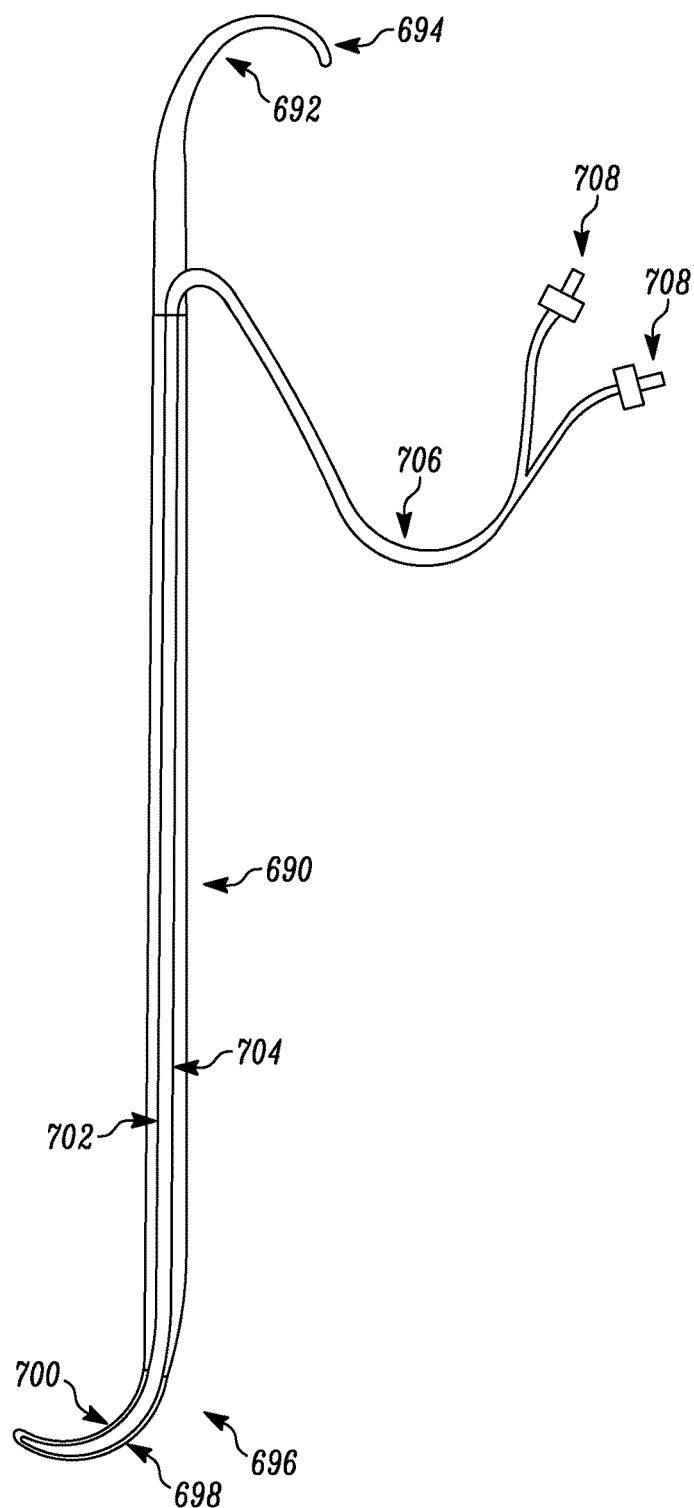
FIG. 22C is a side view of a probe having yet another shape and having two electrodes according to one embodiment of the present invention.

With reference now to FIGS. 22A-22C, three additional embodiments of various probe devices 670, 680, 690 are shown. As illustrated in FIG. 22A, in one embodiment, a probe 670 may include opposite curved ends 672, 674 with similar radii of curvature. In another embodiment, as in FIG. 22B, a probe 680 may include opposite ends 682, 684 with different radii of curvature. This may be advantageous, for example, in facilitating access to two different areas in a spine or to the same area from two different approaches, as described above. In some embodiments, one or both extreme distal ends of probe 680 may include a toe 683, 685 (or lip), comprising a tip with a steeper radius of curvature than an immediately proximal portion of probe 680. Such a toe 683, 685 may facilitate, for example, acquiring tactile feedback when applied against a bony surface.

FIG. 22C shows another embodiment of a probe 690, in this case shown with electrodes 698, 700 coupled with wires 702, 704 extending to a common cord 706 that splits to two power connectors 708. In this embodiment, probe's 690 two opposite curved ends 692, 696 have slightly different shapes, with one end 692 having a lip 694. Such a lip 694 may help facilitate tactile sensation during placement of probe 690. In various embodiments, a system or set of multiple probes may be provided, each probe having different characteristics, shapes, sizes or the like, to provide a surgeon or other practitioner with alternative probes during a procedure.

Figure 23A:
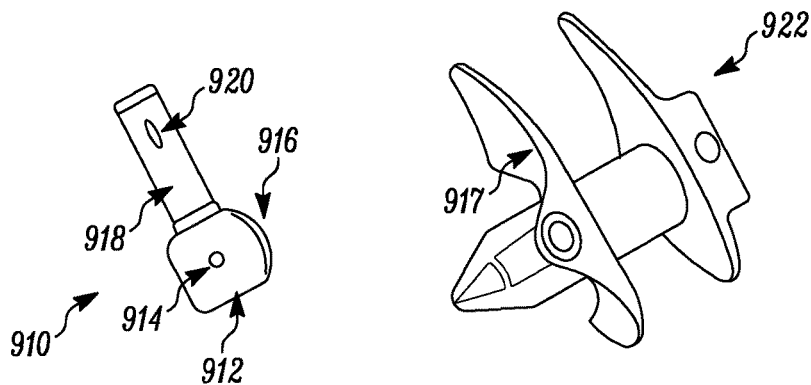
FIG. 23A is a perspective view of a spinal decompression device and a probe device having a complementary surface shape to slide along the decompression device according to one embodiment of the present invention.
Figure 23B:
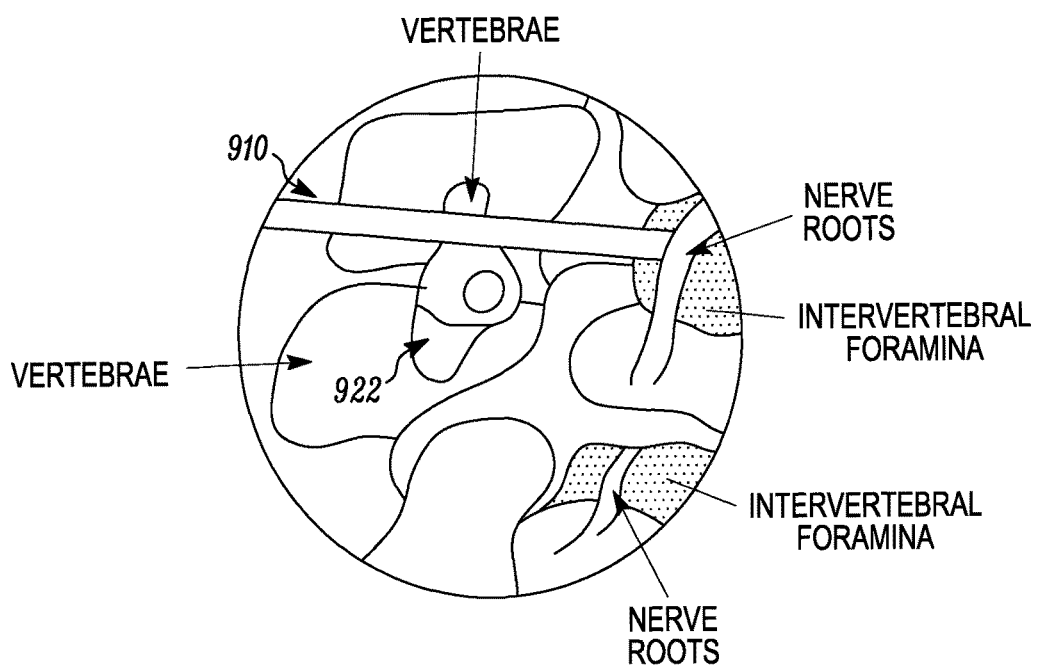
FIG. 23B is a side view of a portion of a spine, showing the spinal decompression device and probe of FIG. 23A in place according to one embodiment of the present invention.

Referring to FIGS. 23A and 23B, in some embodiments it may be advantageous to use a probe device 910 in a spine where a decompression implant 922 has been placed. For example, decompression implant 922 shown in FIGS. 23A and 23B is the X STOP®. Interspinous Process Decompression (IPD®), offered by St. Francis Medical Technologies, Inc. ® (Alameda, Calif.). In one embodiment, probe 910, which is shown in top view in FIG. 23A and partial side view in FIG. 23B, may include a shaft 912 with a guidewire channel 914 and a curved side surface 916, and a distal curved portion 918 with a distal opening 920. Curved side surface 916 may be shaped to slide along a complementary surface 917 of decompression implant 922 as probe 910 is advanced into the patient, which may facilitate guiding probe 910 to a desired position, such as to position distal portion 918 in an intervertebral foramen, as in FIG. 23B. In various alternative embodiments, probe 910 may have any of a number of configurations and sizes to conform to or fit within any of a number of spinal decompression implants.

Figure 24:
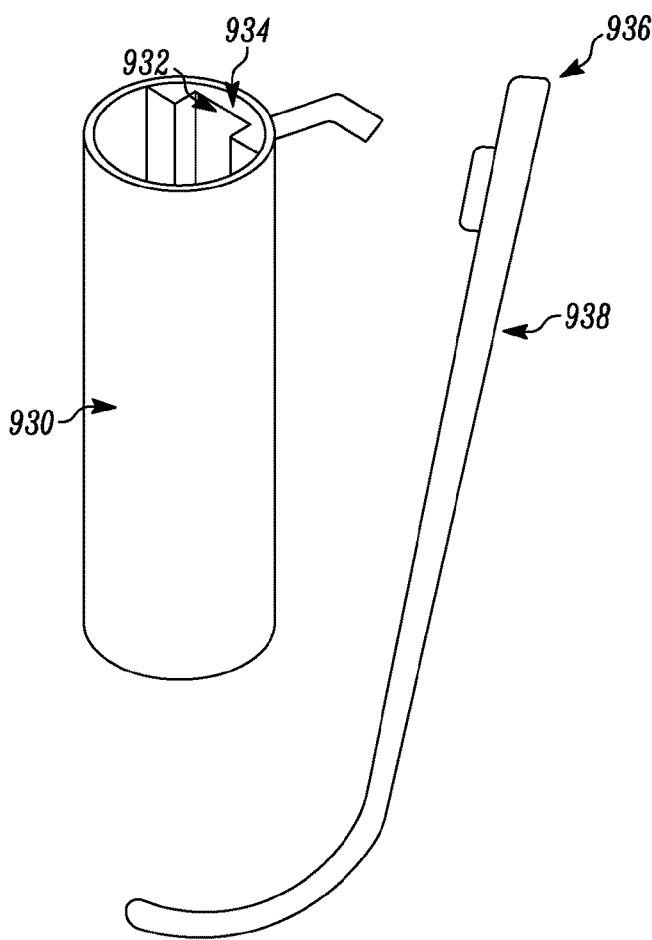
FIG. 24 is a side and perspective view, respectively, of an access port device for accessing a spine and a probe device having a surface shaped to slide through guide member of the access device according to one embodiment of the present invention.
Figure 25:
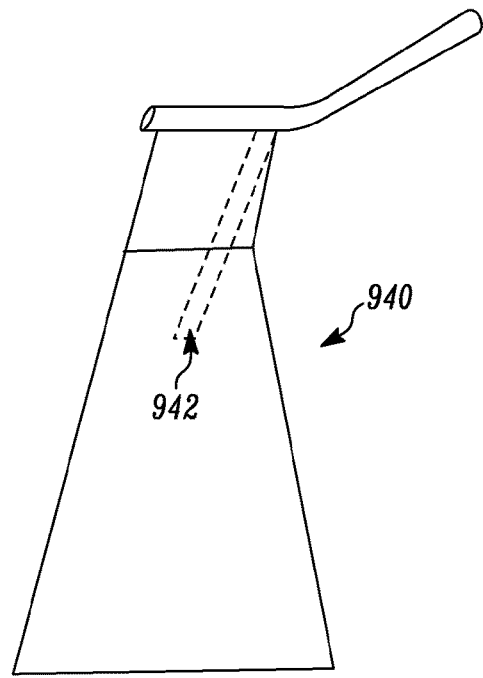
FIG. 25 is a side view of an access port device for accessing a spine, including a probe guide member according to one embodiment of the present invention.

In another embodiment, and with reference now to FIGS. 24 and 25, in some instances a probe device 936 may be used with one or more tubular spinal access conduit devices 930. Examples of such access systems include the METRx™ System, offered by Medtronic Sofamor Danek (Minneapolis, Minn.), the Harmony™ PLIF Instrument System, offered by Spinal Concepts, Inc. (Austin, Tex.) and the Atavi® Atraumatic Spin Surgery System, offered by Endius, Inc. (Plainville, Mass.). In one embodiment, as shown in FIG. 24, probe 936 may include a surface 938 or overall configuration to facilitate its advancement along a complementary surface 932 on a guide member 934 in access conduit 930. In the same or an alternative embodiment, probe 936 may be shaped to pass through a channel 942 in a conduit device 940, as in FIG. 25. In some embodiments, probe 936 may be compatible with multiple different conduit devices 930, 940. In other embodiments, multiple probes may be provided in a set, to provide compatibility with multiple different conduit devices 930, 940. In various embodiments of the invention, a system may be provided, including one or more probe devices, one or more decompression implants and/or one or more access conduits.

Referring now to FIGS. 26A-26E, in the embodiments described above, the various tissue modification devices 102, 202 include at least one non-tissue-modifying (or "protective") portion, side or surface. The non-tissue-modifying portion is located on tissue modification device 102, 202 so as to be positioned adjacent non-target tissue when tissue modifying members 110, 210 are facing the target tissue. The non-tissue-modification surface of the device is configured so as to not modify or damage tissue, and thus the non-target tissue is protected from unwanted modification or damage during a tissue modification procedure.

Optionally, in some embodiments, tissue modification devices or systems may further include one or more tissue shields or barriers for further protecting non-target tissues. Such shields may be slidably coupled with, fixedly coupled with, or separate from the tissue modification devices with which they are used. In various embodiments, a shield may be delivered between target and non-target tissues before delivering the tissue modification device, may be delivered along with the tissue modification device, or may be delivered after delivery of the tissue modification device but before the device is activated. Generally, such a shield would be interposed between the non-target tissue and the tissue modification device.

Figure 26A:
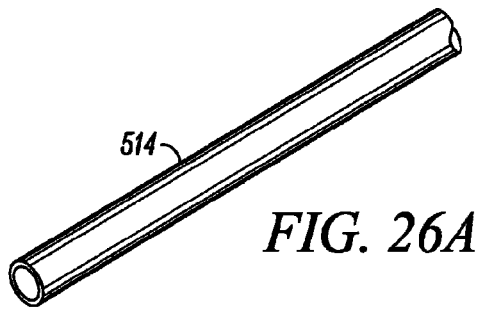
FIG. 26A is a perspective view of a distal portion of an introducer sheath according to one embodiment of the present invention.
Figure 26B:
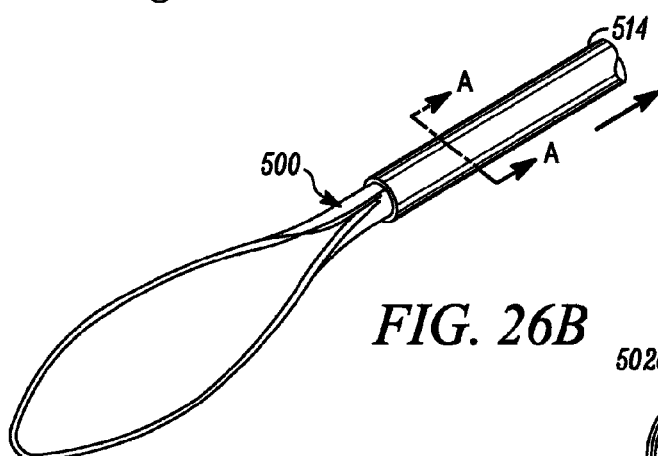
FIGS. 26B and 26C are perspective and cross-sectional views, respectively, of a tissue shield device according to one embodiment of the present invention.
Figure 26C:
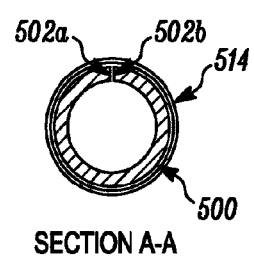
Figure 26D:
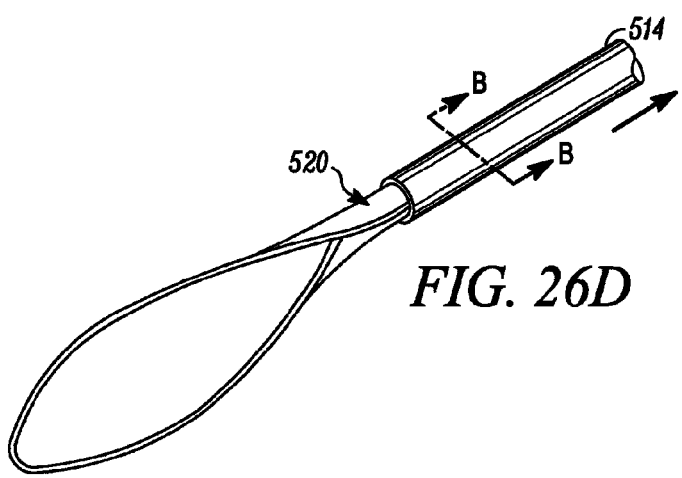
FIGS. 26D and 26E are perspective and cross-sectional views, respectively, of a tissue shield device according to an alternative embodiment of the present invention.
Figure 26E:
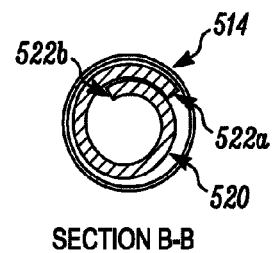

FIG. 26A shows a distal portion of an introducer device 514 through which a shield may be introduced. FIGS. 26B and 26C show one embodiment of a shield device 500 partially deployed and in cross-section, respectively. Typically, shield 500 will have a first, small-profile configuration for delivery to an area near non-target tissue and a second, expanded configuration for protecting the non target tissue. Shield itself may be configured as one piece of super-elastic or shape-memory material, as a scaffold with material draped between the scaffolding, as a series of expandable wires or tubes, as a semicircular stent-like device, as one or more expandable balloons or bladders, as a fan or spring-loaded device, or as any of a number of different devices configured to expand upon release from a delivery device to protect tissue. As shown in FIGS. 26B and 26C, shield 500 may comprise a sheet of material disposed with a first end 502a abutting a second end 502b within introducer device 514 and unfurling upon delivery. In an alternative embodiment, as shown in FIGS. 26D and 26E, opposite ends 522a and 522b of a shield device 520 may overlap in introducer device 514. Generally, shield 500, 520 may be introduced via introducer device 514 in one embodiment or, alternatively, may be introduced via any of the various means for introducing the tissue modification device, such as those described in conjunction with FIGS. 7A-7S, 8A-8F, 9A-9B, 10A-10F, and 11A-11E. In some embodiments, shield 500, 520 may be fixedly coupled with or an extension of a tissue modification device. Shield 500, 520 may also include one or more lumens, rails, passages or the like for passing a guidewire or other guide member, for introducing, removing or exchanging any of a variety of tissue modification, drug delivery, or diagnostic devices, for passing a visualization device, for providing irrigation fluid at the tissue modification site, and or the like. In some embodiments, shield 500, 520 is advanced over multiple guidewires and the guidewires remain in place during a tissue modification procedure to enhance the stability and/or maintain positioning of shield 500, 520.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. For example, in many of the embodiments described above, one or more abrasive tissue modifying members may be substituted for one or more bladed tissue modifying members or vice versa. These an many other modifications may be made to many of the described embodiments. Therefore, the foregoing description is provided primarily for exemplary purposes and should not be interpreted to limit the scope of the invention as it is set forth in the claims.

What is claimed is:
1. A device for detecting if neural tissue is above or below a given region of a device, the device comprising:

a probe having a proximal rigid elongate shaft and a distal end, the distal end being flexible such that it may be articulated to form more than one curved shape and the distal end being substantially flat and having an axial length, a width, and a thickness, wherein the axial length is greater than the width and the width is greater than the thickness, the distal end further having a first upper and second lower laterally oriented surfaces, wherein the upper surface is opposite and separated by the thickness from the lower surface;

a first signal transmitter configured to deliver a neural localization signal disposed along the first upper surface of the probe;

a second signal transmitter configured to deliver a neural localization signal disposed along the second lower surface of the probe, wherein by monitoring a response to the neural localization signals from the first upper surface and the second lower surface, the orientation of the neural tissue relative to the upper surface and the lower surface of the probe can be safely verified.

2. The device of claim 1, wherein the first and second signal transmitters comprise first and second electrodes.

3. The device of claim 1, wherein the distal portion of the probe is configured to facilitate passage of the distal portion of the probe into an intervertebral foramen of a spine.

4. The device of claim 1, further comprising: a wire for pushing or pulling to position the distal end of the probe; and at least one tissue removal device for advancing along or being pulled into position by the wire to remove tissue from the body.

5. The device of claim 1, further comprising at least one sizing probe configured to perform at least one of the functions of assessing an amount of space between tissues before advancing the probe, increasing the amount of space between tissue before advancing the probe, and assessing the amount of space between tissues after performing a tissue modification procedure.

6. A device for determining if neural tissue is above or below a given region of a device in a human body, the device comprising:

a elongate probe having a proximal rigid elongate shaft portion and a distal portion, the distal portion being flexible such that it may be articulated to form more than one curved shape and the distal portion being substantially flat and having an axial length, a width, and a thickness, wherein the axial length is greater than the width and the width is greater than the thickness, the distal portion further having a first upper surface separated by the thickness from an opposite second lower surface;

a first electrode coupled with the first surface of the probe at or near the distal portion and connectible with at least one energy source configured to deliver increasing levels of energy to the first upper surface to determine a first stimulation level at which the neural tissue responds; and at least a second electrode coupled with the second surface of the probe at or near the distal portion and connectible with an energy source configured to deliver increasing levels of energy to the second lower surface to determine a first stimulation level at which the neural tissue responds, wherein proximity of a nerve as is closer to the upper surface or the lower surface of the device may be determined based upon the first stimulation level from the first electrode and the first stimulation level from the second electrode.

7. The device of claim 6, further comprising a barrier member configured to couple to the second lower surface of the probe.

8. The device of claim 6, further comprising: a guidewire configured to couple to a distal end portion of the probe; and at least one tissue removal device for advancing along or being pulled into position by the guidewire to remove tissue from the body.

9. The device of claim 8, further comprising a barrier member configured to couple to the second lower surface of the probe and to be pulled into position by the guidewire.

10. The device of claim 8, wherein the probe is configured to be pulled into position by the guidewire.

11. The device of claim 6, further comprising at least one wire coupled with the distal portion for pushing or pulling to position the distal portion.

12. The device of claim 6, wherein the probe further comprises at least one lumen having a proximal opening and a distal opening, the proximal opening of the probe lumen is sized to allow passage of a guidewire, so that the guidewire may be passed into the proximal opening and out a distal opening.

13. A device for detecting if neural tissue is above or below a given region of a device, the device comprising:

a probe having a proximal rigid elongate shaft and a distal end, the distal end being flexible such that it may be articulated to form more than one curved shape and the distal end being substantially flat and having an axial length, a width, and a thickness, wherein the axial length is greater than the width and the width is greater than the thickness, the distal end further having a first upper and a second lower laterally oriented surfaces, wherein the upper surface is opposite and separated by the thickness from the lower surface; and a first signal transmitter configured to deliver a neural localization signal disposed along the first upper surface of the probe;

wherein by monitoring a response to the neural localization signal from the first upper surface, the orientation of the neural tissue relative to the upper surface and the lower surface of the probe can be safely verified.

* * * * *